(12) United States Patent
Beauglehole et al.

(10) Patent No.: US 7,217,702 B2
(45) Date of Patent: May 15, 2007

(54) SELECTIVE ANTAGONISTS OF A2A ADENOSINE RECEPTORS

(75) Inventors: Anthony Beauglehole, Charlottesville, VA (US); Jayson M. Rieger, Charlottesville, VA (US); Robert D. Thompson, Charlottesville, VA (US)

(73) Assignee: Adenosine Therapeutics, LLC, Charlottesville, VA (US)

( * ) Notice: Subject to any disclaimer, the term of this patent is extended or adjusted under 35 U.S.C. 154(b) by 0 days.

(21) Appl. No.: 11/097,251

(22) Filed: Apr. 4, 2005

(65) Prior Publication Data

US 2005/0282831 A1 Dec. 22, 2005

Related U.S. Application Data

(60) Provisional application No. 60/559,159, filed on Apr. 2, 2004.

(51) Int. Cl.
  *C07D 473/34* (2006.01)
  *C07D 211/16* (2006.01)
  *A61K 31/52* (2006.01)
  *A61P 25/14* (2006.01)
  *A61P 25/16* (2006.01)

(52) U.S. Cl. .......... 514/81; 514/234.2; 514/228.5; 514/263.2; 514/263.21; 514/263.22; 514/263.23; 514/263.37; 514/263.4; 544/61; 544/118; 544/244; 544/276; 544/277

(58) Field of Classification Search .......... 544/61, 544/118, 244, 276, 277; 514/81, 234.2, 228.5, 514/263.2, 263.21, 263.22, 263.23, 263.37, 514/263.4

See application file for complete search history.

(56) References Cited

U.S. PATENT DOCUMENTS 4,293,690 A * 10/1981 Sawa et al. .......... 536/27.61
4,341,769 A * 7/1982 Marumoto et al. .......... 514/46
5,189,027 A * 2/1993 Miyashita et al. .......... 514/46
5,681,941 A * 10/1997 Cook et al. .......... 536/23.1
6,329,381 B1 * 12/2001 Kurimoto et al. .......... 514/263.23
6,387,889 B1 * 5/2002 Endo et al. .......... 514/46
2004/0043388 A1 * 3/2004 Come et al. .......... 435/6
2005/0187228 A1 * 8/2005 Haesslein .......... 514/263.37

OTHER PUBLICATIONS

Cesnek et al., Collection of Czechoslovak Chemical Communications 68(11), 2201-2218.*
Camaioni et al., Bioorganic & Medicinal Chemistry, vol. 6(5) May 1998, pp. 523-533.*
Ying Zhao et at., J. Am. Chem., Soc.; 2003; 125(9) pp. 2480-2488.*
Klotz, Naunyn-Schmiedeberg's Archives of Pharmacology 367(3) 629-634 (2003).*
Baker, J. Org Chem., 19(11) 1793 (1954).*
Abiru, J. Med. Chem 35, 2253 (1992).*
Gray, Tetrahedron Letters vol. 38, Issue 7, Feb. 17, 1997, pp. 1161-1164.*

* cited by examiner

*Primary Examiner*—Mark L. Berch
(74) *Attorney, Agent, or Firm*—Williams Mullen; Kelly J. Hollowell

(57) ABSTRACT

Selective antagonists of $A_{2A}$ adenosine receptors like those of formula I are provided, wherein Y forms a ring.

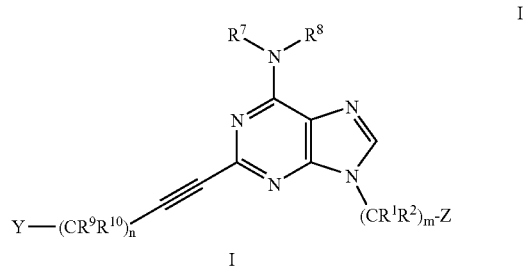

The novel $A_{2A}$ blockers are useful for the treatment of Parkinsons disease and other diseases.

86 Claims, 2 Drawing Sheets

SELECTIVE ANTAGONISTS OF A2A ADENOSINE RECEPTORS

This application claims the benefit of U.S. Provisional Application No. 60/559,159, filed Apr. 2, 2004, entitled "Selective Antagonists of A2A Adenosine Receptors" the disclosure of which is incorporated herein in its entirety.

FIELD OF THE INVENTION

The present invention relates to compounds and pharmaceutical compositions that are selective antagonists of the $A_{2A}$ adenosine receptor (AR). These compounds are useful as pharmaceutical agents.

Selective antagonists of $A_{2A}$ adenosine receptors have proven to be effective for the treatment of Parkinson's disease (PD) both in animal models and in a human trial.[1] However, the initial clinical trial was stopped in phase 3 due to detection of animal toxicity of the investigational drug, KW6002. Other investigational compounds lack sufficient potency, selectivity or bioavaility to be considered clinical candidates.

BACKGROUND OF THE INVENTION

Parkinson's disease is the second most common neurodegenerative disorder and affects over 1 million people in North America.[2] The pathological process, degeneration of the dopaminergic neurons in the substantial nigra, causes profound depletion of striatal dopamine and motor impairment. This insight led to the introduction of L-dopa as a dopamine-replacement treatment for PD.[3] Today, L-dopa continues to be the "Gold Standard" treatment for the motor symptoms of PD.[4,5] Despite the considerable symptomatic relief it affords, long-term treatment with L-dopa has major limitations.[6] After five to ten years of treatment with L-dopa, up to 60% of patients experience loss of L-dopa effectiveness and some debilitating complications,[7,8] notably, an "on" and "off" motor fluctuation and involuntary choreic or dystonic movements, dyskinesia. This has become the limiting factor in management of patients in the later stages of PD.[9] The development of dyskinesia might reflect desensitization of dopamine receptors.[10] Most importantly, there is no clear evidence that L-dopa slows or halts the degeneration of dopaminergic neurons. In fact, in vitro cell culture studies suggested that dopamine and its oxidative metabolites are toxic to dopaminergic neurons, and raised the concern that L-dopa may actually accelerate the degeneration of dopaminergic neurons. Because of this concern, many clinicians avoid prescribing L-dopa early in the course of PD.[11]

These major limitations of L-dopa therapy are linked to the activation of dopamine receptors. This has prompted a search for alternative treatment for PD not targeting the dopaminergic system.[12] Striatal neuromodulators and transmitters other than dopamine are increasingly appreciated as critical regulators of motor function and offer new therapeutic opportunities to complement dopamine-replacement.

Over the last 10 years, the $A_{2A}$ adenosine receptor ($A_{2A}$AR) has received increasing attention as a treatment for PD.[13,14] This contention is based on our understanding of the role of the $A_{2A}$AR in the basal ganglia and on the recent development of new, more selective $A_{2A}$AR antagonists. Anatomical, neurochemical and behavioral evidence of adenosine-dopamine interactions underlie this new therapeutic approach.[15-17] Anatomically, $A_{2A}$AR density is high in the striatum, where receptor mRNA is co-expressed with $D_2$ receptor mRNA in the striatopallidal neurons.[18-20] This unique cellular distribution of $A_{2A}$ receptors suggests that $A_{2A}$ receptor antagonists can selectively modulate the "indirect" striatopallidal pathway to affect motor activity. At the neurochemical level, activation of the $A_{2A}$AR reduces the binding affinity of $D_2$ receptors in the striatum,[21] and antagonizes many neurochemical and cellular changes brought about by the activation of striatal $D_2$ receptors, including release of acetylcholine and GABA and expression of c-Fos. Furthermore, behavioral studies have demonstrated that the unselective adenosine antagonists caffeine and theophylline stimulate locomotor activity[22,23] whereas the unselective agonist NECA[24] inhibits spontaneous locomotor activity as well as motor activity induced by dopamine agonists. Thus, $A_{2A}$AR agonists and antagonists function as dopamine antagonists and agonists, respectively, in modulating motor activity. The three possible mechanisms have been proposed to explain for motor enhancement by the $A_{2A}$ antagonists: (1) a direct receptor-receptor ($A_{2A}$-$D_2$) antagonistic interaction,[25,26] (2) an opposing but independent of $A_{2A}$ and $D_2$ receptor signaling[27-29] or (3) $A_{2A}$AR modulation of GABA release in the basal ganglia.[30-32] These receptors also form $A_{2A}$AR-D2 heterodimers,[33] but how dimerization affects receptor function is unclear.

$A_{2A}$ Receptor Antagonists May Offer Multiple Therapeutic Benefits for PD Patients First, $A_{2A}$ antagonists stimulate motor activity in normal as well as dopamine-depleted animals. In rodent models of PD, unselective adenosine antagonists (caffeine and theophylline)[22,34] and the $A_{2A}$AR-selective antagonists SCH58261, KW6002 and CSC can reverse motor deficits induced by MPTP, 6-hydroxydopamine, haloperidol or reserpine[35-41] as well as by genetic deletion of $D_2$ receptors.[42] More recently, the $A_{2A}$ antagonists KW6002 reversed motor deficit in MPTP-treated non-human primates.[43,44] Furthermore, $A_{2A}$ antagonists can stimulate motor activity when combined with sub-threshold doses of dopaminergic agents such as L-dopa or $D_1$ and $D_2$ agonists such as aporphormine or quinpirole.[45] For example, combining KW6002 with L-dopa reduces the dose of L-dopa, thereby reducing the complications associated with L-dopa. In contrast to some non-specific adenosine antagonists or some dopamine agonists, motor stimulation was observed after acute treatment and persisted following treatment continued for 15 days.[44,46,47] Thus, tolerance to the motor stimulant effect of $A_{2A}$ antagonists did not develop.

Second, studies of the MPTP-treated monkey model of PD revealed a novel feature of $A_{2A}$ antagonists, namely, stimulation of motor activity without dyskinesia.[43,44,48] In contrast to L-dopa, repeated treatment with KW6002 reversed the motor deficit but did not induce dyskinesia, even in monkeys primed with L-dopa. Further, our recent findings in $A_{2A}$AR knockout mice suggest that development of behavioral sensitization by chronic treatment of L-dopa requires activation of the $A_{2A}$AR. Genetic inactivation of the $A_{2A}$ receptor attenuated L-dopa-induced rotational behavior.[49] This is consistent with a recent study showing that co-administration of KW6002 with apomorphine to MPTP-treated monkeys completely abolished the development of apomorphine-induced dyskinesia.[50] Further studies are warranted to explore the molecular mechanism underlying this novel aspect of $A_{2A}$AR function.

Third, accumulating evidence suggests that the specific inactivation of $A_{2A}$ARs consistently attenuates brain damage induced by ischemia[51,53] and excitoxicity,[54,55] as well as in animal models of Huntington's disease[56] and Alzheimer's disease.[57] The neuroprotection by $A_{2A}AR$ antagonists has been recently extended to a rodent model of PD. Co-administration of $A_{2A}AR$ antagonists, such as CSC, DMPX, SCH58261 and KW6002 (but not the $A_1AR$ antagonist DPCPX) attenuated dopaminergic neurotoxicity in several neurotoxin models of PD.[58] $A_{2A}AR$ antagonists provided not only functional protection (such as reduced dopamine content and expression of molecular markers for the dopaminergic terminals), but also reduced the loss of dopaminergic neurons in substantia nigra in both MPTP- and 6-OHDA models of PD.[59,60] Likewise, knockout of $A_{2A}ARs$ attenuated MPTP-induced dopaminergic neurotoxicity in mice.[59] Together with the demonstration of neuroprotection by $A_{2A}AR$ antagonists against a wide range of neuronal injury models. These results raise the possibility that $A_{2A}$ antagonists may offer a neuroprotection, slowing or even halting degeneration of dopaminergic neurons.

Finally, in contrast to the widespread distribution of other neurotransmitter receptors, for example, glutamate receptors, the expression of the $A_{2A}AR$ is almost exclusively in striatum, which might allow selective modulation of dopamine-mediated motor pathways without serious side effects due to drug actions outside the basal ganglia (a serious problem for drugs such as glutamate antagonists). It is important to emphasize that ambient adenosine levels and $A_{2A}AR$ density are normal in PD patients,[61] indicating that $A_{2A}$ antagonists might remain effective, even in the later stages of PD.

The prospective use of $A_2AR$ antagonists as potential neuroprotective agents against dopaminergic neuron degeneration was markedly enhanced by a May 2000 report of an epidemiological study of the relationship between caffeine and PD. Ross et al described a large prospective study with a 30-year follow-up of 8004 Japanese-American men that showed that in this population there is an inverse relationship between caffeine consumption and the risk of developing PD.[62] Two other ongoing, large-cohort studies (Heath Professional Follow-up Studies and Nurse's Heath Study) involving 47,351 men and 88,565 women also showed that moderate caffeine consumption (3–5 cups/day) reduced their risk of developing PD.[63] Thus, the inverse relationship of caffeine consumption and the risk of developing PD seem firmly established by these two large, prospective epidemiological studies. These results are consistent with the animal studies showing neuroprotection by $A_{2A}AR$ antagonists and strongly argue that $A_{2A}$ antagonists including caffeine may offer an opportunity to slow down or halt the degeneration of dopaminergic neurons.

Initial clinical trial results of KW6002 indicated that (20–80 mg/day) enhanced motor activity in one study and potentiated a motor stimulant effect by low (but not high) doses of L-dopa in another study.[64,65] KW6002 was well tolerated and had few side effects. Unfortunately, trials with KW6002 have been stopped because this compound was found to produce a long-term toxicity in rats. Hence, there is a pressing need to develop alternative molecules that lack toxicity.

The first relatively selective $A_{2A}AR$ antagonists, the 8-styrylxanthines, appeared about ten years ago. This class includes KW-6002, which has low nanomolar affinity for the $A_{2A}AR$ and >100-fold selectivity for the $A_{2A}AR$ over the $A_1AR$. KW-6002, entered clinical trials in 2002 as an agent for the treatment of PD.[1,66] SCH58261, a pyrazolo[4,3-e]-1,2,4triazolo[1,5-c]pyrimidine was a prototype for a series of second-generation derivatives that appeared over the next several years. These, too, had low nanomolar affinity and good selectivity for the $A_{2A}AR$ in vitro.[67] The third class of antagonists to appear, the 1,2,4-triazolo[4,5-e]-1,3,5-triazines, was typified by ZM241385, which was active at the $A_{2A}AR$ in the sub-nanomolar range but less selective, interacting with $A_{2B}AR$ as well.[68] These potent $A_{2A}$ antagonists have been important research tools, greatly facilitating pharmacological investigations of $A_{2A}AR$ function in vitro as well as in vivo significantly enhancing our understanding of the neurobiology of the $A_{2A}AR$. However, each of these antagonists has important drawbacks. KW-6002 is light-sensitive, undergoing photoisomerization from the active E-isomer to the 800-fold less active Z-isomer.[69] SCH58261 is very poorly soluble and even its second-generation derivatives have marginal bioavailability.[70] As mentioned above, ZM241385 is unselective and, additionally, has poor bioavailability. Other nitrogen heterocycles such as the 1,2,4-triazolo[4,3-a]quinoxalin-1-ones[71] and the oxazolo[4,5-d]pyrimidines from ICI are also unselective, and their bioavailability is unknown. Therefore a continuing need exists for compounds that are selective $A_{2A}$ AR antagonists.

SUMMARY OF THE INVENTION

In one aspect, there is provided a compound of the formula I:

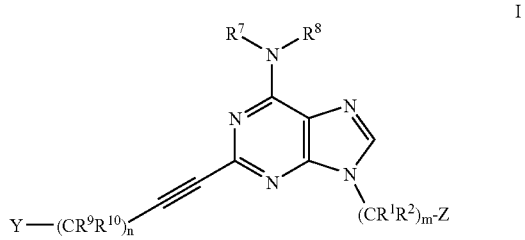

wherein $R^1$ and $R^2$ are each independently selected from the group consisting of hydrogen, halogen, —$NH_2$, —OH, —SH, —$NHCH_3$, —$N(CH_3)_2$, —OMe, —SMe, $(C_1$–$C_8)$ alkyl, aryl and aryl$(C_1$–$C_8)$alkyl, wherein $R^1$ and $R^2$ are optionally substituted with 1 to 4 substituents of $R^a$, wherein the alkyl is optionally interrupted by 1–4 heteroatoms selected from —O—, —S—, —SO—, —$S(O)_2$— or amino (—$NR^a$—), or where $R^1$ and $R^2$ are independently absent, with the proviso that $R^a$ is not thio or halogen in the case where $R^1$ and $R^2$ to which $R^a$ is bound is halogen, —$NH_2$, —OH, —SH, —$NHCH_3$, —$N(CH_3)_2$, —OMe and —SMe; $R^3$ is selected from the group consisting of hydrogen, halo, —$OR^a$, $SR^a$, $(C_1$–$C_8)$alkyl, cyano, nitro, trifluoromethyl, trifluoromethoxy, $(C_3$–$C_8)$cycloalkyl, heterocycle, heterocycle$(C_1$–$C_8)$alkyl, aryl, aryl$(C_1$–$C_8)$alkyl, heteroaryl, heteroaryl$(C_1$–$C_8)$alkyl, —$CO_2R^a$, $R^aC$(=O)O—, $R^aC$(=O)—, —$OCO_2R^a$, $R^aR^bNC$(=O)O—, $R^bOC$(=O)N$(R^a)$—, $R^aR^bN$—, $R^aR^bNC$(=O)—, $R^aC$(=O)N$(R^b)$—, $R^aR^bNC$(=O)N$(R^b)$—, $R^aR^bNC$(=S)N$(R^b)$—, —$OPO_3R^a$, $R^aOC$(=S)—, $R^aC$(=S)—, —$SSR^a$, $R^aS$(=O)—, $R^aS$(=O)$_2$—, —$NNR^a$ and —$OPO_2R^a$; or if the ring formed from the group $CR^3R^4R^5$ is aryl or heteroaryl or partially unsaturated, then $R^3$ can be absent; $R^4$ and $R^5$ together with the atoms to which they are attached form a saturated or partially unsaturated, mono-, bi- or tricyclic- or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —$S(O)_2$— or amine (—$NR^a$—) in the ring, wherein any ring comprising $R^4$ and $R^5$ is optionally further substituted with from 1 to 14 $R^6$ groups; wherein each $R^6$ is independently selected from the group consisting of halo, —$OR^a$, —$SR^a$, substituted or unsubstituted ($C_1$–$C_8$)alkyl, cyano, nitro, trifluoromethyl, trifluoromethoxy, ($C_1$–$C_8$)cycloalkyl, ($C_6$–$C_{12}$)bicycloalkyl, heterocycle, hetrocyclyl($C_1$–$C_8$)alkyl, aryl, aryl($C_1$–$C_8$)alkyl, heteroaryl, heteroaryl($C_1$–$C_8$)alkyl, —$CO_2R^a$, $R^aC(=O)$ O—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, —$NNR^a$ and —$OPO_2R^a$ or two $R^6$ groups and the atom to which they are attached combined to form C=O or C=S, or wherein two $R^6$ groups together with the atom or atoms to which they are attached can form a carbocyclic or heterocyclic ring; $R^7$ and $R^8$ are each independently hydrogen, ($C_1$–$C_8$)alkyl, ($C_3$–$C_8$)cycloalkyl, aryl or aryl($C_1$–$C_8$) alkylene, heteroaryl, heteroaryl($C_1$–$C_8$)alkylene-; or wherein $R^7$ and $R^8$ together with the nitrogen atom to which they attach form a heterocycle or heteroaromatic ring; $R^9$ and $R^{10}$ are each independently selected from the group consisting of hydrogen, halogen, —$NH_2$, —OH, —SH, —$NHCH_3$, —$N(CH_3)_2$, —OMe, —SMe, ($C_1$–$C_8$)alkyl, aryl and aryl($C_1$–$C_8$)alkyl, wherein $R^9$ and $R^{10}$ are optionally substituted with 1 to 4 substituents of $R^a$, wherein the alkyl is optionally interrupted by 1 to 4 heteroatoms selected from —O—, —S—, —SO—, —$S(O)_2$— or amino (—$NR^a$—), or where $R^9$ and $R^{10}$ are independently absent, with the proviso that $R^a$ is not thio or halogen in the case where $R^9$ and $R^{10}$ to which $R^a$ is bound is halogen, —$NH_2$, —OH, —SH, —$NHCH_3$, —$N(CH_3)_2$, —OMe and —SMe; Y is —$CR^3R^4R^5$ or $NR^4R^5$; Z is selected from the group consisting of hydrogen, halogen, ($C_1$–$C_8$)alkyl, ($C_1$–$C_8$)cycloalkyl, ($C_6$–$C_{12}$)bicycloalkyl, ($C_6$–$C_{20}$)polycyclyl, heterocyclyl, cycloalkyl($C_1$–$C_8$)alkyl, bicycloalkyl($C_6$–$C_{12}$)alkyl, heterocyclyl($C_1$–$C_8$)alkyl, aryl, aryl($C_5$–$C_{14}$), aryl($C_1$–$C_8$) alkyl, heteroaryl, heteroaryl($C_1$–$C_8$)alkyl, —$NR^aR^b$, —$OR^a$, —$SR^a$, cyano, nitro, trifluoromethyl, trifluoromethoxy, —$CO_2R^a$, $R^aC(=O)O$—, $R^aC(=O)$—, —$OCO_2R^a$, $R^aR^bNC(=O)O$—, $R^bOC(=O)NR^a$—, $R^aR^bNC(=O)$—, $R^aC(=O)NR^b$—, $R^aR^bNC(=O)NR^b$—, $R^aR^bNC(=S)NR^b$—, —$OPO_3R^a$, $R^aOC(=S)$—, $R^aC(=S)$—, —$SSR^a$, $R^aS(=O)$—, —$NNR^a$, —$OPO_2R^a$, —$OS(O_2)R^a$, —$OS(=O)OR^a$, —$OS(O_2)OR^a$ and —$O(SO_2)NR^aR^b$; $R^a$ and $R^b$ are each independently selected from the group consisting of hydrogen, halogen, —$NH_2$, —OH, —SH, —$NHCH_3$, —$N(CH_3)_2$, —OMe, —SMe, propargyl, cyano, —NNH, —$NNCH_3$, —$OPO_2H$, —$OPO_2CH_3$, —$OS(O_2)H$, —$OS(O_2)OH$, —$OS(O_2)CH_3$, —$OS(O_2)OCH_3$, ($C_1$–$C_8$)alkyl, aryl, aryl($C_1$–$C_8$alkyl, ($C_3$–$C_8$)cycloalkyl, ($C_6$–$C_{12}$)bicycloalkyl, cycloalkyl($C_1$–$C_8$)alkyl, bicycloalkyl ($C_6$–$C_{12}$)alkyl, heteroaryl and heteroaryl($C_1$–$C_8$)alkyl, wherein the alkyl and cycloalkyl are optionally interrupted with 1–4 heteroatoms selected from the group consisting of —O—, —S—, —SO—, —$S(O)_2$— and amino (—$NR^c$—); and wherein the alkyl, cycloalkyl, aryl and heteroaryl are optionally substituted with 1, 2, 3 or 4 substituents selected from the group consisting of —$OR^c$, —$NR^cR^c$, —$SR^c$, cyano, —NNH, —$NNCH_3$, —$OPO_2H$, —$OPO_2CH_3$, —$OS(O_2)H$, —$OS(O_2)OH$, —$OS(O_2)CH_3$ and —$OS(O_2)OCH_3$, provided that $R^a$ is not a heteroatom when it is attached to another heteroatom; $R^c$ is selected from the group consisting of hydrogen and ($C_1$–$C_8$)alkyl; and m is 0 to 8; n is 0, 1, 2 or 3, provided that when m is 0, Z is not halogen, cyano, nitro or a heteroatom, and when n is 0, Y is not —$NR^4R^5$;

or a pharmaceutically acceptable salt thereof, optionally in the form of a single stereoisomer or mixture of stereoisomers thereof.

In another aspect, there is provided a compound of the formula II:

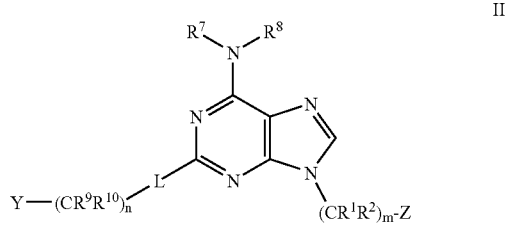

wherein $R^1$, $R^2$, $R^7$, $R^8$, $R^9$, $R^{10}$, m, n, Y and Z are as defined above; and L is a linker selected from the group consisting of —($C_1$–$C_3$)alkyl-C≡C—, —C≡C—($C_1$–$C_3$)alkyl-, —$(CH_2)_{1-3}$—CH=CH—, —CH=CH—$(CH_2)_{1-3}$—, —$(CH_2)_{1-2}$—CH=CH—$CH_2$— and —$CH_2$—CH=CH—$(CH_2)_{1-2}$; or a pharmaceutically acceptable salt thereof, optionally in the form of a single stereoisomer or mixture of stereoisomers thereof.

In another aspect, there is provided a compound of the formula III:

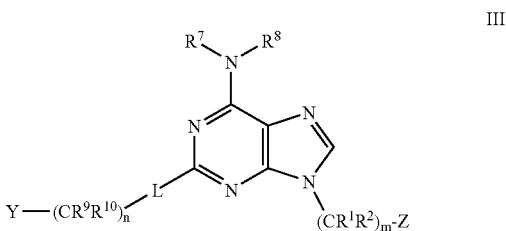

wherein $R^1$, $R^2$, $R^7$, $R^8$, $R^9$, $R^{10}$, m, n, Y and Z are as defined above; and L is a linker selected from the group consisting of —NH—, —N=N—, —NH—N=, —O—, —S—, —$SO_2$— and pyrazolyl; a pharmaceutically acceptable salt thereof, optionally in the form of a single stereoisomer or mixture of stereoisomers thereof.

In one variation of each of the above compound of formulae I, II and III, the group $(CR^1R^2)_m$ together is selected from the group consisting of methylene, ethylene, propylene, butylene, pentylene, hexylene, heptylene, octylene, iso-propylene, iso-butylene, sec-butylene and tert-butylene. In another variation, $(CR^1R^2)_m$ together is selected from the group consisting of methylene, ethylene, propylene and iso-propylene. In another variation, $(CR^1R^2)_m$-Z together is selected from the group consisting of —$CH_2CH=CH_2$—, —$CH_2C≡CH$, —$CH_2C≡CCH_3$ or —$CH_2CH_2C≡CH$. In yet another variation, $(CR^1R^2)_m$-Z together is —$CH_2C≡CH$.

In another variation of the above formulae, $R_1$ and $R_2$ are hydrogen or are absent, m is 2 to 8 and the group $(CR^1R^2)_m$ optionally comprises 1 to 4 alkenyl or alkynyl conjugated or unconjugated groups. In another variation, m is 1 to 8 and Z is selected from the group consisting of —$NH_2$, —OH, —SH, —$NR^aR^b$, —$OR^a$, —$SR^a$ and cyano. In another particular variation, $(CR^1R^2)_m$-Z together is selected from the group consisting of methanol, ethanol, propanol, butanol, pentanol, hexanol, iso-propanol, iso-butanol, sec-butanol and tert-butanol. In yet another variation, $(CR^1R^2)_m$-Z together is selected from the group consisting of methanol, ethanol, propanol and —CH$_2$CN.

In one variation of each of the above, R$_1$ and R$^2$ are hydrogen, and the group $(CR^1R^2)_m$ is linear or branched, m is 1 to 6, and Z is selected from the group consisting of methoxy, ethoxy, propoxy, butoxy, pentoxy and hexyloxy. In another variation, Z is selected from the group consisting of methoxy, ethoxy and propoxy. In another variation, Z is a mono-, bicyclic-, tricyclic- or aromatic or non-aromatic (C$_3$–C$_{20}$)cycloalkyl ring, wherein the ring atoms are optionally interrupted by 1 to 8 heteroatoms selected from the group consisting of —O—, —S—, —SO—, —S(O)$_2$— and amino (—NR$^a$—). In yet another variation, Z is selected from the group consisting of cyclopropyl, cyclobutyl, cyclopentyl, cyclohexyl, cycloheptyl and cyclooctyl ring optionally substituted with 1 to 4 substituents of R$^a$. In yet another variation, Z is selected from the group consisting of cyclopropyl, cyclobutyl, cyclopentyl and cyclohexyl, where m is 0 or 1. In another variation, Z is cyclopentyl and where m is 0. In a particular variation, Z is cyclobutyl, m is 1 and R$^1$ and R$^2$ are hydrogen.

In one particular variation of each of the above; Y and Z are each independently selected from the group consisting of hydrogen, or

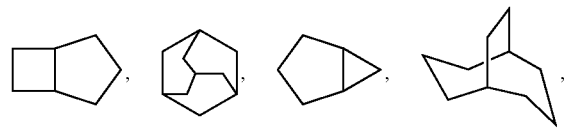
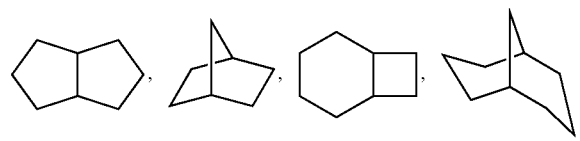
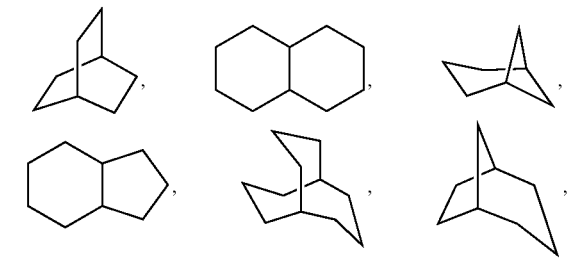
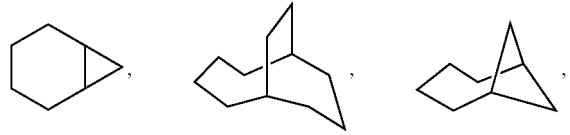
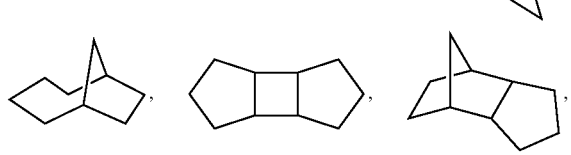

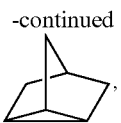

wherein each Y or Z group is optionally comprises 1, 2 or 3 double bonds; each carbon in the ring is optionally replaced by or interrupted by 1 to 6 heteroatoms selected from —O—, —S—, —SO—, —S(O)$_2$—, or amino (—NR$^a$—), and is optionally further substituted with from 1 to 10 R$^6$ groups, provided that the Y or Z ring is not attached at a bridgehead carbon atom or at a trisubstituted carbon atom. In another variation, each Y or Z is independently hydrogen or a bicyclic ring selected from the group consisting of

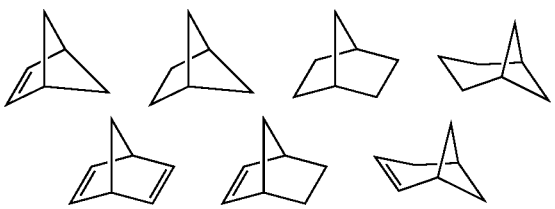

wherein any two adjacent carbon ring atom is optionally interrupted with 1 to 6 heteroatoms selected from —O—, —S—, —SO—, —S(O)$_2$— or amino (—NR$^a$—), and the ring is optionally substituted with from 1 to 7 R$^a$ groups selected from the group consisting of —NH$_2$, —OH, —SH, —NHCH$_3$, —N(CH$_3$)$_2$, —OMe, —SMe, propargyl, cyano, —NNH, —NNCH$_3$, —OPO$_2$H, —OPO$_2$CH$_3$, —OS(O$_2$)H, —OS(O$_2$)OH, —OS(O$_2$)CH$_3$ and —OS(O$_2$)OCH$_3$, and m and n are each independently 0 or 1. In another variation, each Y or Z is independently selected from the group consisting of hydrogen, or

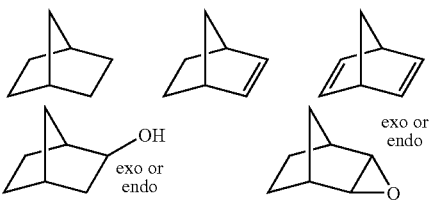

wherein m and n are each independently 0 or 1, and R$^1$, R$^2$, R$^9$ and R$^{10}$ are each independently absent or selected from the group consisting of hydrogen, —NH$_2$, —OH, —SH, —NHCH$_3$, —N(CH$_3$)$_2$—OMe and —SMe, and each Z group is optionally substituted with from 1 to 7 R$^a$ groups selected from the group consisting of halo, —NH$_2$, —OH, —SH, —NHCH$_3$, —N(CH$_3$)$_2$, —OMe, —SMe, propargyl, cyano, —NNH, —NNCH$_3$, —OPO$_2$H, —OPO$_2$CH$_3$, —S(SO$_2$)H, —S(SO$_2$)OH, —S(SO$_2$)CH$_3$ and —S(SO$_2$)OCH$_3$.

In another variation of the above, R$^1$ and R$^2$ are hydrogen, m is 0, 1, 2 or 3 and Z is selected from the group consisting of furan, dihydro-furan, tetrahydrofuran, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with from 1 to 10 $R^a$ groups.

In yet another variation, $R^1$ and $R^2$ are hydrogen, m is 0 or 1, and Z is selected from the group consisting of furan, thiophene, pyrrole, 2H-pyrrole, oxazole, thiazole, imidazole, pyrazole, isoxazole, isothiazole, 1,2,3-oxadiazole, 1,2,4-oxadiazole, 1,2,3-triazole, 1,2,4-triazole, 1,3,4-thiadiazole and 1H-tetrazole, wherein each Z group is optionally substituted with from 1 to 3 $R^a$ groups selected from the group consisting of methyl, ethyl, propyl, iso-propyl, —$NH_2$, —OH, —SH, —$NHCH_3$, —$N(CH_3)_2$, —$OCH_3$ and —$SCH_3$. In another variation, Z is selected from the group consisting of —$CO_2R^a$, $R^aC(=O)O$—, $R^aC(=O)$—, —$OCO_2R^a$, $R^aR^bNC(=O)O$—, $R^bOC(=O)NR^a$—, $R^aR^bN$—, $R^aR^bNC(=O)$—, $R^aC(=O)NR^b$—, $R^aR^bNC(=O)NR^b$—, $R^aR^bNC(=S)NR^b$—, —$OPO_3R^a$, $R^aOC(=S)$—, $R^aC(=S)$—, —$SSR^a$, $R^aS(=O)$—, $R^aS(O_2)$—, —$N=NR^a$, —$OPO_2R^a$, —$OS(O_2)R^a$, —$OS(=O)OR^a$, —$OS(O^2)OR^a$ and —$OS(O_2)NR^aR^b$, wherein m is 1 to 8, and the group $(CR^1R^2)_m$ is optionally saturated or partially unsaturated. In yet another variation, Z is selected from the group consisting of —$CO_2R^a$, $R^aC(=O)O$—, $R^aC(=O)$—, —$OCO_2R^a$, $R^aR^bNC(=O)O$—, $R^bOC(=O)NR^a$—, $R^aR^bN$—, $R^aR^bNC(=O)$—, $R^aC(=O)NR^b$—, $R^aR^bNC(=O)NR^b$—, $R^aR^bNC(=S)NR^b$—, —$OPO_3R^a$, $R^aOC(=S)$—, $R^aC(=S)$—, —$SSR^a$, $R^aS(=O)$—, $R^aS(=O)_2$—, —$N=NR^a$, —$OPO_2R^a$, —$OS(O_2)R^a$, —$OS(=O)OR^a$, —$OS(O^2)OR^a$ and —$O(SO_2)NR^aR^b$, and wherein $(R^1R^2)_m$ together is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —CH=$CHCH_2$—, —$CH_2$CH=CH—, —CH=$CHCH_2CH_2$—, —$CH_2$CH=$CHCH_2$—, —$CH_2CH_2$CH=CH—, —C≡$CCH_2$—, —$CH_2$C≡C—, —C≡$CCH_2CH_2$—, —$CH_2$C≡$CCH_2$— and —$CH_2CH_2$C≡C—. In still another variation of the above, Z is independently —$CO_2R^a$, $R^aC(=O)$—, $R^aR^bN$—, —$OPO_3R^a$, $R^aOC(=S)$—, $R^aC(=S)$—, $R^aS(=O)$—, $R^aS(=O)_2$—, —$OPO_2R^a$, —$OS(O_2)R^a$, —$OS(=O)OR^a$, —$OS(O_2)OR^a$ or —$OS(O_2)NR^aR^b$, and wherein $(CR^1R^2)_m$ together is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —CH=$CHCH_2$—, —$CH_2$CH=CH—, —CH=$CHCH_2CH_2$—, —$CH_2$CH=$CHCH_2$—, —$CH_2CH_2$CH=CH—, —C≡$CCH_2$—, —$CH_2$C≡C—, —C≡$CCH_2CH_2$—, —$CH_2$C≡$CCH_2$— and —$CH_2CH_2$C≡C—.

In one particular variation of each of the above; each $R^9$ is independently selected from the group consisting of hydrogen, halo, —$OR^a$, —$SR^a$, $(C_1-C_8)$alkyl, cyano, nitro, trifluoromethyl, trifluoromethoxy, $(C_3-C_8)$cycloalkyl, heterocyclyl, hetrocyclyl$(C_1-C_8)$alkylene-, aryl, aryl$(C_1-C_8)$alkylene-, heteroaryl, heteroaryl$(C_1-C_8)$alkylene-, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, $R^aS(=O)_2$—, —$N=NR^a$ and —$OPO_2R^a$. In another variation, $R^1$ and $R^2$ together with the carbon atom to which they are attached is C=O, C=S or C=$NR^c$. In yet another variation, $R^3$ is selected from the group consisting of hydrogen, halo, —$OR^a$, —$SR^a$, cyano, nitro, trifluoromethyl, trifluoromethoxy, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, $R^aS(=O)_2$—, —$NNR^a$ and —$OPO_2R^a$; or if the ring formed from the group $CR^3R^4R^5$ is aryl or heteroaryl or partially unsaturated then $R^3$ can be absent. In another variation of the above, $R^3$ is selected from the group consisting of hydrogen, OH, OMe, OAc, $NH_2$, NHMe, $NMe_2$ and NHAc. In a particular variation, $R^3$ is hydrogen or OH.

In one particular variation of each of the above; $R^4$ and $R^5$ together with the atom to which they are attached form a saturated or partially unsaturated, mono-, bi- or tricyclic ring, or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —$S(O)_2$— or amine (—$NR^a$—) in the ring, wherein any ring comprising $R^4$ and $R^5$ is optionally further substituted with from 1 to 14 $R^6$ groups; wherein each $R^6$ is independently selected from the group consisting of halo, —$OR^a$, —$SR^a$, $(C_1-C_8)$alkyl, cyano, nitro, trifluoromethyl, trifluoromethoxy, $(C_1-C_8)$cycloalkyl, $(C_6-C_{12})$bicycloalkyl, heterocycle, hetrocyclyl$(C_1-C_8)$alkyl, aryl, aryl$(C_1-C_8)$alkyl, heteroaryl, heteroaryl$(C_1-C_8)$alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, —$NNR^a$, —$OPO_2R^a$, or two $R^6$ groups and the atom to which they are attached combined to form C=O or C=S, or wherein two $R^6$ groups together with the atom or atoms to which they are attached can form a carbocyclic or heterocyclic ring. In another variation, the ring comprising $R^4$ and $R^5$ and the atom to which they are attached is selected from the group consisting of cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, pyrazolidine, norbornane and adamantane, each unsubstituted or substituted.

In one particular variation of each of the above, $R^6$ is selected from the group consisting of substituted or unsubstituted $(C_1-C_8)$alkyl, —$OR^a$, —$CO_2R^a$, $R^aC(=O)$—, $R^aC(=O)O$—, $R^aR^bN$—, $R^aR^bNC(=O)$— and aryl, provided that when the ring comprising $R^4$ and $R^5$ contains a heteroatom that is O or S, the heteroatom is not substituted with $R^6$. In another variation, $R^6$ is selected from the group consisting of OH, OMe, methyl, ethyl, t-butyl, —$CO_2R^a$, —$CONR^aR^b$, OAc, $NH_2$, NHMe, $NMe_2$, NHEt and $N(Et)_2$, provided that when the ring comprising $R^4$ and $R^5$ contains a heteroatom that is O or S, the heteroatom is not substituted with $R^6$. In yet another variation, $R^6$ is selected from the group consisting of methyl, ethyl, —$CO_2R^a$, —$CONR^aR^b$ and OAc, provided that when the ring comprising $R^4$ and $R^5$ contains a heteroatom, the heteroatom is not substituted with OAc. In yet another variation, $R^6$ is selected from the group consisting of —$(CH_2)_{1-2}OR^a$, —$(CH_2)_{1-2}C(=O)OR^a$, —$(CH_2)_{1-2}OC(=O)R^a$, —$(CH_2)_{1-2}C(=O)R^a$, —$(CH_2)_{1-2}OCO_2R^a$, —$(CH_2)_{1-2}NHR^a$, —$(CH_2)_{1-2}NR^aR^b$, —$(CH^2)_{1-2}OC(=O)NHR^a$ and —$(CH_2)_{1-2}OC(=O)NR^aR^b$.

In yet another variation, $R^6$ is —$CH_2C(=O)OR^a$, —$CH_2OC(=O)OR^a$, —$CH_2OH$, —$CH_2OAc$, —$CH_2NH(CH_3)$ and —$(CH_2)_{1-2}N(CH_3)_2$. In another variation, the number of $R_6$ groups substituted on the $R_4R_5$ ring is from 1 to 4.

In another variation, $R^7$ and $R^8$ is selected from the group consisting of hydrogen, $(C_1-C_8)$alkyl-, aryl, aryl$(C_1-C_8)$alkylene-, mono-, bicyclic- or aromatic or nonaromatic ring having 3, 4, 5, 6, 7, 8, 9 or 10 ring atoms, wherein the ring atoms are optionally interrupted by 1, 2, 3 or 4 heteroatoms selected from the group consisting of —O—, —S—, —SO—, —S(O)$_2$— or amine (—$NR^a$—) in the ring, and each is optionally substituted with from 1, 2, 3 or 4 $R^a$ groups. In yet another variation, $R^7$ is selected from the group consisting of hydrogen, methyl, ethyl, propyl, butyl, 3-pentyl, iso-propyl, iso-butyl, sec-butyl, tert-butyl, phenyl and benzyl, or wherein $R^7$ is hydrogen, methyl or sec-butyl. In another variation, $R^7$ and $R^8$ are each independently selected from the group consisting of hydrogen, $(C_1-C_8)$alkyl, $(C_3-C_8)$cycloalkyl, aryl, aryl$(C_1-C_8)$alkylene, heteroaryl and heteroaryl$(C_1-C_8)$alkylene-; or wherein $R^7$ and $R^8$ together with the nitrogen atom to which they attach form a heterocycle or heteroaromatic ring.

In one particular variation of each of the above, —$NR^7R^8$ is selected from the group consisting of amino, methylamino, dimethylamino, ethylamino, pentylamino, diphenylethylamino, pyridylmethylamino, diethylamino and benzylamino. In another variation, —$NR^7R^8$ is selected from the group consisting of amino, methylamino, dimethylamino, ethylamino, diethylamino and benzylamino, or wherein —$NR^7R^8$ is amino.

In one particular variation of each of the above; $R^a$ and $R^b$ are each independently selected from the group consisting of hydrogen, $(C_1-C_8)$alkyl and $(C_1-C_8)$alkyl substituted with 1 to 3 $(C_1-C_8)$alkoxy, $(C_3-C_8)$cycloalkyl, $(C_1-C_8)$alkylthio, aryl, aryl$(C_1-C_8)$alkylene, heteroaryl, or heteroaryl$(C_1-C_8)$ alkylene; or $R^a$ and $R^b$ together with the nitrogen to which they are attached, form a pyrrolidino, piperidino, morpholino, or thiomorpholino ring; $R^c$ is hydrogen or $(C_1-C_6)$ alkyl; m is 0 to about 8 and p is 0 to 2; and Y is —$CR^3R^4R^5$ or $NR^4R^5$.

In another variation, $R^7$ is selected from the group consisting of benzyl, phenethyl, phenylpropyl and each is optionally substituted with from 1, 2 or 3 substituents of $R^a$. In a particular variation, $R^7$ is selected from the group consisting of benzyl, phenethyl, phenylpropyl and each is optionally substituted with from 1, 2 or 3 substituents of $R^a$ selected from the group consisting of methyl, ethyl, propyl, methoxy, ethoxy and propoxy; or wherein $R^7$ is benzyl and $R^a$ is methoxy.

In another aspect of the above, $R^9$ is selected from the group consisting of hydrogen, fluoro, —OH, —$CH_2OH$, —OMe, —OAc, —$NH_2$, —NHMe, —$NMe_2$ and —NHAc; or wherein $R^9$ is hydrogen or OH. In one variation, each $R^{10}$ is independently selected from the group consisting of hydrogen, fluoro, $(C_1-C_8)$alkyl, $(C_3-C_8)$cycloalkyl, heterocyclyl, heterocycle$(C_1-C_8)$alkylene-, aryl, aryl$(C_1-C_8)$alkylene-, heteroaryl and heteroaryl$(C_1-C_8)$alkylene-. In another variation, $R^{10}$ is selected from the group consisting of hydrogen, $(C_1-C_8)$alkyl, cyclopropyl, cyclohexyl and benzyl; or wherein $R^{10}$ is hydrogen. In yet another variation of the above, $R^9$ and $R^{10}$ and the carbon atom to which they are attached is a C=O group.

In a variation of the above compound, $R^a$ and $R^b$ are each independently selected from the group consisting of hydrogen, $(C_1-C_4)$alkyl, aryl and aryl$(C_1-C_8)$alkylene. In a particular variation, $R^a$ and $R^b$ are each independently selected from the group consisting of hydrogen, methyl, ethyl, phenyl and benzyl. In another variation, $R^a$ is $(C_1-C_8)$alkyl. In yet another variation, $R^a$ is selected from the group consisting of methyl, ethyl, propyl and butyl. In yet another variation, $R^a$ is selected from the group consisting of methyl, ethyl, i-propyl, i-butyl and tert-butyl. In still another variation, $R^a$ and $R^b$ is a ring.

In one variation of each of the above, Y is —$CR_3R_4R_5$ or $NR_4R_5$, and is selected from the group consisting of:

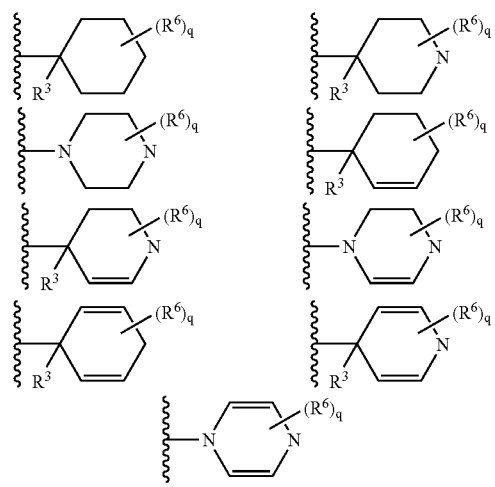

wherein q is 0, 1, 2, 3 or 4; $R^3$ is selected from the group consisting of hydrogen, halo, —$OR^a$, —$SR^a$, $(C_1-C_8)$alkyl, cyano, nitro, trifluoromethyl, trifluoromethoxy, $(C_3-C_8)$cycloalkyl, heterocycle, hetrocycle$(C_1-C_8)$alkyl, aryl, aryl $(C_1-C_8)$alkyl, heteroaryl, heteroaryl$(C_1-C_8)$alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, $R^aS(=O)_2$—, —$NNR^a$ and —$OPO_2R^a$; and each $R^6$ is independently selected from the group consisting of halo, —$OR^a$, —$SR^a$, substituted or unsubstituted $(C_1-C_8)$alkyl, cyano, nitro, trifluoromethyl, trifluoromethoxy, $(C_1-C_8)$cycloalkyl, $(C_6-C_{12})$bicycloalkyl, heterocycle, hetrocyclyl$(C_1-C_8)$alkyl, aryl, aryl$(C_1-C_8)$ alkyl, heteroaryl, heteroaryl$(C_1-C_8)$alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, —$OPO_3R^a$, $R^aOC(=S)$—, $R^aC(=S)$—, —$SSR^a$, $R^aS(=O)$—, —$NNR^a$ and —$OPO_2R^a$, provided that $R^6$ is not halogen or a heteroatom when $R^6$ is attached to a heteroatom.

In another variation, Y is —$CR^3R^4R^5$ or $NR^4R^5$ and is selected from the group consisting of:

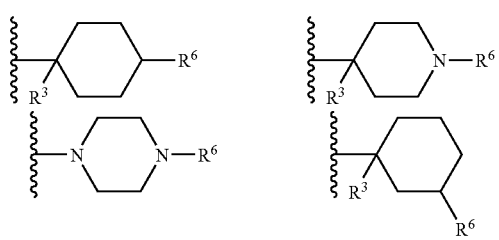

-continued

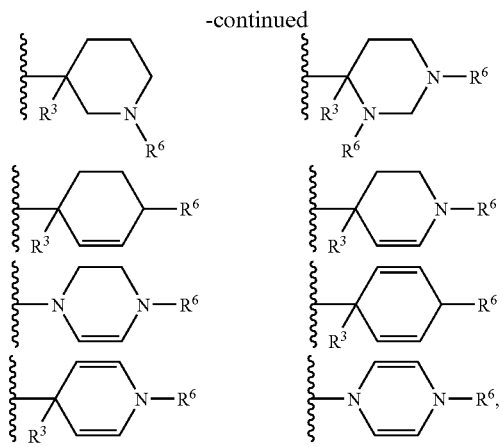

wherein R³ is selected from the group consisting of hydrogen, halo, —OR$^a$, —SR$^a$, ($C_1$–$C_8$)alkyl, cyano, nitro, trifluoromethyl, trifluoromethoxy, ($C_3$–$C_8$)cycloalkyl, heterocycle, hetrocycle($C_1$–$C_8$)alkyl, aryl, aryl($C_1$–$C_8$)alkyl, heteroaryl, heteroaryl($C_1$–$C_8$)alkyl, —$CO_2R^a$, $R^aC$(=O) O—, $R^aC$(=O)—, —$OCO_2R^a$, $R^aR^bNC$(=O)O—, $R^bOC$(=O)N($R^a$)—, $R^aR^bN$—, $R^aR^bNC$(=O)—, $R^aC$(=O)N ($R^b$)—, $R^aR^bNC$(=O)N($R^b$)—, $R^aR^bNC$(=S)N($R^b$)—, —$OPO_3R^a$, $R^aOC$(=S)—, $R^aC$(=S)—, —$SSR^a$, $R^aS$ (=O)—, $R^aS$(=O)$_2$—, —$NNR^a$ and —$OPO_2R^a$; and each $R^6$ is independently selected from the group consisting of halo, —OR$^a$, —SR$^a$, substituted or unsubstituted ($C_1$–$C_8$) alkyl, cyano, nitro, trifluoromethyl, trifluoromethoxy, ($C_1$–$C_8$)cycloalkyl, ($C_6$–$C_{12}$)bicycloalkyl, heterocycle, hetrocyclyl($C_1$–$C_8$)alkyl, aryl, aryl($C_1$–$C_8$)alkyl, heteroaryl, heteroaryl($C_1$–$C_8$)alkyl, —$CO_2R^a$, $R^aC$(=O)O—, $R^aC$ (=O)—, —$OCO_2R^a$, $R^aR^bNC$(=O)O—, $R^bOC$(=O)N ($R^a$)—, $R^aR^bN$—, $R^aR^bNC$(=O)—, $R^aC$(=O)N($R^b$)—, $R^aR^bNC$(=O)N($R^b$)—, $R^aR^bNC$(=S)N($R^b$)—, —$OPO_3R^a$, $R^aOC$(=S)—, $R^aC$(=S)—, —$SSR^a$, $R^aS$ (=O)—, —$NNR^a$ and —$OPO_2R^a$.

In another variation, the ring comprising —C($R^3$)$R^4R^5$ is 2-methylcyclohexan-1-yl, 2,2-dimethylcyclohexan-1-yl, 2-ethylcyclohexan-1-yl, 2,2-diethylcyclohexan-1-yl, 2-tert-butylcyclohexan-1-yl, 2-phenylcyclohexan-1-yl, 3-methylcyclohexan-1-yl, 3-ethylcyclohexan-1-yl, 3,3-dimethylcyclohexan-1-yl, 4-methylcyclohexan-1-yl, 4-ethylcyclohexan-1-yl, 4,4-dimethylcyclohexan-1-yl, 4-tert-butylcyclohexan-1-yl, 4-phenylcyclohexan-1-yl, 3,3,5,5-tetramethylcyclohexan-1-yl, 2,4-dimethylcyclopentan-1-yl, 4-(carboxyl)cyclohexan-1-yl, 4-(carboxymethyl)cyclohexan-1-yl and 4-(carboxyethyl)cyclohexan-1-yl. In yet another variation, the ring comprises —($R^3$)$R^4R^5$ is piperidin-4-yl, 1-carboxypiperiden-4-yl, 1-(methoxycarbonyl)piperidin-4-yl, 1-(ethoxycarbonyl)piperidin-4-yl, 1-(n-propoxycarbonyl)piperidin-4-yl, 1-(2,2-dimethylpropoxycarbonyl)piperidin-4-yl, piperidin-1-yl, 4-carboxypiperiden-1-yl, 4-(methoxycarbonyl)piperidine-1-yl, 4-(ethoxycarbonyl)piperidine-1-yl, 4-(n-propoxy)piperidine-1-yl, 4-(2,2-dimethylpropoxycarbonyl)piperidine-1-yl, piperidin-3-yl, 1-carboxypiperidene-3-yl, 1-(methoxycarbonyl)piperidine-3-yl, 1-(ethoxycarbonyl)piperidine-3-yl, 1-(n-propoxycarbonyl)piperidine-3-yl, 1-(2,2-dimethylpropoxycarbonyl)piperidine-3-yl, 3-carboxypiperidene-1-yl, 3-(methoxycarbonyl)piperidine-1-yl, 3-(ethoxycarbonyl)piperidine-1-yl, 3-(n-propoxycarbonyl)piperidine-1-yl, 3-(2,2-dimethylpropoxycarbonyl)piperidine-1-yl, piperazin-1-yl, 1-caboxypiperazin-4-yl, 1-(methoxycarbonyl)piperazin-4-yl, 1-(ethoxycarbonyl)piperazin-4-yl and 1-(n-propoxycarbonyl)piperazin-4-yl.

In another variation, the ring comprising —C($R^3$)$R^4R^5$ is selected from the group consisting of 2-methylcyclohexan-1-yl, 2,2-dimethylcyclohexan-1-yl, 2-ethylcyclohexan-1-yl, 2,2-diethylcyclohexan-1-yl, 2-tert-butylcyclohexan-1-yl, 2-phenylcyclohexan-1-yl, 3-methylcyclohexan-1-yl, 3-ethylcyclohexan-1-yl, 3,3-dimethylcyclohexan-1-yl, 4-methylcyclohexan-1-yl, 4-ethylcyclohexan-1-yl, 4,4-dimethylcyclohexan-1-yl, 4-tert-butylcyclohexan-1-yl, 4-phenylcyclohexan-1-yl, 3,3,5,5-tetramethylcyclohexan-1-yl, 2,4-dimethylcyclopentan-1-yl, 4-(carboxyl)cyclohexan-1-yl, 4-(carboxymethyl)cyclohexan-1-yl, 4-(carboxyethyl)cyclohexan-1-yl, piperidin-4-yl, 1-(methoxycarbonyl)piperidin-4-yl, 1-(2,2-dimethylpropoxycarbonyl)piperidin-4-yl, piperidin-1-yl, 4-(methoxycarbonyl)piperidine-1-yl, 4-(2,2-dimethylpropoxycarbonyl)piperidine-1-yl, piperidin-3-yl, 1-(methoxycarbonyl)piperidine-3-yl, 1-(2,2-dimethylpropoxycarbonyl)piperidine-3-yl, 3-(methoxycarbonyl)piperidine-1-yl and 3-(2,2-dimethylpropoxycarbonyl)piperidine-1-yl.

In a particular variation, Z is a mono-, bicyclic-, tricyclic- or aromatic or non-aromatic ($C_3$–$C_{20}$)cycloalkyl ring, wherein the ring atoms are optionally interrupted by 1–8 heteroatoms selected from the group consisting of —O—, —S—, —SO—, —S(O)$_2$— and amino (—NR$^a$—). In one variation of the above, $R^1$ and $R^2$ are hydrogen, m is 0, 1, 2 or 3 and Z is selected from the group consisting of furan, dihydro-furan, tetrahydrofuran, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with from 1 to 10 $R^a$ groups. In another variation, Z is a mono-, bicyclic—, tricyclic- or aromatic or non-aromatic ($C_3$–$C_{20}$)cycloalkyl ring, wherein the ring atoms are optionally interrupted by 1–8 heteroatoms selected from the group consisting of —O—, —S—, —SO—, —S(O)$_2$— and amino (—NR$^a$—).

In a particular variation, $R^1$ and $R^2$ are hydrogen, m is 0, 1, 2 or 3 and Z is selected from the group consisting of furan, dihydro-furan, tetrahydrofuran, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with from 1 to 10 $R^a$ groups.

In another aspect, there is provided a compound of the formula:

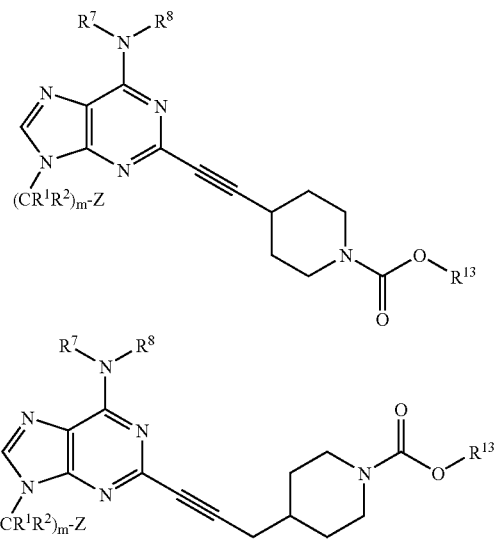

wherein R⁷ and R⁸ are each independently selected from the group consisting of hydrogen, $(C_2-C_4)$alkyl, 3-pentyl, aryl $(C_2-C_4)$alkyl, heteroaryl$(C_2-C_4)$alkyl, each unsubstituted or substituted, R⁸ is selected from the group consisting of hydrogen or $(C_1-C_4)$alkyl; and R¹¹ is selected from the group consisting of $(C_1-C_4)$alkyl, propargyl, $(C_3-C_6)$cycloalkyl, $(C_3-C_6)$cycloalkyl$(C_1-C_4)$alkyl, aryl$(C_1-C_4)$alkyl, heteroaryl$(C_1-C_4)$alkyl, heterocyclyl$(C_1-C_4)$alkyl, HO$(C_1-C_4)$alkyl, halo$(C_1-C_4)$alkyl, —COO$(C_1-C_4)$alkyl, $(C_1-C_4)$alkylCOO$(C_1-C_4)$alkyl, each unsubstituted or substituted; R¹³ is methyl, iso-propyl, iso-butyl, or tert-butyl; and R¹, R² and m are as defined herein; or a pharmaceutically acceptable salt thereof, optionally in the form of a single stereoisomer or mixture of stereoisomers thereof.

In another aspect, there is provided a pharmaceutical composition comprising a therapeutically effective amount of a compound of each of the above, and a pharmaceutically acceptable excipient. Some of the compounds of formulae I, II, and III may further form pharmaceutically acceptable salts and esters. All of these forms are included within the scope of the present invention. Pharmaceutically acceptable base addition salts of the compounds of formulae I, II, and III include salts which may be formed when acidic protons present in the parent compound are capable of reacting with inorganic or organic bases as known in the art. Acceptable inorganic bases, include for example, aluminum hydroxide, calcium hydroxide, potassium hydroxide, sodium carbonate and sodium-hydroxide. Salts may also be prepared using organic bases, such as choline, dicyclohexylamine, ethylenediamine, ethanolamine, diethanolamine, triethanolamine, procaine, N-methylglucamine, and the like [see, for example, Berge et al., "Pharmaceutical Salts," *J. Pharma. Sci.* 66:1 (1977)]. Pharmaceutically acceptable acid addition salts of the compounds of formulae I, II, and III include salts which may be formed when the parent compound contains a basic group. Acid addition salts of the compounds may be prepared in a suitable solvent from the parent compound and an excess of a non-toxic inorganic acid, such as hydrochloric acid, hydrobromic acid, sulfuric acid (giving the sulfate and bisulfate salts), nitric acid, phosphoric acid and the like, or a non-toxic organic acid such as aceticacid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, camphorsulfonic acid, tert-butylacetic acid, laurylsulfuric acid, glucuronic acid, glutamic acid, and the like. The free base form may be regenerated by contacting the acid addition salt with a base and isolating the free base in the conventional manner. The free base forms can differ from their respective salt forms somewhat in certain physical properties such as solubility in polar solvents.

Also included in the above embodiments, aspects and variations are salts of amino acids such as arginate and the like, gluconate, and galacturonate. Some of the compounds of the invention may form inner salts or Zwitterions. Certain of the compounds of the present invention can exist in unsolvated forms as well as solvated forms, including hydrated forms, and are intended to be within the scope of the present invention. Certain of the above compounds may also exist in one or more solid or crystalline phases or polymorphs, the variable biological activities of such polymorphs or mixtures of such polymorphs are also included in the scope of this invention. Also provided are pharmaceutical compositions comprising pharmaceutically acceptable excipients and a therapeutically effective amount of at least one compound of this invention.

Pharmaceutical compositions of the compounds of this invention, or derivatives thereof, may be formulated as solutions or lyophilized powders for parenteral administration. Powders may be reconstituted by addition of a suitable diluent or other pharmaceutically acceptable carrier prior to use. The liquid formulation is generally a buffered, isotonic, aqueous solution. Examples of suitable diluents are normal isotonic saline solution, 5% dextrose in water or buffered sodium or ammonium acetate solution. Such formulations are especially suitable for parenteral administration but may also be used for oral administration. Excipients, such as polyvinylpyrrolidinone, gelatin, hydroxycellulose, acacia, polyethylene glycol, mannitol, sodium chloride, or sodium citrate, may also be added. Alternatively, these compounds may be encapsulated, tableted, or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols, or water. Solid carriers include starch, lactose, calcium sulfate, dihydrate, terra alba, magnesium stearate or stearic acid, talc, pectin, acacia, agar, or gelatin. The carrier may also include a sustained release material such as glyceryl monostearate or glyceryl distearate, alone or with a wax. The amount of solid carrier varies but, preferably, will be between about 20 mg to about 1 g per dosage unit. The pharmaceutical preparations are made following the conventional techniques of pharmacy involving milling, mixing, granulation, and compressing, when necessary, for tablet forms; or milling, mixing, and filling for hard gelatin capsule forms. When a liquid carrier is used, the preparation will be in the form of a syrup, elixir, emulsion, or an aqueous or non-aqueous suspension. Such a liquid formulation may be administered directly p.o. or filled into a soft gelatin capsule. Suitable formulations for each of these methods of administration may be found in, for example, *Remington: The Science and Practice of Pharmacy*, A. Gennaro, ed., 20th edition, Lippincott, Williams & Wilkins, Philadelphia, Pa.

In one variation, there is provided the above compound, or a pharmaceutically acceptable salt thereof, optionally in the form of a single stereoisomer or mixture of stereoisomers thereof. In one aspect, there is provided a method for stimulating motor activity without dyskinesia in a mammal, comprising administering a therapeutically effective amount of an $A_{2A}$ anatagonist compound of the above to the mammal in need of such treatment. In one variation of the above method, the therapeutically effective amount is effective to treat ischemia, brain damage induced by ischemia and excitoxicity, Huntington disease, catalepsy, cancer, drug addiction and withdrawal, Parkinson's disease (drug induced, post-encephalitic, poison induced or post-traumatic induced), acute or chronic pain, narcolepsy and Alzheimer's disease. In another variation of the above, the therapeutically effective amount is effective to stimulate motor activity for treating a movement disorder, where the disorder is progressive supernuclear palsy, Huntington's disease, multiple system atrophy, corticobasal degeneration, Wilsons disease, Hallerrorden-Spatz disease, progressive pallidal atrophy, Dopa-responsive dystonia-Parkinsonism, spasticity or other disoders of the basal ganglia which result in dyskinesias. In another variation of the above, the compound is used in combination with one or more additional drugs in the treatment of movement disorders (i.e. L-DOPA or dopamine agonist), addiction, or cancer with the components being in the same formulation or in a separate formulation for administration simultaneously or sequentially. In yet another variation of the method, the therapeutically effective amount is effective to provide neuroprotection and slow or halt the degeneration of dopaminergic neurons. In yet another variation, the therapeutically effective amount is effective to enhance the immune response by increasing the activity of an immune cell in a mammal. In one variation, the activity is pro-inflammatory cytokine production. In another variation, the activity of the immune cell results in an increase in inflammation. In yet another variation of the above method, the mammal is human.

In another embodiment of the invention, there is provided a method for stimulating motor activity without dyskinesia in a mammal, comprising administering a therapeutically effective amount of an $A_{2A}$ antagonist compound of the above to the mammal in need of such treatment. In one variation of the above embodiment, there is provided a method as described above wherein the $A_{2A}$ antagonist is selected from a compound of each of the above embodiments, aspects and variations.

In another embodiment, there is provided a method to evaluate novel $A_{2A}$ antagonists in four mouse models of PD. These include: A) motor function in normal and dopamine-depleted mice; B) synergistic activity with L-dopa to stimulate motor activity in dopamine-depleted mice; C) attenuation MPTP-induced neurotoxicity by inhibiting MPTP metabolism; and D) delayed L-dopa-induced locomotor sensitization in unilateral 6-OHDA-lesioned mice.

In another embodiment, there is provided a method comprising contacting a compound of each of the above formula with an isotope such as those from hydrogen, carbon, nitrogen, oxygen, phosphorous, fluorine, chlorine, or iodine (e.g. $^2H$, $^3H$, $^{13}C$, $^{14}C$, $^{15}N$, $^{18}O$, $^{31}P$, $^{32}P$, $^{35}S$, $^{18}F$, $^{36}Cl$, $^{123}I$, $^{125}I$) optionally being a radioactive isotope (radionuclide), such as, for example, tritium, radioactive iodine (for example, $^{125}I$ for binding assays or $^{123}I$ for Spect Imaging) or other non-radioactive isotope (such as deuterium) and the like. Isotopically labeled compounds may be useful for drug/tissue distribution assays and/or manipulating oxidative metabolism via the primary kinetic isotope effect. They are also valuable in identifying potential therapeutic agents for the treatment of diseases or conditions associated with target-receptor mediation, by contacting said agents with said radioligands and receptors, and measuring the extent of displacement of the radioligand and/or binding of the agent. Representative references for Deuterium-for hydrogen substitution include Hanzlik et al., *J. Org. Chem.* 55, 3992–3997, 1990; Reider et al., *J. Org. Chem.* 52, 3326–3334, 1987; Foster, *Adv. Drug Res.* 14 1–40, 1985; Gillette et al., *Biochemistry* 33(10)2927–2937, 1994; and Jarman et al. *Carcinogenesis* 16(4) 683–688, 1993, the references of which are incorporated herein in their entirety. The use of radiolabelled compounds that may be detected using imaging techniques, such as, for instance, Single Photon Emission Computerized Tomography (SPECT) or Positron Emission Tomography (PET) and the like, are known in the art. See for example, U.S. Pat. Nos. 6,395,742; 6,472,667 and references cited therein.

DETAILED DESCRIPTION OF THE INVENTION

Definitions

Figure 1:
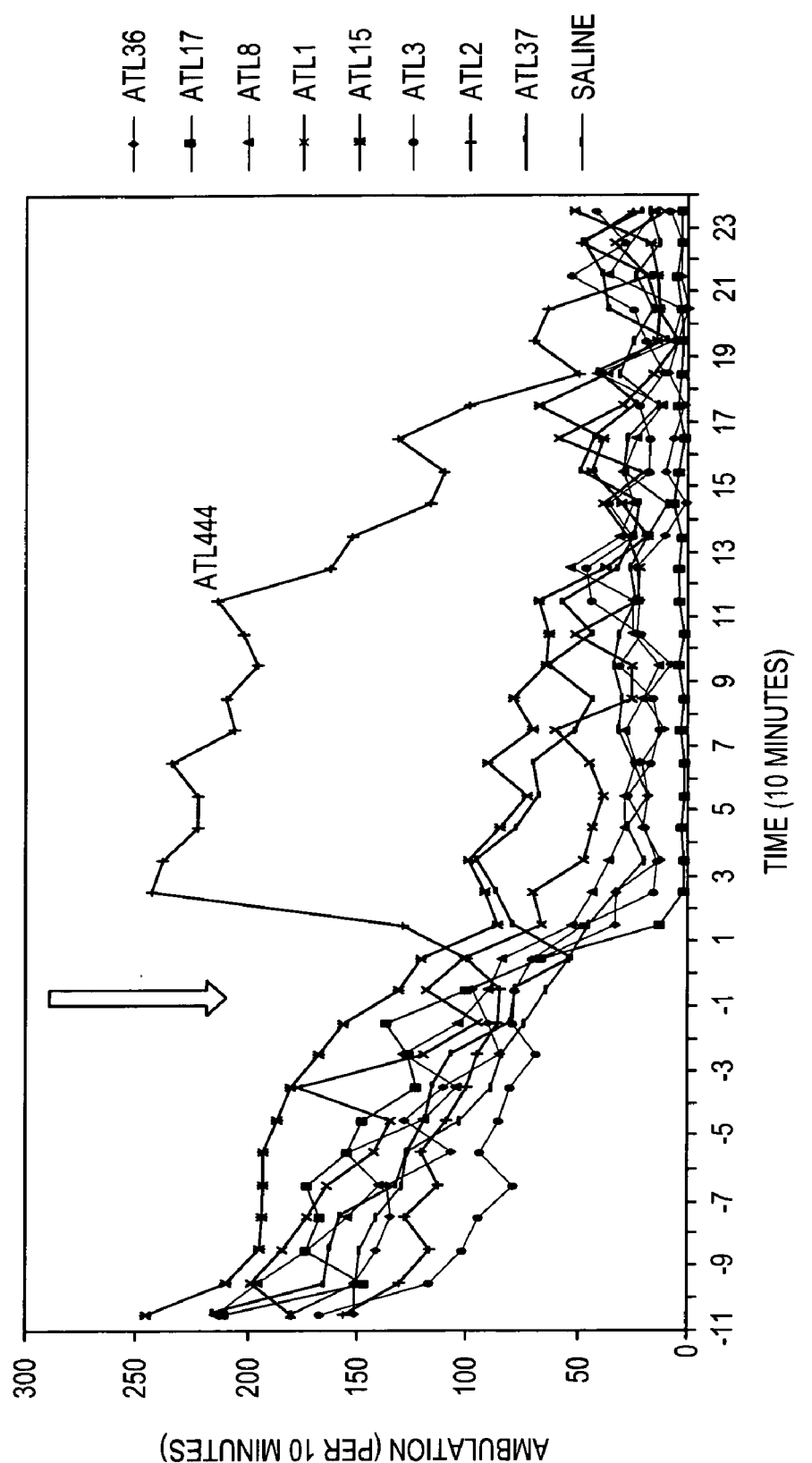
FIG. 1 shows locomotor stimulant activity of $A_{2A}AR$ antagonists injected into mice.

Unless specifically noted otherwise herein, the definition of the terms used are standard definitions used in the art of organic synthesis and pharmaceutical sciences.

Where a carbonyl group or a carbonyl derivative such as a thio carbonyl or an imine and the like, is represented by a group such as —C(=O)O— or —C(=O)NR$^a$—, for example, it is intended that the corresponding isomeric group that is —OC(=O)— or —NR$^a$C(=O)— is also included.

An "alkyl" group is a straight, branched, saturated or unsaturated, aliphatic group having a chain of carbon atoms, optionally with oxygen, nitrogen or sulfur atoms inserted between the carbon atoms in the chain or as indicated. A $(C_1-C_{20})$alkyl, for example, includes alkyl groups that have a chain of between 1 and 20 carbon atoms, and include, for example, the groups methyl, ethyl, propyl, isopropyl, vinyl, allyl, 1-propenyl, isopropenyl, ethynyl, 1-propynyl, 2-propynyl, 1,3-butadienyl, penta-1,3-dienyl, penta-1,4-dienyl, hexa-1,3-dienyl, hexa-1,3,5-trienyl, and the like. An alkyl group may also be represented, for example, as a —(CR$^1$R$^2$)$_m$— group where R$^1$ and R$^2$ are independently hydrogen or are independently absent, and for example, m is 1 to 8, and such representation is also intended to cover both saturated and unsaturated alkyl groups. An alkyl as noted with another group such as an aryl group, represented as "arylalkyl" for example, is intended to be a straight, branched, saturated or unsaturated aliphatic divalent group with the number of atoms indicated in the alkyl group (as in $(C_1-C_{20})$alkyl, for example) and/or aryl group (as in $(C_5-C_{14})$aryl, for example) or when no atoms are indicated means a bond between the aryl and the alkyl group. Non-exclusive examples of such group include benzyl, phenethyl and the like.

An "alkylene" group is a straight, branched, saturated or unsaturated aliphatic divalent group with the number of atoms indicated in the alkyl group (as in —$(C_1-C_{20})$alkylene- or —$(C_1-C_{20})$alkylenyl-, for example), optionally with one or more oxygen, nitrogen or sulfur atoms inserted (or "interrupted") between the carbon atoms in the chain or as indicated.

A "cyclyl" such as a monocyclyl or polycyclyl group includes monocyclic, or linearly fused, angularly fused or bridged polycycloalkyl, or combinations thereof. Such cyclyl group is intended to include the heterocyclyl analogs. A cyclyl group may be saturated, partically saturated or aromatic.

"Halogen" or "halo" means fluorine, chlorine, bromine or iodine.

A "heterocyclyl" or "heterocycle" is a cycloalkyl wherein one or more of the atoms forming the ring is a heteroatom that is a N, O, or S. Non-exclusive examples of heterocyclyl include piperidyl, 4-morpholyl, 4-piperazinyl, pyrrolidinyl, 1,4-diazaperhydroepinyl, 1,3-dioxanyl, and the like.

"Pharmaceutically acceptable salts" means salt compositions that is generally considered to have the desired pharmacological activity, is considered to be safe, non-toxic and is acceptable for veterinary and human pharmaceutical applications. Such salts include acid addition salts formed with inorganic acids such as hydrochloric acid, hydrobromic acid, sulfuric acid, phosphoric acid, and the like; or with organic acids such as acetic acid, propionic acid, hexanoic acid, malonic acid, succinic acid, malic acid, citric acid, gluconic acid, salicylic acid and the like.

"Substituted or unsubstituted" means that a group such as, for example, alkyl, aryl, heterocyclyl, $(C_1-C_8)$cycloalkyl, $(C_6-C_{12})$bicycloalkyl, hetrocyclyl$(C_1-C_8)$alkyl, aryl$(C_1-C_8)$alkyl, heteroaryl, heteroaryl$(C_1-C_8)$alkyl, the mono-, bi- or polycyclic rings that define the Z group, and the like, unless specifically noted otherwise, may be unsubstituted or, may substituted by 1, 2, 3, 4 or 5 substitutents selected from the group such as halo, nitro, trifluoromethyl, trifluoromethoxy, methoxy, carboxy, —$NH_2$, —OH, —SH, —$NHCH_3$, —$N(CH_3)_2$, —SMe, propargyl, cyano, —NNH, —$NNCH_3$, —$OPO_2H$, —$OPO_2CH_3$, —$S(SO_2)H$, —$S(SO_2)OH$, —$S(SO_2)CH_3$ and —$S(SO_2)OCH_3$, and the like.

Representative $A_{2A}AR$ Antagonists

TABLE 1

Binding Affinity and Selectivity of $A_{2A}AR$ Ligands[a]

| ATL # | $R^{12}$ | $R^7$ | $(CR^1R^2)_m$-Z | $A_1AR$ | $A_{2A}AR$ | $A_{2B}AR$ | $A_3AR$ |
|---|---|---|---|---|---|---|---|
| Antagonists | | | | | | | |
| 11 | A | 3-P | Me | 172 (1.3) | 137 | 20% | 30% |
| 17 | A | 3-P | Proparg | 11 (2) | 5 | 147 (29) | 188 (38) |
| 2 | A | $NH_2$ | Proparg | 4.6 (5) | 0.95 | 50 (11) | 599 (630) |
| 3 | A | $NH_2$ | cPent | 368 (37) | 10 | 357 (36) | 633 (63) |
| 51 | B | $NH_2$ | Proparg | 25 (16) | 1.6 | 155 (97) | >650 (>400) |
| 50 | B | $NH_2$ | cPent | >325 (>27) | 12 | 40% | 40% |

[a]Abbreviations: 3-P, 3-pentyl; Me, methyl; Proparg, prop-2-ynyl; cPent, cyclopentyl. Numbers in parentheses are selectivity ratios vs. the $A_{2A}AR$. Activities expressed as percentage are displacement of radioligand by 1 μM candidate ligand.

Motor Enhancement by the Lipophilic $A_{2A}$ Receptor Antagonist ATL-2 in Normal Mice The ability of compounds to stimulate motor activity in normal mice was measured using a simple, computer-assisted locomotor activity cage system. C57BL/6 mice (n=6–8 purchased from the Jackson's lab) were habituated for the testing environment for 120 minute prior to drug treatment. The test compounds were dissolved in vehicle (10% DMSO, 10% castrol oil EL-620 and 80% saline). The drug was administrated intraperitoneally at a dose of 15 mg/kg, and locomotor activity was recorded for 2 hours before and after drug administration.

FIG. 1 shows that ATL-2 produced strong motor stimulation, reaching peak within 20 minutes and lasting for about 60 minutes (arrow marks the injection). From our previous experience with other $A_{2A}R$ antagonists, the motor stimulant effect of ATL2 is comparable or stronger than other $A_{2A}R$ antagonists such as SCH58261 and KW6002.

Absence of Motor Stimulant Effect of ATL-2 in Mice Lacking the $A_{2A}$ Receptor We validated that ATL-2 acts on the $A_{2A}$ receptor to stimulate motor activity by using $A_2AR$ KO mice (in both mixed (129sv X C57BL/6) as well as congenic (C57BL/6 genetic background) developed over the last several years. We evaluated the motor stimulant effect of ATL-2 in $A_{2A}$ receptor KO and their WT littermates. WT and $A_{2A}$ KO mice (n=4) were habituated for 60 minutes and treated with ATL-2 (15 mg/kg) and recorded for motor activity for 120 minutes.

Figure 2:
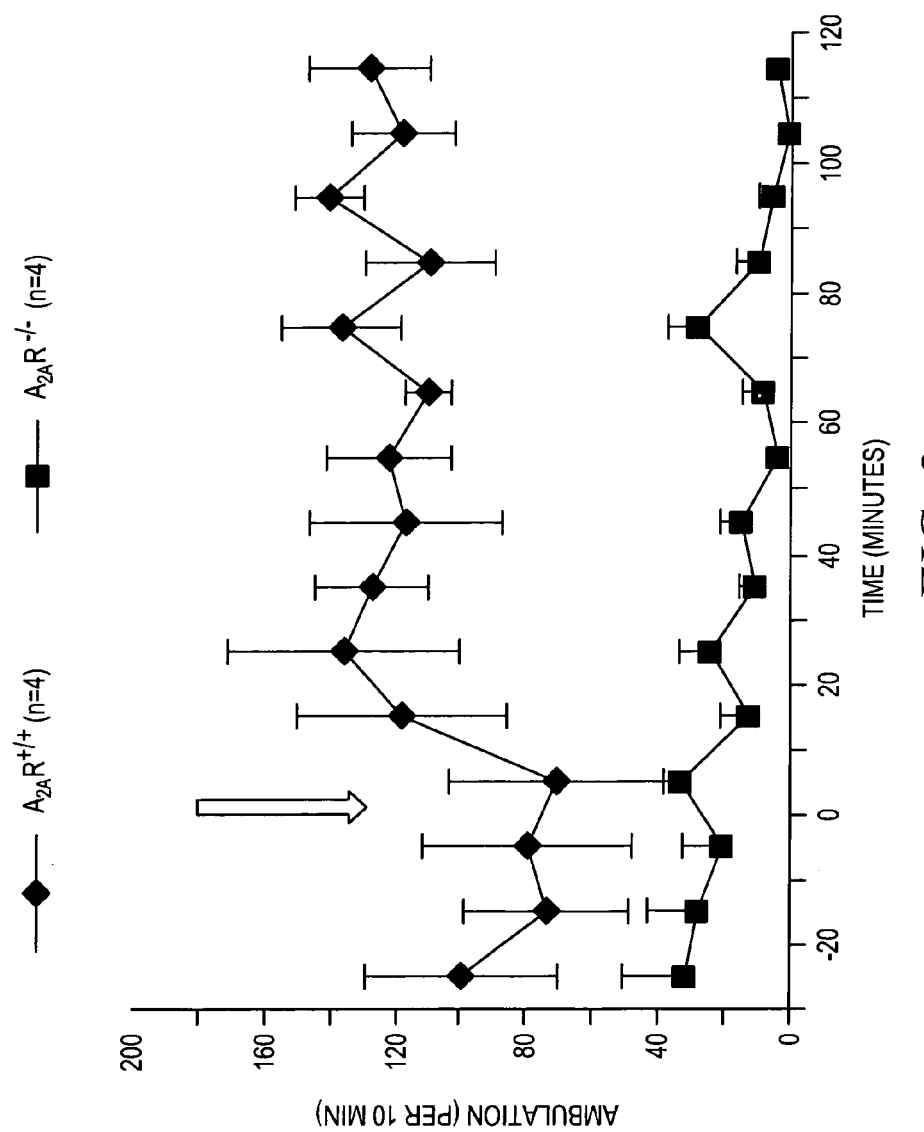
FIG. 2 shows the effect of $A_{2A}AR$ gene deletion on locomotor effect of ATL-2.

FIG. 2 shows that ATL-2 produced motor activity in WT mice (relatively high basal locomotion is likely due to short habituation time (60 minute instead of 120 minutes) and demonstrates relatively higher basal locomotion in WT compared to KO mice as we noted previously,[35] but this motor stimulation was absent in $A_{2A}$ receptor KO mice.

Experimental

Synthesis of $A_{2A}AR$ Antagonists

The following procedures may be employed for the preparation of the compounds of the present invention. The starting materials and reagents used in preparing these compounds are either available from commercial suppliers such as the Aldrich Chemical Company (Milwaukee, Wis.), Bachem (Torrance, Calif.), Sigma (St. Louis, Mo.), or are prepared by methods well known to a person of ordinary skill in the art, following procedures described in such references as *Fieser and Fieser's Reagents for Organic Synthesis*, vols. 1–17, John Wiley and Sons, New York, N.Y., 1991; *Rodd's Chemistry of Carbon Compounds*, vols. 1–5 and supps., Elsevier Science Publishers, 1989; *Organic Reactions*, vols. 1–40, John Wiley and Sons, New York, N.Y., 1991; March J.: *Advanced Organic Chemistry*, 4th ed., John Wiley and Sons, New York, N.Y.; and Larock: *Comprehensive Organic Transformations*, VCH Publishers, New York, 1989. In some cases, protective groups may be introduced and finally removed. Suitable protective groups for amino, hydroxy, and carboxy groups are described in Greene et al., *Protective Groups in Organic Synthesis*, Second Edition, John Wiley and Sons, New York, 1991. Standard organic chemical reactions can be achieved by using a number of different reagents, for examples, as described in Larock: *Comprehensive Organic Transformations*, VCH Publishers, New York, 1989.

In one variation, the compounds of this invention can be synthesized by the steps outlined in Scheme 1. Guanosine, A', is acetylated to protect the ribose during reductive chlorination by $POCl_3$/diethylaniline to form 6-chloroguanosine, C'. Non-aqueous diazotization in the presence of elemental iodine in diiodomethane is a standard route to the protected 6-chloro-2-iodonebularine, D'. Heating in methanolic ammonia deprotects the sugar and displaces the 6-chloro substituent to form 2-iodoadenosine, E'. Palladium-catalyzed coupling of E' with a terminal alkyne generates 2-alkynyladenosine F', which undergoes acid hydrolysis to form 9H-adenine G'. Alkylation with an appropriate halide (alkyl, cycloalkyl or heterocyclic) completes the synthesis of target 2,9-disubstituted adenine H'.

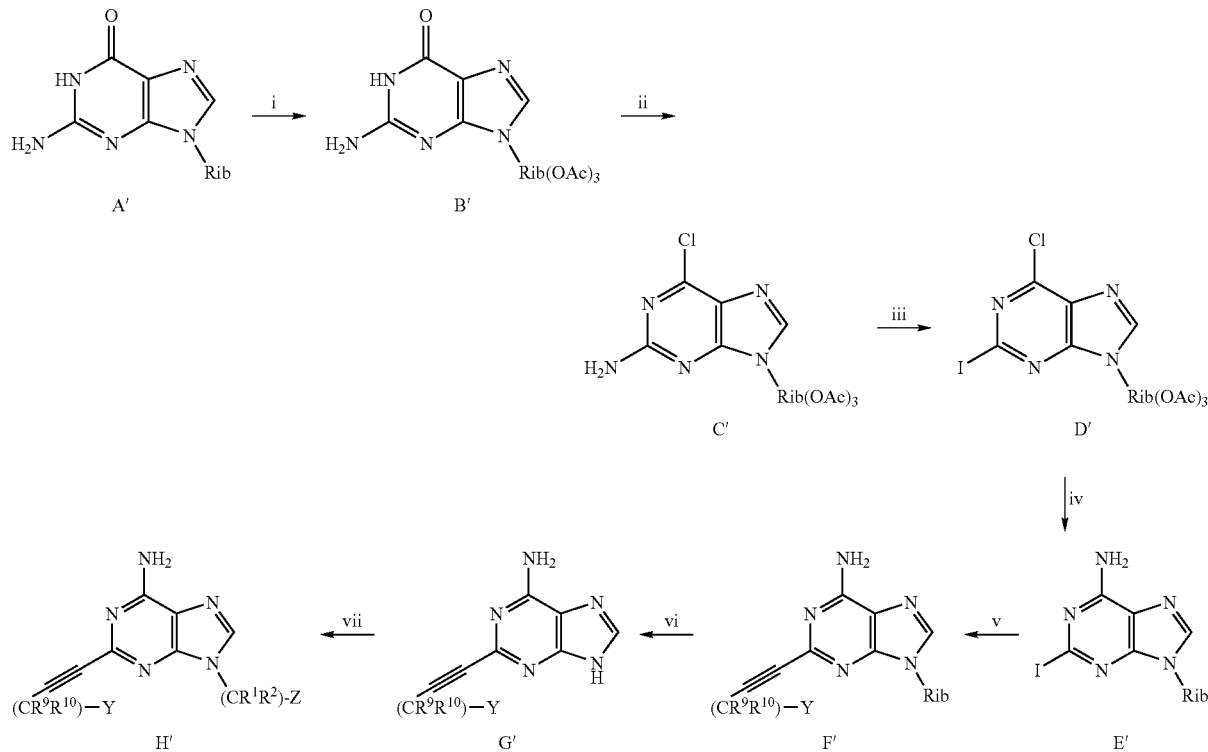

Scheme 1.

i, $Ac_2O$/Pyd; ii, $POCl_3$/PhNMe$_2$; iii, $I_2$/CH$_2$I$_2$/CuI/RONO; iv, NH$_3$; v, (CR$^9$R$^{10}$)—YCCH/Pd(PPh$_3$)$_4$/CuI; vi, H$^+$; vii, (CR$^1$R$^2$)—ZX/K$_2$CO$_3$.

Preparation of the terminal alkynes (S)-1-ethynyl-1-hydroxy-(R)-3-methylcyclohexane and 2-ethynyladamantan-2-ol is achieved by treatment of the corresponding ketone with ethynylmagnesium bromide.

Preparation of the substituted piperidine-carboxylate terminal alkynes (Scheme 2) starts with 4-carboxypiperidine (isonipecotic acid) I' in anticipation of acylating the methyl ester, J', with the appropriate alkyl chloroformate to form the N-carbamoyl ester K'. Borohydride reduction of the ester generates the 4-hydroxymethylpiperidine, L', which undergoes tosylation to M' in preparation for condensation with lithium acetylide to form terminal alkyne N'.

Scheme 2. Synthesis of terminal alkynes

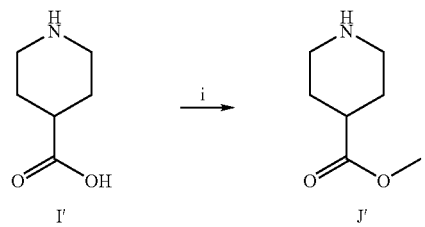

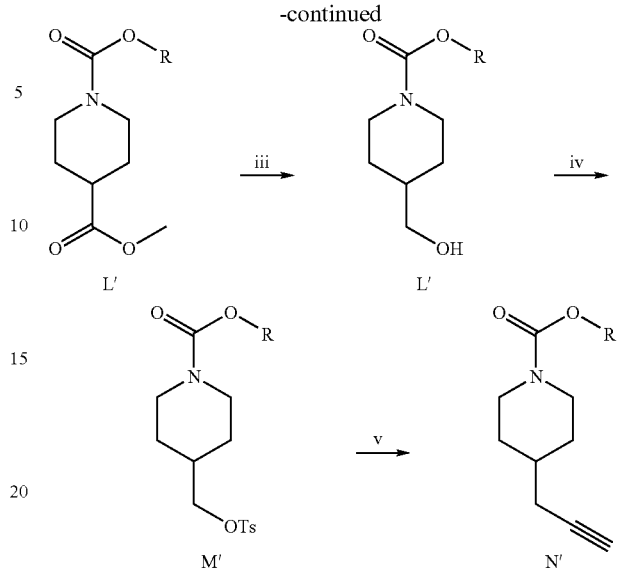

i, MeOH, H$^+$; ii, ClCOOR/base; iii, NaBH$_4$; iv, TsOCl/base; v, LiCCR$_2$.

Scheme 3:
Representative Processes for the Preparation of
A2a Antagonists and Examples of A2a Antagonists:

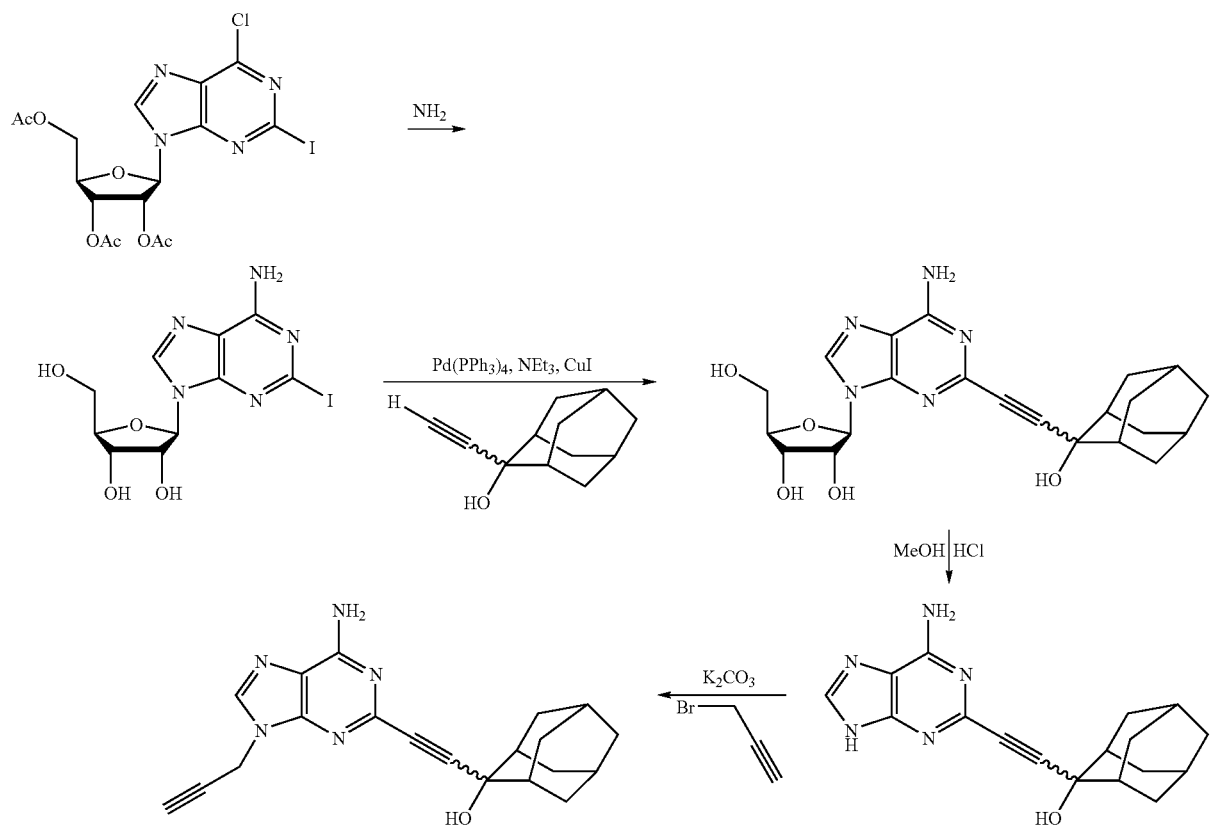

-continued
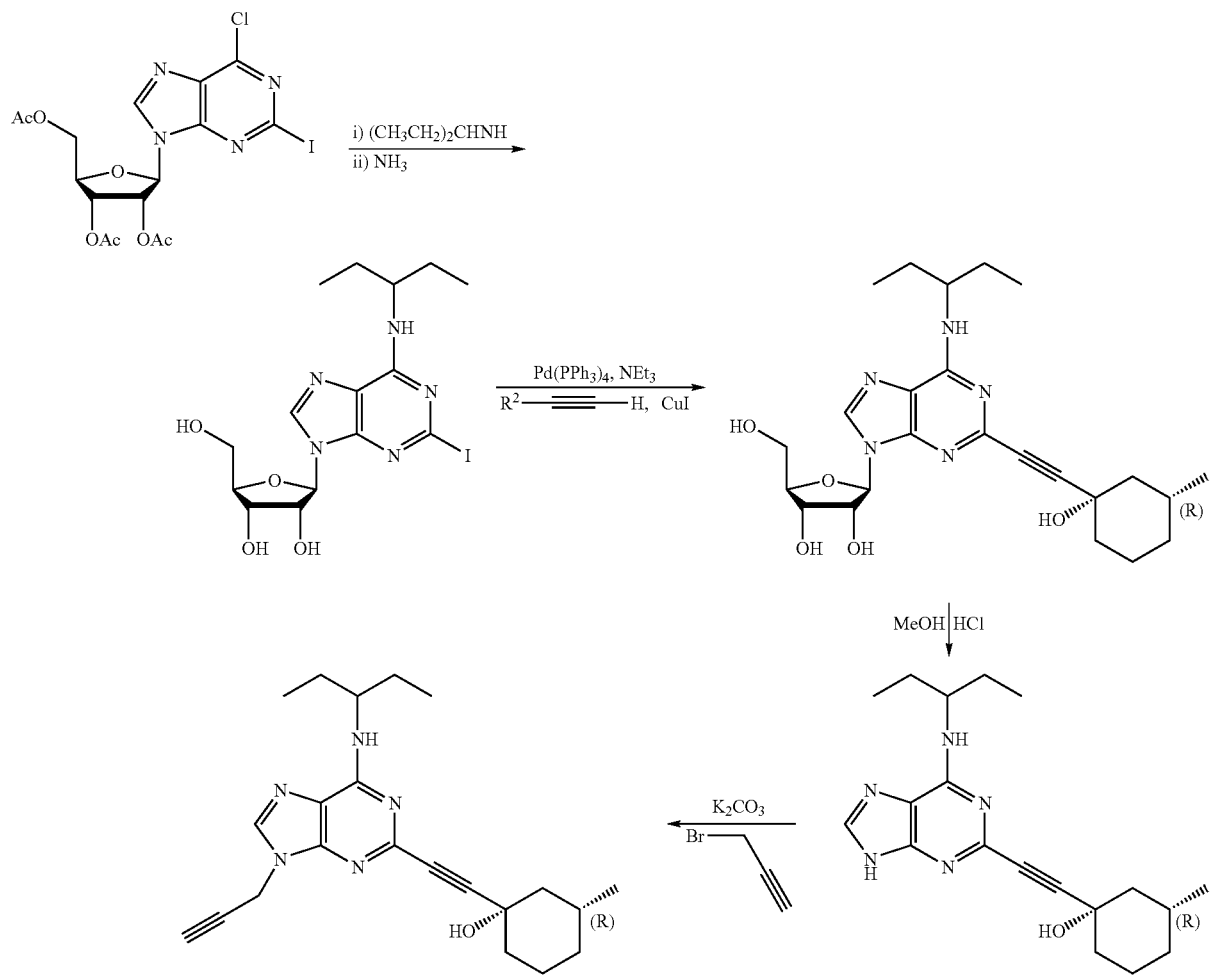
Scheme 4: Representative Processes for the Preparation of A2a Antagonists
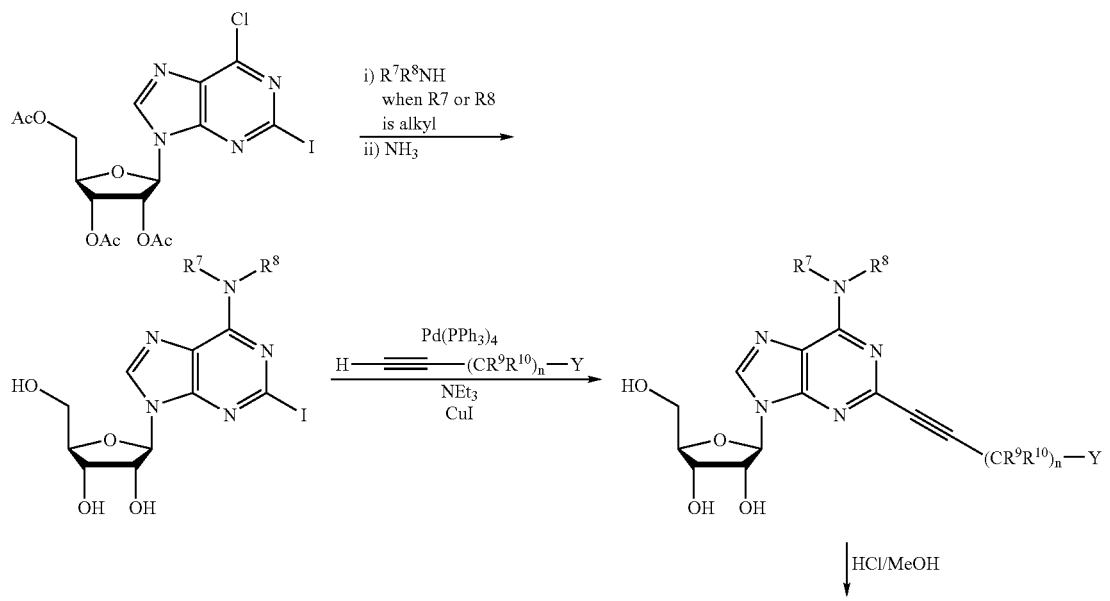

-continued
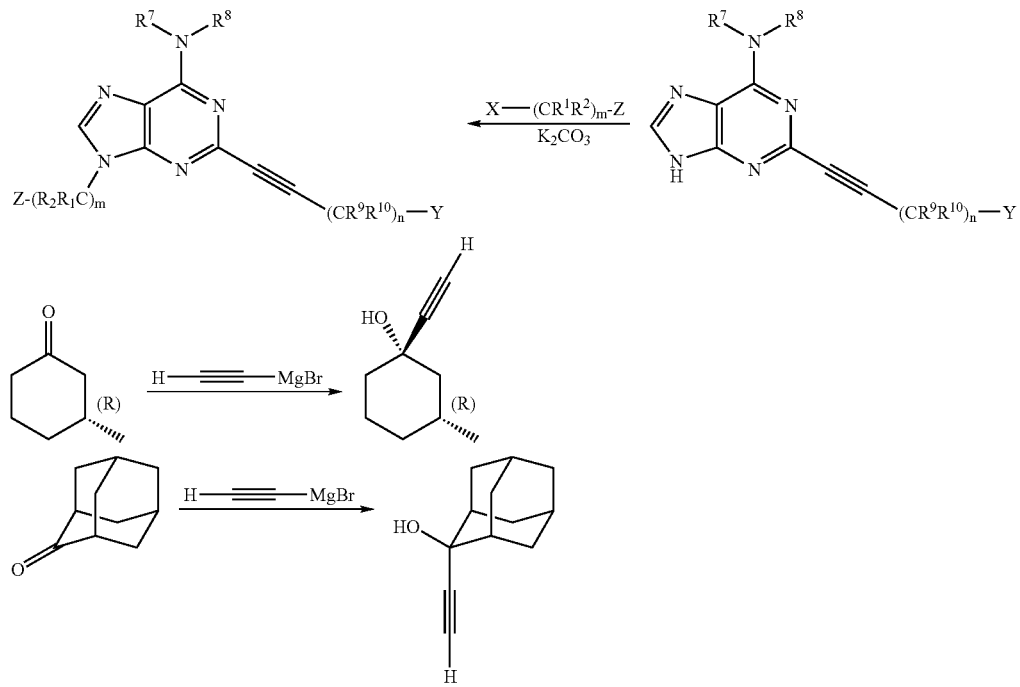
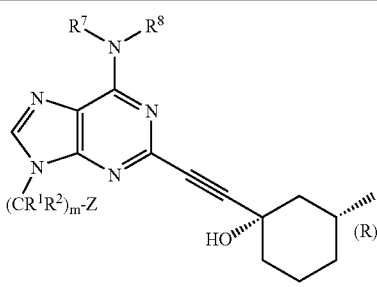
| Compound No. | R[7] | R[8] | $(CR^1R^2)_m$-Z | Human K$_i$ (nM) |
|---|---|---|---|---|
| 1 | H | H | cyclopropylmethyl | ++++ |
| 2 | H | H | Propargyl | ++++ |
| 3 | H | H | Cyclopentyl | ++++ |
| 4 | H | H | —CH$_2$CN | ++++ |
| 5 | H | H | 4-Methoxybenzyl | |
| 6 | H | H | 3,4-Dichlorobenzyl | |
| 7 | H | H | 4-(Trifluoromethyl)benzyl | |
| 8 | H | H | 3,5-dimethylisoxazol-4-ylmethyl | ++++ |
| 9 | H | H | 2-(4-trifluoromethylphenyl)thiazol-4-ylmethyl | |

-continued
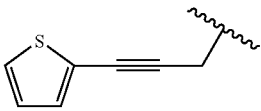
| Compound No. | R⁷ | R⁸ | (CR¹R²)ₘ-Z | Human $K_i$ (nM) |
|---|---|---|---|---|
| 10 | H | H | 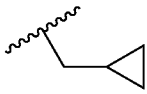 | +++ |
| 11 | Pent-3-yl | H | —CH₃ | +++ |
| 12 | Pent-3-yl | H | —CH₂CH₂CH₃ | ++++ |
| 13 | Pent-3-yl | H | Iso-propyl | +++ |
| 14 | Pent-3-yl | H | 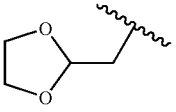 | ++++ |
| 15 | Pent-3-yl | H | Cyclopentyl | ++++ |
| 16 | Pent-3-yl | H | Allyl | ++++ |
| 17 | Pent-3-yl | H | Propargyl | ++++ |
| 18 | Pent-3-yl | H | —(CH₂)₃C≡CH | ++++ |
| 19 | Pent-3-yl | H | —CH₂CH₂OH | ++++ |
| 20 | Pent-3-yl | H | —CH₂CH₂CH₂OH | +++ |
| 21 | Pent-3-yl | H | —CH₂CH₂Cl | |
| 22 | Pent-3-yl | H | 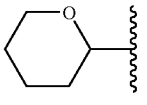 | +++ |
| 23 | Pent-3-yl | H | 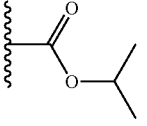 | |
| 24 | Pent-3-yl | H | 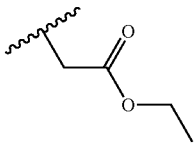 | |
| 25 | Pent-3-yl | H | 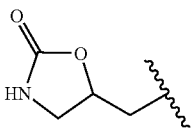 | +++ |
| 26 | Pent-3-yl | H |  | |
| 27 | Pent-3-yl | H | Benzyl | ++++ |

-continued
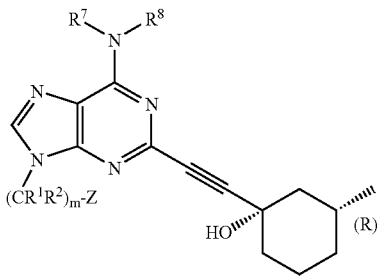
| Compound No. | R⁷ | R⁸ | (CR¹R²)ₘ-Z | Human $K_i$ (nM) |
|---|---|---|---|---|
| 28 | Pent-3-yl | H | 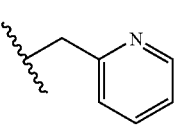 | ++++ |
| 29 | Pent-3-yl | H | 4-Nitrobenzyl | |
| 30 | Pent-3-yl | H | 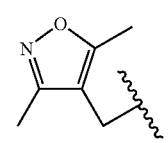 | ++++ |
| 31 | Pent-3-yl | H | 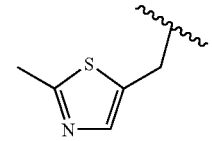 | |
| 32 | 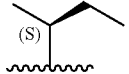 (S) | H | Propargyl | ++++ |
| 33 | 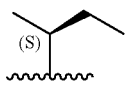 (S) | H | 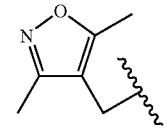 | ++++ |
| 34 | 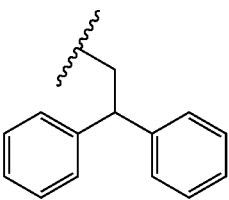 | H | —CH₃ | +++ |
| 35 | 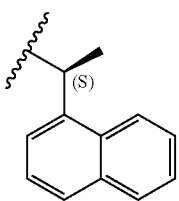 (S) | H | Propargyl | +++ |

-continued

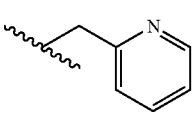

| Compound No. | R⁷ | R⁸ | (CR¹R²)ₘ-Z | Human $K_i$ (nM) |
|---|---|---|---|---|
| 36 | 3-Methoxybenzyl | H | Propargyl | ++++ |
| 37 | 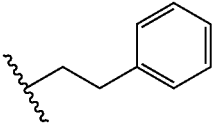 | H | Propargyl | ++++ |
| 38 | 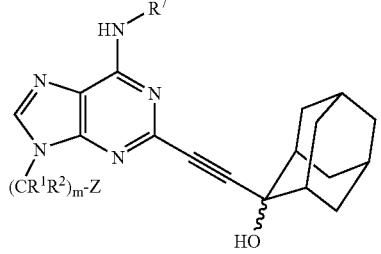 | —CH₃ | Propargyl | |

+ $K_i$ < 10,000 nM; ++ $K_i$ < 1,000 nM; +++ $K_i$ < 500 nM; ++++ $K_i$ < 100 nM.

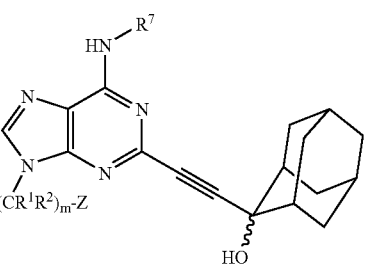

| Compound No. | R⁷ | (CR¹R²)ₘ-Z | Human $K_i$ (nM) |
|---|---|---|---|
| 39 | H | —CH₃ | ++++ |
| 40 | H | —CH₂CH₃ | ++++ |
| 41 | H | —CH₂CH₂CH₃ | ++++ |
| 42 | H | —(CH₂)₅CH₃ | ++ |
| 43 | H | —(CH₂)₈CH₃ | |
| 44 | H | Iso-propyl | +++ |
| 45 | H | 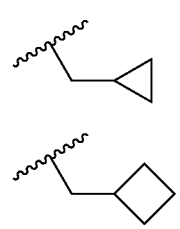 | ++++ |
| 46 | H | | ++++ |
| 47 | H | | +++ |

-continued

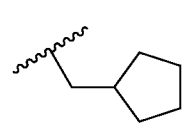

| Compound No. | R⁷ | (CR¹R²)ₘ-Z | Human $K_i$ (nM) |
|---|---|---|---|
| 48 | H | | |
| 49 | H | Cyclobutyl | ++++ |
| 50 | H | Cyclopentyl | ++++ |
| 51 | H | Propargyl | ++++ |
| 52 | H | —CH₂CH₂OH | +++ |
| 53 | H | —CH₂CH₂CH₂OH | +++ |
| 62 | H | But-3-ynyl | ++++ |

+ $K_i$ < 10,000 nM; ++ $K_i$ < 1,000 nM; +++ $K_i$ < 500 nM; ++++ $K_i$ < 100 nM.

| Compound No. | $(CR^9R^{10})_n$—Y | $(CR^1R^2)_m$-Z | Human $K_i$ (nM) |
|---|---|---|---|
| 60 | (R or S), Isomer A | Propargyl | ++++ |
| 61 | (R or S), Isomer B | Propargyl | ++++ |
| 63 | piperidine-N-C(O)OMe | Propargyl | ++++ |

+ $K_i$ < 10,000 nM; ++ $K_i$ < 1,000 nM; +++ $K_i$ < 500 nM; ++++ $K_i$ < 100 nM.

Synthesis:

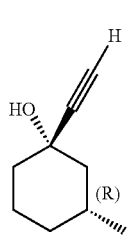

(S)-1,1-Ethynyl-hydroxy-(R)-3-methylcyclohexane. A solution of 0.5 M ethynylmagnesium bromide in THF (150.0 mL, 0.0750 mol) was added to an ice cold solution of (R)-(+)-3-methylcyclohexanone (2.77 g, 0.02469 mol) in anhydrous THF (100 mL). The ice bath was removed and the mixture stirred at room temperature 24 h. The mixture was cooled over ice and quenched with water (15.0 mL). The volume of THF was reduced to approximately 50 mL and the mixture filtered through a bed of celite/sand, washing with ether. The solution is then evaporated to dryness and the crude purified by column chromatography, eluting with a gradient of hexanes to hexanes/ethyl acetate (10%) to afford the pure product as a white crystalline solid: yield 1.412 g, 41%. $^1$H NMR (CDCl$_3$) δ 0.73–0.95, 1.10–1.19, 1.35–1.45, 1.51–1.84, 1.93–2.03 (5×m, 9H, cyclohexyl), 0.93 (d, 3H, —CH$_3$), 2.48 (s, 1H, alkyne).

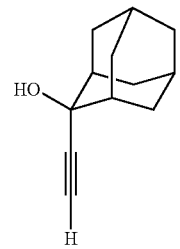

2-Ethynyl-adamantan-2-ol. A solution of 0.5 M ethynylmagnesium bromide in THF (400.0 mL, 0.2000 mol) was added to an ice cold solution of 2-adamantone (7.706 g, 0.05130 mol) in anhydrous THF (250 mL). The mixture was stirred over ice 0.5 h and then at room temperature 21 h. The volume was reduced to half and the solution cooled over ice. The reaction was quenched with water (5.0 mL), filtered through a bed of celite/sand and evaporated to dryness. The crude was taken up in ether (400 mL) and washed with water (2×40 mL) and brine (50 mL), dried over MgSO$_4$, filtered, and evaporated to dryness to afford the pure product as a crystalline white solid: yield 8.961 g, 99%. $^1$H NMR (CDCl₃) δ 1.54–1.61, 1.68–1.72, 1.76–1.99, 2.11–2.21 (4×m, 14H, adamantly), 2.53 (s, 1H, alkyne).

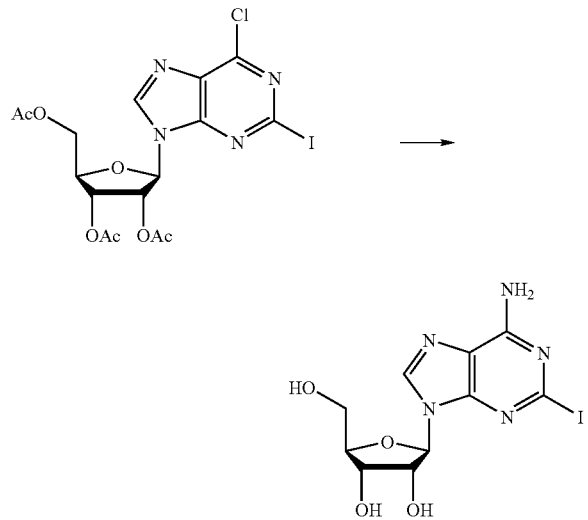

Representative procedure for N6-amino substitution: 2-Iodoadenosine. A suspension of 6-chloro-2-iodo-9-(2',3',5'-O-triacetylfuranosyl)-9H-purine (14.70 g, 0.02729 mol) in MeOH (300 mL) was cooled over an ice bath. Ammonia gas was then bubbled through the mixture until it was saturated. The reaction vessel was sealed and heated at 40° C. for 18 h and at 60° C. for 5 days. The mixture was cooled over ice and nitrogen gas bubbled through the solution, the mixture being allowed to warm to room temperature. The solvent was then removed under reduced pressure and the crude recrystallized from water containing 3–4 drops of glacial acetic acid. The resulting precipitate was filtered and washed with water and ether to afford a white solid: yield 7.167 g, 67%.

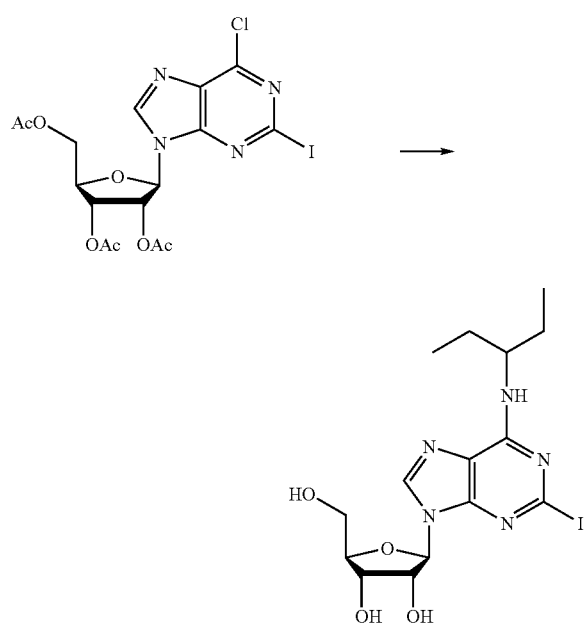

Representative procedure for N6-alkylamino substitution: 2-Iodo-6-(3-pentyl)adenosine. 6-chloro-2-iodo-9-(2',3',5'-O-triacetylfuranosyl)-9H-purine (6.723 g, 0.01248 mol), 3-aminopentane (1.673 mL, 0.01436 mol) and diisopropylethylamine (2.725 mL, 0.01560 mol) were stirred in denatured ethanol (150 mL) at 90° C. in a pressure apparatus for 21 h. The reaction was then cooled over ice and ammonia gas bubbled through the mixture until it was saturated. The reaction vessel was closed and the mixture stirred at room temperature 21 h. The mixture was cooled over ice and nitrogen gas bubbled through the solution, the mixture being allowed to warm to room temperature. The solvent was removed under reduced pressure and the crude purified by column chromatography, eluting with a gradient of DCM/MeOH (0–4%) to afford the pure product as an off white solid: yield 4.838 g, 84%.

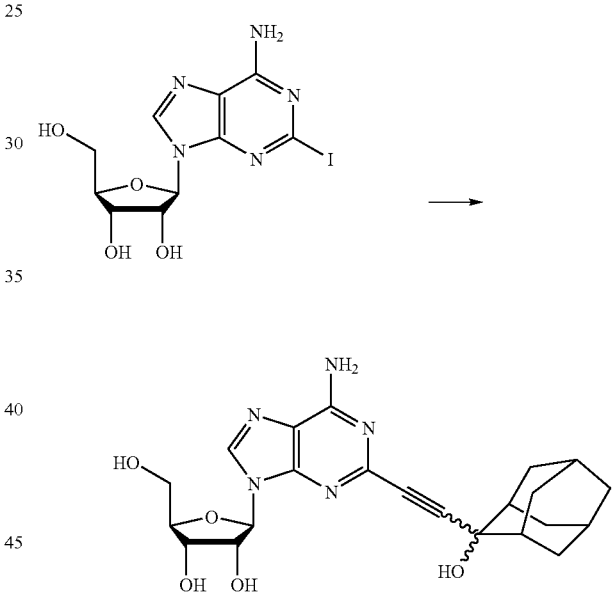

Representative procedure for C2 coupling: 2-{2-[hydroxy-adamantan-2-yl]ethyn-1-yl}adenosine. To a solution of 2-iodoadenosine (3.105 g, 7.898 mmol) in freshly degassed acetonitrile/DMF (100 mL, 1:1) was added degassed triethylamine (11.0 mL, 78.9 mmol), Pd(PPh₃)₄ (113 mg, 0.09779 mmol), CuI (catalytic), and 2,2-ethynyl-hydroxy-adamantanyl (1.516 g, 8.601 mmol). The mixture was stirred at room temperature under and inert atmosphere for 71 h. Silica bound Pd(II) scavenger Si-thiol (561 mg) and Pd(0) scavenger Si-TAAcOH (541 mg) were added and stirring continued a further 4.5 h. The suspension was filtered through celite and the resulting solution evaporated to dryness. The crude was purified by column chromatography, eluting with a gradient of DCM/MeOH (0–15%) to afford the pure product as a white solid: yield 3.476 g, 100%.

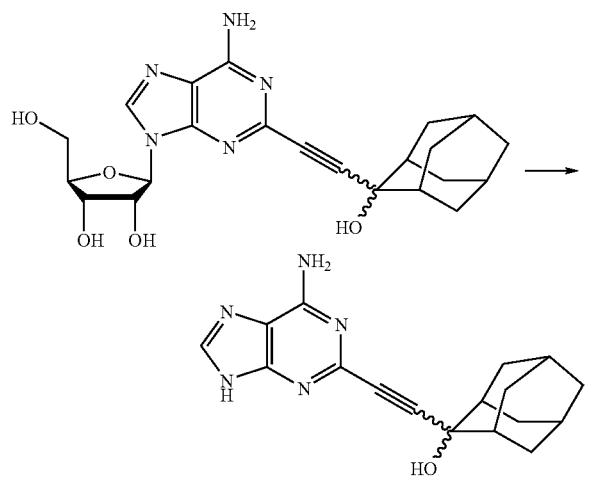

Representative procedure for ribose cleavage: 2-{2-[hydroxy-adamantan-2-yl]ethyn-1-yl}adenine. A solution of 2-{2-[hydroxy-adamantan-2-yl]ethyn-1-yl}adenosine (3.486 g, 7.896 mmol) in methanol (100 mL) and 1.0 M HCl (10.0 mL) was stirred at 90° C. in a pressure apparatus for 18–50 h. The pH was adjusted to 4.2 with 5.0 M NaOH and the volume was reduced to half under reduced pressure. After cooling the resulting precipitate was filtered and washed with methanol to afford the pure product as a white solid: yield 2.153 g, 88%. $^1$H NMR (DMSO-$d_6$) δ 8.13 (s, 1H), 7.25 (br s, 2H), 5.56 (s, 1H), 2.18–2.09, 1.94–1.89, 1.82–1.64, 1.52–1.45 (4×m, 12H). LRMS ESI (M+H$^+$) 310.1.

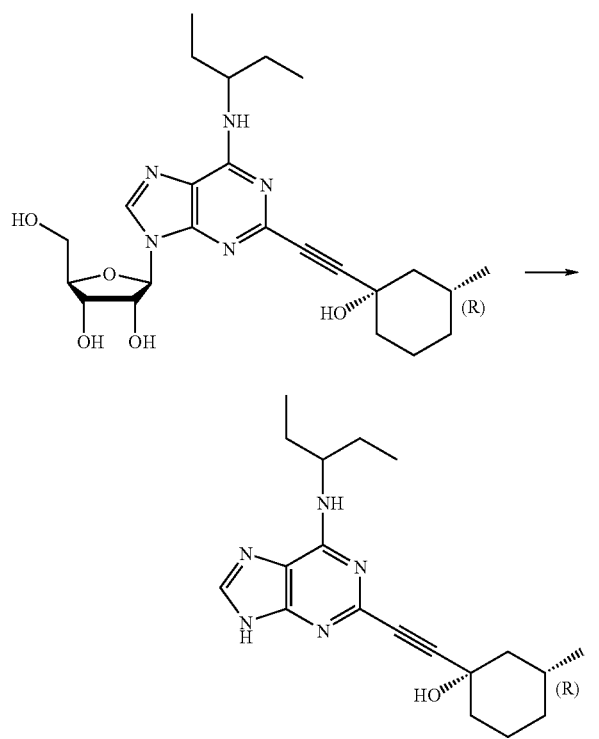

2-{2-[1(S)-Hydroxy-3(R)-methyl-1-cyclohexyl]ethyn-1-yl}-N6-(3-pentyl)adenine. Using the representative procedure for ribose cleavage above 2-{2-[1(S)-hydroxy-3(R)-methyl-1-cyclohexyl]ethyn-1-yl}-N6-(3-pentyl)adenosine (1.03 g) gave the product as a white solid: yield 0.725 g, 98%. LRMS ESI (M+H$^+$) 342.2.

Synthesis of C2, N9-Adenines:

Representative Procedure for N9-alklation using an Appropriate Alkyl Halide:

An appropriate 9-unsubstituted adenine (1.649 mmol) was dissolved in DMF (80 mL). Anhydrous potassium carbonate (358 mg, 2.590 mmol) and an appropriate alkyl halide (3.295 mmol) were added and the mix stirred at between 25–100° C. for 5–100 h. The reaction mixture was adhered to silica and purified by column chromatography, eluting with a gradient of DCM/MeOH (0–10%) to afford the pure product.

9-Cyclopropylmethyl-2-{2-[1(S)-hydroxy-3(R)-methyl-1-cyclohexyl]ethyn-1-yl}adenine (1). Using the representative procedure for N9-alkylation above 2-{2-[1(S)-hydroxy-3(R)-methyl-1-cyclohexyl]ethyn-1-yl}adenine (29 mg) gave 1 as a white solid: yield 19 mg, 55%. $^1$H NMR (CD$_3$OD) δ 8.21 (s, 1H), 4.06 (d, 2H, J=7.3 Hz), 2.13–2.05, 1.94–1.66, 1.49–1.28, 0.92–0.80, 0.66–0.59, 0.49–0.44 (6×m, 14H), 1.17 (t, 1H, J=12.3 Hz), 0.96 (d, 2H, J=6.6 Hz). LRMS ESI (M+H$^+$) 326.1.

2-{2-[1(S)-Hydroxy-3(R)-methyl-1-cyclohexyl]ethyn-1-yl}-9-propargyladenine (2). Using the representative procedure for N9-alkylation above 2-{2-[1(S)-hydroxy-3(R)-methyl-1-cyclohexyl]ethyn-1-yl}adenine (112 mg) gave 2 as an off white solid: yield 88 mg, 69%. $^1$H NMR (CD$_3$OD) δ 8.23 (s, 1H), 5.04 (s, 2H), 2.98 (t, 1H, J=2.6 Hz), 2.13–2.05, 1.94–1.65, 1.49–1.38, 0.91–0.80, (4×m, 7H), 1.17 (t, 1H, J=12.3 Hz), 0.95 (d, 2H, J=6.6 Hz). LRMS ESI (M+H$^+$) 310.1.

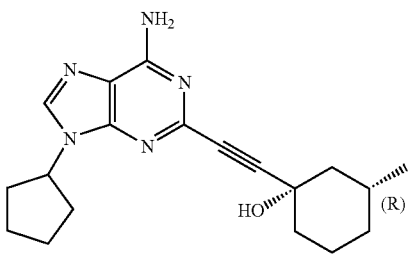

9-Cyclopentyl-2-{2-[1(S)-hydroxy-3(R)-methyl-1-cyclohexyl]ethyn-1-yl}adenine (3). Using the representative procedure for N9-alkylation above 2-{2-[1(S)-hydroxy-3(R)-methyl-1-cyclohexyl]ethyn-1-yl}adenine (34 mg) gave 3 as a white solid: yield 21 mg, 50%. $^1$H NMR (CD$_3$OD) δ 8.21 (s, 1H), 4.91 (tt, 1H, J=7.0 Hz), 2.31–2.19, 2.13–1.65, 1.49–1.38, 0.92–0.79 (4×m, 17H), 1.15 (t, 1H, J=12.3 Hz), 0.96 (d, 2H, J=6.6 Hz). LRMS ESI (M+H$^+$) 340.2.

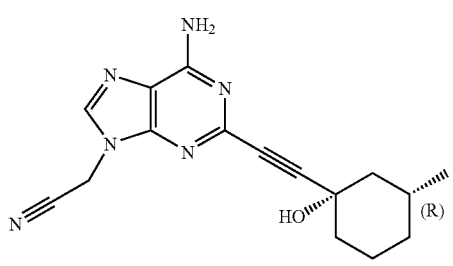

9-Acetonitrile-2-{2-[1(S)-hydroxy-3(R)-methyl-1-cyclohexyl]ethyn-1-yl}adenine (4). Using the representative procedure for N9-alkylation above 2-{2-[1(S)-hydroxy-3(R)-methyl-1-cyclohexyl]ethyn-1-yl}adenine (43 mg) gave 4 as a white solid: yield 25 mg, 51%. $^1$H NMR (CD$_3$OD) δ 8.20 (s, 1H), 5.35 (s, 1H), 2.33–2.05, 1.93–1.66, 1.49–1.38, 0.92–0.80 (4×m, 9H), 1.18 (t, 1H, J=12.3 Hz), 0.96 (d, 2H, J=6.6 Hz). LRMS ESI (M+H$^+$) 311.1.

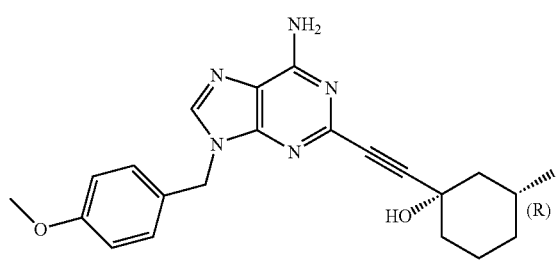

2-{2-[1(S)-Hydroxy-3(R)-methyl-1-cyclohexyl]ethyn-1-yl}-9-(4-methoxybenzyl)adenine (5). Using the representative procedure for N9-alkylation above 2-{2-[1(S)-hydroxy-3(R)-methyl-1-cyclohexyl]ethyn-1-yl}adenine (24 mg) gave 5 as a white solid: yield 29 mg, 84%. $^1$H NMR (CD$_3$OD) δ 8.10 (s, 1H), 7.26 (d, 2H, J=8.8 Hz), 6.88 (d, 2H, J=8.8 Hz), 5.32 (s, 2H), 3.75 (s, 3H), 2.33–2.05, 1.92–1.66, 1.49–1.38, 0.92–0.80 (4×m, 9H), 1.17 (t, 1H, J=12.3 Hz), 0.95 (d, 2H, J=6.6 Hz). LRMS ESI (M+H$^+$) 392.2.

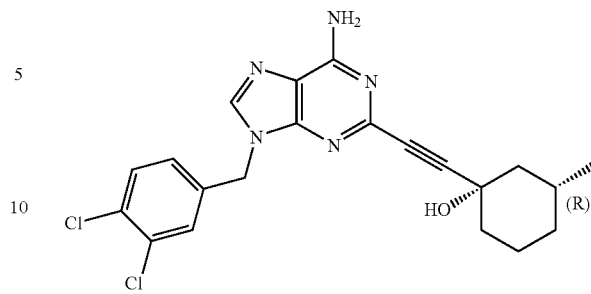

9-(3,4-Dichlorobenzyl)-2-{2-[1(S)-hydroxy-3(R)-methyl-1-cyclohexyl]ethyn-1-yl}adenine (6). Using the representative procedure for N9-alkylation above 2-{2-[1(S)-hydroxy-3(R)-methyl-1-cyclohexyl]ethyn-1-yl}adenine (26 mg) gave 6 as a white solid: yield 28 mg, 68%. $^1$H NMR (CD$_3$OD) δ 8.20 (s, 1H), 7.52 (d, 1H, J=2.1 Hz), 7.48 (d, 1H, J=8.3 Hz), 7.19 (dd, 1H, J=2.1 Hz, J=8.3 Hz), 5.40 (s, 2H), 2.11–2.04, 1.92–1.64, 1.48–1.37, 0.92–0.79 (4×m, 9H), 1.16 (t, 1H, J=12.3 Hz), 0.94 (d, 2H, J=6.6 Hz). LRMS ESI (M+H$^+$) 430.2.

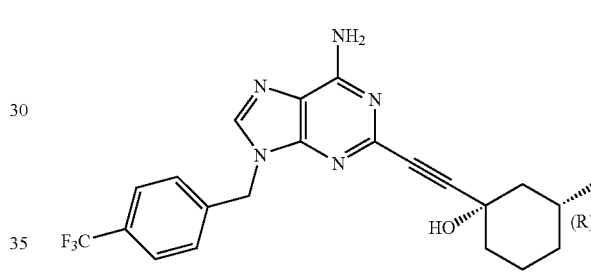

2-{2-[1(S)-Hydroxy-3(R)-methyl-1-cyclohexyl]ethyn-1-yl}-9-(4-trifluoromethylbenzyl)adenine (7). Using the representative procedure for N9-alkylation above 2-{2-[1(S)-hydroxy-3(R)-methyl-1-cyclohexyl]ethyn-1-yl}adenine (30 mg) gave 7 as a white solid: yield 33 mg, 70%. $^1$H NMR (CD$_3$OD) δ 8.20 (s, 1H), 7.64 (d, 2H, J=8.2 Hz), 7.44 (d, 2H, J=8.1 Hz), 5.52 (s, 2H), 2.10–2.03, 1.90–1.63, 1.47–1.36, 0.90–0.78 (4×m, 9H), 1.15 (t, 1H, J=12.3 Hz), 0.93 (d, 2H, J=6.6 Hz). LRMS ESI (M+H$^+$) 430.1.

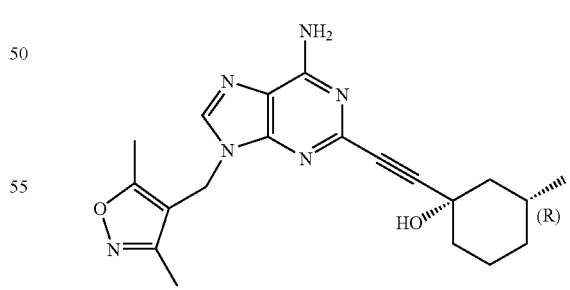

9-(3,5-Dimethyl-isoxazol-4-ylmethyl)-2-{2-[1(S)-hydroxy-3(R)-methyl-1-cyclohexyl]ethyn-1-yl}adenine (8). Using the representative procedure for N9-alkylation above 2-{2-[1(S)-hydroxy-3(R)-methyl-1-cyclohexyl]ethyn-1-yl}adenine (32 mg) gave 8 as a white solid: yield 36 mg, 80%. $^1$H NMR (CD$_3$OD) δ 8.15 (s, 1H), 5.20 (s, 2H), 2.50 (s, 3H), 2.22 (s, 3H), 2.11–2.03, 1.92–1.65, 1.49–1.38, 0.92–0.81 (4×m, 9H), 1.18 (t, 1H, J=12.2 Hz), 0.96 (d, 2H, J=6.6 Hz). LRMS ESI (M+H⁺) 381.1.

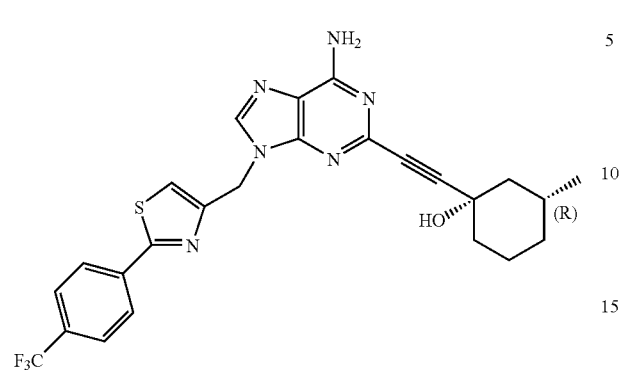

2-{2-[1(S)-Hydroxy-3(R)-methyl-1-cyclohexyl]ethyn-1-yl}-9-[2-(trifluoromethylphenyl)thiazol-4-ylmethyl]adenine (9). Using the representative procedure for N9-alkylation above 2-{2-[1(S)-hydroxy-3(R)-methyl-1-cyclohexyl]ethyn-1-yl}adenine (26 mg) gave 9 as a white solid: yield 30 mg, 61%. ¹H NMR (CD₃OD) δ 8.31 (s, 1H), 8.09 (d, 2H, J=8.8 Hz), 7.74 (d, 2H, J=8.3 Hz), 7.55 (s, 1H), 5.58 (s, 2H), 2.12–2.04 1.91–1.64, 1.48–1.37, 0.91–0.78 (4×m, 9H), 1.16 (t, 1H, J=12.4 Hz), 0.94 (d, 2H, J=6.6 Hz). LRMS ESI (M+H⁺) 513.1.

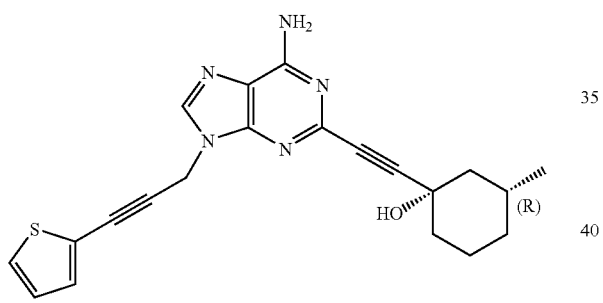

2-{2-[Hydroxy-adamantan-2-yl]ethyn-1-yl}-9-(3-(thiophen-2-yl)prop-2-ynyl)adenine (10). To a solution of 2-{2-[1(S)-hydroxy-3(R)-methyl-1-cyclohexyl]ethyn-1-yl}-9-propargyladenine (30 mg, 0.09697 mmol) in freshly degassed acetonitrile/DMF (15 mL, 2:1) was added degassed triethylamine (1.0 mL, 7.0175 mmol), Pd(PPh₃)₄ (30 mg, 0.02596 mmol), CuI (catalytic), and 98+% 2-bromothiophene (13.7 µL, 0.1161 mmol). The mixture was stirred at room temperature under and inert atmosphere for 28 h. Silica bound Pd(II) scavenger Si-thiol (240 mg) and Pd(0) scavenger Si-TAAcOH (155 mg) were added and stirring continued a further 72 h. The suspension was filtered through celite and the resulting solution evaporated to dryness. The crude was purified by column chromatography, eluting with a gradient of DCM/MeOH (0–6%) to afford the impure product (27 mg). The product was further purified by reverse phase column chromatography, eluting with a gradient of H₂/MeOH (50–75%) to afford the pure product 10 as a white solid: yield 8.5 mg, 22%. ¹H NMR (CD₃OD) δ 8.27 (s, 1H), 7.41(dd, 1H, J=1.1 Hz, J=5.3 Hz), 7.25 (dd, 2H, J=1.1 Hz, J=3.5 Hz), 6.99 (dd, 1H, J=3.7 Hz, J=5.0 Hz), 5.29 (s, 2H), 2.14–2.05, 1.94–1.65, 1.49–1.37, 0.99–0.79 (4×m, 12H), 1.17 (t, 1H, J=12.2 Hz). LRMS ESI (M+H⁺) 392.1.

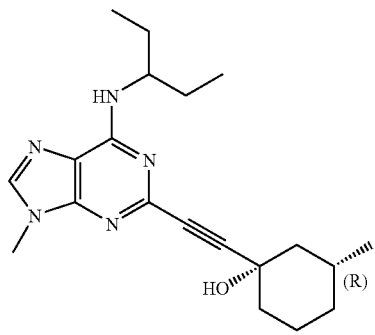

2-{2-[1(S)-Hydroxy-3(R)-methyl-1-cyclohexyl]ethyn-1-yl}-9-methyl-N6-(3-pentyl)adenine (11). Using the representative procedure for N9-alkylation above 2-{2-[1(S)-hydroxy-3(R)-methyl-1-cyclohexyl]ethyn-1-yl}-N6-(3-pentyl)adenine (20 mg) gave 11 as a white solid: yield 9 mg, 43%. ¹H NMR (CD₃OD) δ 8.02 (s, 1H), 4.23 (m, 1H), 3.79 (s, 3H), 2.14–2.06, 1.96–1.38, 0.99–0.80 (3×m, 20H), 1.17 (t, 1H, J=12.3 Hz). LRMS ESI (M+H⁺⁾ 356.3.

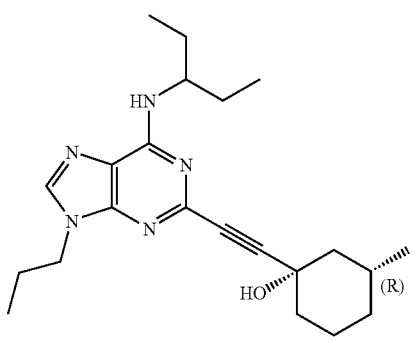

2-{2-[1(S)-Hydroxy-3(R)-methyl-1-cyclohexyl]ethyn-1-yl}-N6-(3-pentyl)-9-propyladenine (12). Using the representative procedure for N9-alkylation above 2-{2-[1(S)-hydroxy-3(R)-methyl-1-cyclohexyl]ethyn-1-yl}-N6-(3-pentyl)adenine (29 mg) gave 12 as a white solid: yield 26 mg, 80%. ¹H NMR (CD₃OD) δ 8.08 (s, 1H), 4.28–4.13 (m, 3H), 2.15–2.06, 1.95–1.38, 0.99–0.80 (3×m, 26H), 1.17 (t, 1H, J=12.3 Hz). LRMS ESI (M+H⁺) 384.3.

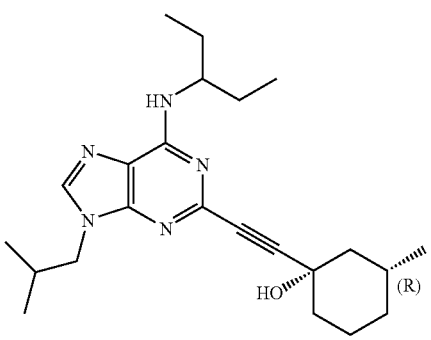

9-Isobutyl-2-{2-[1(S)-hydroxy-3(R)-methyl-1-cyclohexyl]ethyn-1-yl}-N6-(3-pentyl)adenine (13). Using the representative procedure for N9-alkylation above 2-{2-[1(S)-hydroxy-3(R)-methyl-1-cyclohexyl]ethyn-1-yl}-N6-(3-pentyl)adenine (27 mg) gave 13 as a white solid: yield 23 mg, 73%. $^1$H NMR (CD$_3$OD) δ 8.06 (s, 1H), 4.21 (m, 1H), 4.01 (d, 2H, J=7.4 Hz), 2.21 (septet, 1H, J=6.8 Hz), 2.12–2.05, 1.96–1.38, 0.98–0.81 (3×m, 27H), 1.17 (t, 1H, J=12.2 Hz). LRMS ESI (M+H$^+$) 398.2.

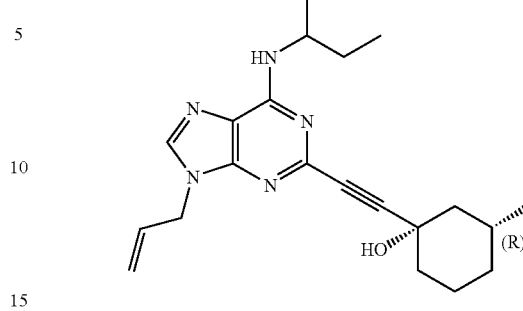

9-Allyl-2-{2-[1(S)-hydroxy-3(R)-methyl-1-cyclohexyl]ethyn-1-yl}-N6-(3-pentyl)adenine (16). Using the representative procedure for N9-alkylation above 2-{2-[1(S)-hydroxy-3(R)-methyl-1-cyclohexyl]ethyn-1-yl}-N6-(3-pentyl)adenine (33 mg) gave 16 as a white solid: yield 26 mg, 71%. $^1$H NMR (CDCl$_3$) δ 7.77 (br s, 1H), 6.09–5.95 (m, 1H), 5.34–5.20 (m, 2H), 4.79 (dt, 2H, J=5.8 Hz, J=1.5 Hz), 4.28 (m, 1H), 2.21–2.11, 1.96–1.42, 0.96–0.78 (3×m, 21H), 1.23 (t, 1H, J=12.2 Hz). LRMS ESI (M+H$^+$) 382.3.

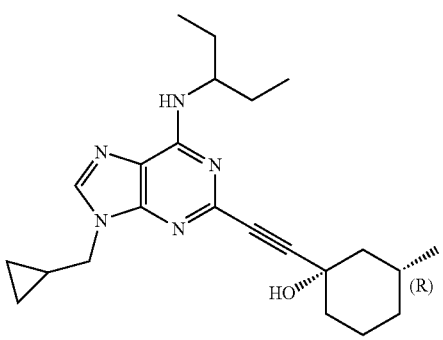

9-Cyclopropylmethyl-2-{2-[1(S)-hydroxy-3(R)-methyl-1-cyclohexyl]ethyn-1-yl}-N6-(3-pentyl)adenine (14). Using the representative procedure for N9-alkylation above 2-{2-[1(S)-hydroxy-3(R)-methyl-1-cyclohexyl]ethyn-1-yl}-N6-(3-pentyl)adenine (30 mg) gave 14 as a white solid: yield 17 mg, 57%. $^1$H NMR (CD$_3$OD) δ 8.15 (s, 1H), 4.22 (m, 1H), 4.05 (d, 2H, J=7.3 Hz), 2.14–2.05, 1.96–1.28, 0.98–0.79 (3×m, 22H), 1.17 (t, 1H, J=12.2 Hz), 0.65–0.58 (m, 2H), 0.48–0.44 (m, 2H). LRMS ESI (M+H$^+$) 396.3.

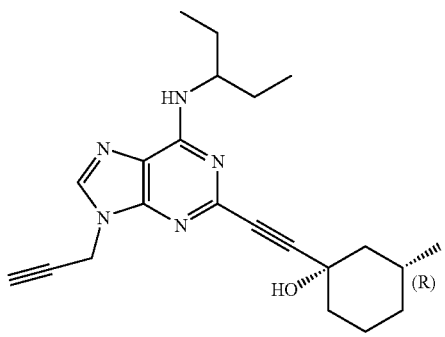

2-{2-[1(S)-Hydroxy-3(R)-methyl-1-cyclohexyl]ethyn-1-yl}-N6-(3-pentyl)-9-(propargyl)adenine (17). Using the representative procedure for N9-alkylation above 2-{2-[1(S)-hydroxy-3(R)-methyl-1-cyclohexyl]ethyn-1-yl}-N6-(3-pentyl)adenine (134 mg) gave 17 as a white solid: yield 79 mg, 53%. $^1$H NMR (CD$_3$OD) δ 8.17 (s, 1H), 5.03 (d, 2H, J=2.6 Hz), 4.22 (m, 1H), 2.97 (t, 1H, J=2.6), 2.14–2.06, 1.95–1.38, 0.98–0.80 (3×m, 21H), 1.17 (t, 1H, J=12.4 Hz). LRMS ESI (M+H$^+$) 380.2.

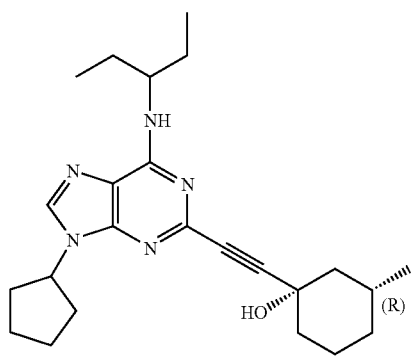

9-Cyclopentyl-2-{2-[1(S)-hydroxy-3(R)-methyl-1-cyclohexyl]ethyn-1-yl}-N6-(3-pentyl)adenine (15). Using the representative procedure for N9-alkylation above 2-{2-[1(S)-hydroxy-3(R)-methyl-1-cyclohexyl]ethyn-1-yl}-N6-(3-pentyl)adenine (37 mg) gave 15 as a white solid: yield 29 mg, 65%. $^1$H NMR (CD$_3$OD) δ 8.15 (s, 1H), 4.91 (tt, 1H, J=7.0 Hz), 4.21 (m, 1H), 2.31–2.17, 2.14–1.35, 0.98–0.79 (3×m, 29H), 1.17 (t, 1H, J=12.2 Hz). LRMS ESI (M+H$^+$) 410.3.

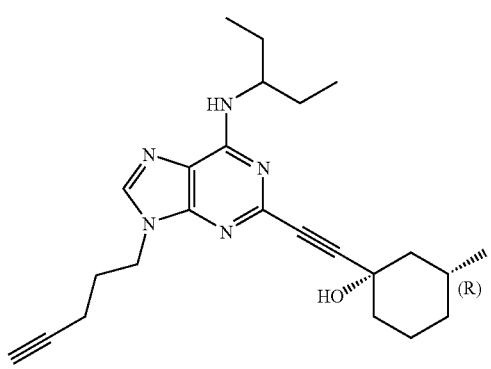

2-{2-[1(S)-Hydroxy-3(R)-methyl-1-cyclohexyl]ethyn-1-yl}-N6-(3-pentyl)-9-(pent-4-yne)adenine (18). Using the representative procedure for N9-alkylation above 2-{2-[1(S)-hydroxy-3(R)-methyl-1-cyclohexyl]ethyn-1-yl}-N6-(3-pentyl)adenine (35 mg) gave 18 as a white solid: yield 31 mg, 74%. $^1$H NMR (CD$_3$OD) δ 8.07 (s, 1H), 4.32 (t, 2H, J=6.9 Hz), 4.21 (m, 1H), 2.31–2.19, 2.14–2.00, 1.95–1.38, 1.00–0.79 (4×m, 21H), 1.17 (t, 1H, J=12.3 Hz). LRMS ESI (M+H$^+$) 408.1.

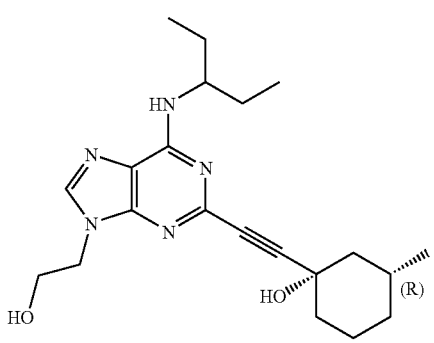

9-(2-Hydroxyethyl)-2-{2-[1(S)-hydroxy-3(R)-methyl-1-cyclohexyl]ethyn-1-yl}-N6-(3-pentyl)adenine (19). Using the representative procedure for N9-alkylation above 2-{2-[1(S)-hydroxy-3(R)-methyl-1-cyclohexyl]ethyn-1-yl}-N6-(3-pentyl)adenine (103 mg) gave 19 as a white solid: yield 60 mg, 52%. $^1$H NMR (CD$_3$OD) δ 8.06 (s, 1H), 4.30 (t, 2H, J=5.1 Hz), 4.22 (m, 1H), 3.86 (t, 2H, J=5.1 Hz), 2.14–2.05, 1.95–1.38, 0.99–0.80 (3×m, 21H), 1.17 (t, 1H, J=12.2 Hz). LRMS ESI (M+H$^+$) 386.2.

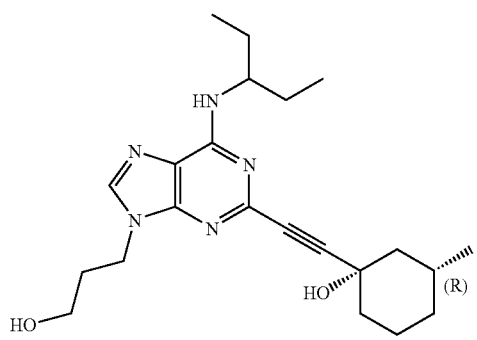

2-{2-[1(S)-Hydroxy-3(R)-methyl-1-cyclohexyl]ethyn-1-yl}-9-(3-hydroxypropyl)-N6-(3-pentyl)adenine (20). Using the representative procedure for N9-alkylation above 2-{2-[1(S)-hydroxy-3(R)-methyl-1-cyclohexyl]ethyn-1-yl}-N6-(3-pentyl)adenine (59 mg) gave 20 as a white solid: yield 35 mg, 51%. $^1$H NMR (CD$_3$OD) δ 8.11 (s, 1H), 4.32 (t, 2H, J=7.0 Hz), 4.20 (m, 1H), 3.56 (t, 2H, J=5.9 Hz), 2.14–2.00, 1.93–1.38, 0.99–0.80 (3×m, 23H), 1.17 (t, 1H, J=12.2 Hz). LRMS ESI (M+H$^+$) 400.3.

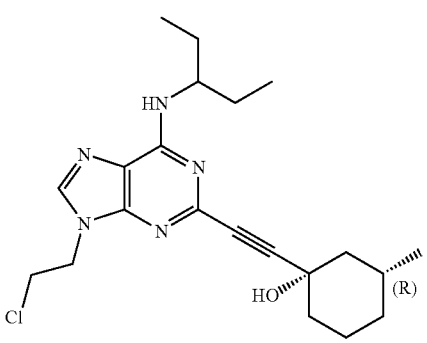

9-(2-Chloroethyl)-2-{2-[1(S)-hydroxy-3(R)-methyl-1-cyclohexyl]ethyn-1-yl}-N6-(3-pentyl)adenine (21). Using the representative procedure for N9-alkylation above 2-{2-[1(S)-hydroxy-3(R)-methyl-1-cyclohexyl]ethyn-1-yl}-N6-(3-pentyl)adenine (38 mg) gave 21 as a white solid: yield 28 mg, 62%. $^1$H NMR (CD$_3$OD) δ 8.11 (s, 1H), 4.55 (t, 2H, J=5.7 Hz), 4.22 (m, 1H), 3.96 (t, 2H, J=5.7 Hz), 2.14–2.05, 1.94–1.38, 0.99–0.79 (3×m, 21H), 1.17 (t, 1H, J=12.1 Hz). LRMS ESI (M+H$^+$) 404.2.

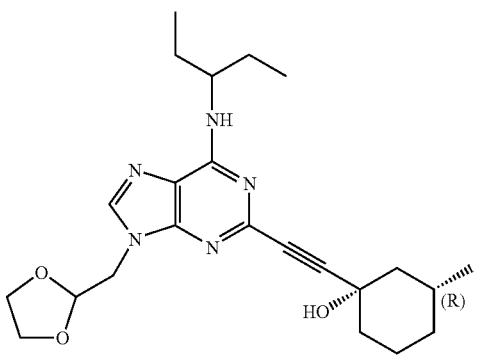

9-([1,3]-Dioxolan-2-ylmethyl)-2-{2-[1(S)-hydroxy-3(R)-methyl-1-cyclohexyl]ethyn-1-yl}-N6-(3-pentyl)adenine (22). Using the representative procedure for N9-alkylation above 2-{2-[1(S)-hydroxy-3(R)-methyl-1-cyclohexyl]ethyn-1-yl}-N6-(3-pentyl)adenine (37 mg) gave 22 as a white solid: yield 32 mg, 69%. $^1$H NMR (CD$_3$OD) δ 8.04 (s, 1H), 5.20 (t, 1H, J=3.3 Hz), 4.40 (d, 2H, J=3.3 Hz), 4.21 (m, 1H), 3.88–3.76 (m, 4H), 2.14–2.06, 1.92–1.38, 0.98–0.79 (3×m, 21H), 1.17 (t, 1H, J=12.2 Hz). LRMS ESI (M+H$^+$) 428.3.

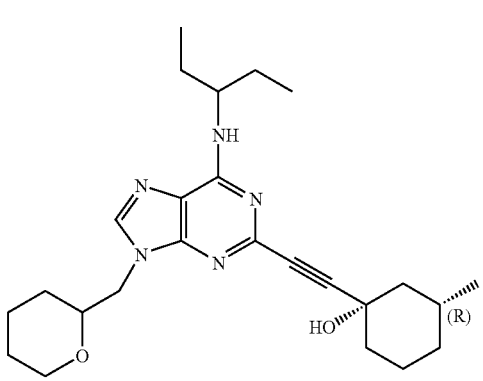

2-{2-[1(S)-Hydroxy-3(R)-methyl-1-cyclohexyl]ethyn-1-yl}-N6-(3-pentyl)-9-(tetrahydro-pyran-2-ylmethyl)adenine (23). Using the representative procedure for N9-alkylation above 2-{2-[1(S)-hydroxy-3(R)-methyl-1-cyclohexyl]ethyn-1-yl}-N6-(3-pentyl)adenine (32 mg) gave 23 as a white solid: yield 27 mg, 66%. $^1$H NMR (CD$_3$OD) δ 8.01 (s, 1H), 4.31–4.07 (m, 3H), 3.96–3.87 (m, 1H), 3.67–3.58 (m, 1H), 3.93–3.32 (m, 1H), 2.14–2.06, 1.95–1.38, 1.31–1.12, 0.99–0.80 (4×m, 28H). LRMS ESI (M+H$^+$) 440.4.

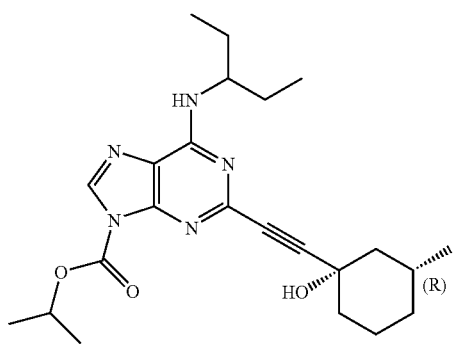

2-{2-[1(S)-Hydroxy-3(R)-methyl-1-cyclohexyl]ethyn-1-yl}-N6-(3-pentyl)-9-(isopropylcarboxylate)adenine (24). A 1.0 M solution of isopropyl chloroformate in toluene (150 μL, 0.1500 mmol) was added to an ice cold solution of 2-{2-[1(S)-hydroxy-3(R)-methyl-1-cyclohexyl]ethyn-1-yl}-N6-(3-pentyl)adenine (34 mg) in anhydrous pyridine (2.0 mL). After stirring over ice 1.5 h the solvent was removed under reduced pressure and the crude purified by column chromatography, eluting with a gradient of DCM/MeOH (0–5%) to afford the pure product 24 as an off white solid: yield 18 mg, 42%. $^1$H NMR (CD$_3$OD) δ 8.44 (s, 1H), 5.29 (septet, 1H, J=6.4, J=6.2 Hz), 4.21 (m, 1H), 2.14–2.05, 1.97–1.37, 1.00–0.79 (3×m, 27H), 1.16 (t, 1H, J=12.2 Hz). LRMS ESI (M+H$^+$) 427.9.

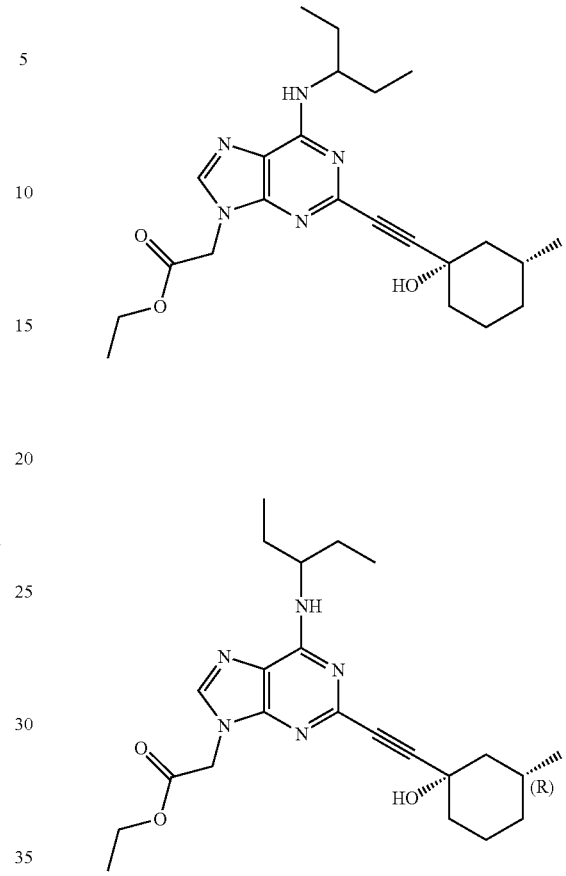

9-(Acetic acid ethyl ester)-2-{2-[1(S)-hydroxy-3(R)-methyl-1-cyclohexyl]ethyn-1-yl}-N6-(3-pentyl)adenine (25). Using the representative procedure for N9-alkylation above 2-{2-[1(S)-hydroxy-3(R)-methyl-1-cyclohexyl]ethyn-1-yl}-N6-(3-pentyl)adenine (38 mg) gave 25 as a white solid: yield 9 mg, 19%. $^1$H NMR (CD$_3$OD) δ 8.06 (s, 1H), 5.06 (s, 2H), 4.24 (br q, 3H, J=7.0, 7.3 Hz), 2.15–2.05, 1.95–1.37, 1.05–0.79 (3×m, 22H), 1.29 (t, 3H, J=7.0, 7.3 Hz), 1.17 (t, 1H, J=12.2 Hz). LRMS ESI (M+H$^+$) 428.2.

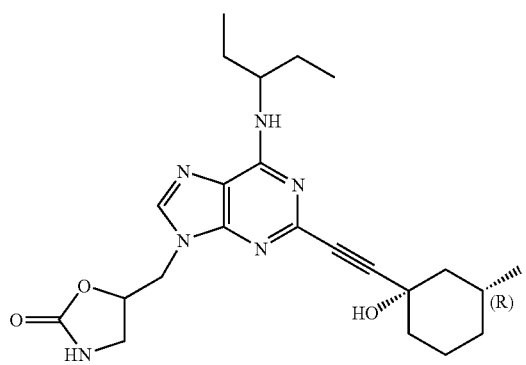

2-{2-[1(S)-Hydroxy-3(R)-methyl-1-cyclohexyl]ethyn-1-yl}-9-(2-oxo-oxazolidin-5-ylmethyl)-N6-(3-pentyl)adenine (26). Using the representative procedure for N9-alkylation above 2-{2-[1(S)-hydroxy-3(R)-methyl-1-cyclohexyl]ethyn-1-yl}-N6-(3-pentyl)adenine (56 mg) gave 26 as a white solid: yield 43 mg, 60%. $^1$H NMR (CD$_3$OD) δ 8.09 (s, 1H), 5.04 (m, 1H), 4.52 (d, 2H, J=4.8 Hz), 4.21 (m, 1H), 3.79–3.70 (m, 1H), 3.47–3.39 (m, 1H), 2.13–2.04, 1.95–1.38, 0.99–0.79 (3×m, 21H), 1.17 (t, 1H, J=12.2 Hz). LRMS ESI (M+H$^+$) 441.3.

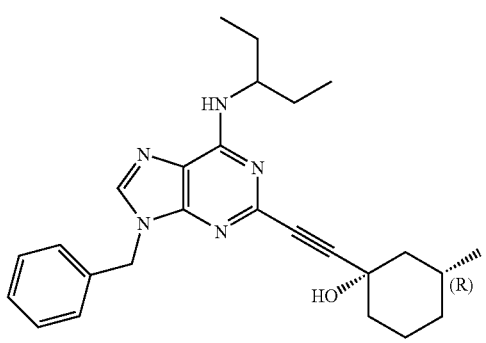

9-Benzyl-2-{2-[1(S)-hydroxy-3(R)-methyl-1-cyclohexyl]ethyn-1-yl}-N6-(3-pentyl)adenine (27). Using the representative procedure for N9-alkylation above 2-{2-[1(S)-hydroxy-3(R)-methyl-1-cyclohexyl]ethyn-1-yl}-N6-(3-pentyl)adenine (37 mg) gave 27 as a white solid: yield 31 mg, 66%. $^1$H NMR (CD$_3$OD) δ 8.06 (s, 1H), 7.37–7.25 (m, 5H), 5.40 (s, 2H), 4.22 (m, 1H), 2.14–2.05, 1.95–1.37, 0.99–0.79 (3×m, 21H), 1.16 (t, 1H, J=12.3 Hz). LRMS ESI (M+H$^+$) 432.3.

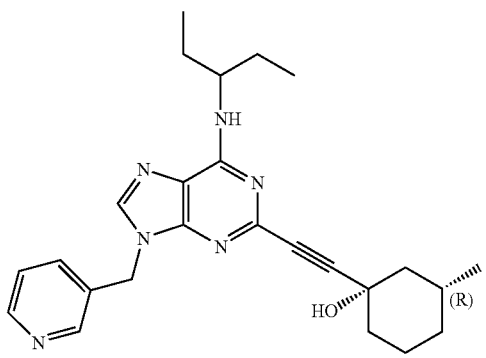

2-{2-[1(S)-Hydroxy-3(R)-methyl-1-cyclohexyl]ethyn-1-yl}-N6-(3-pentyl)-9-(pyridin-3-ylmethyl)adenine (28). Using the representative procedure for N9-alkylation above 2-{2-[1(S)-hydroxy-3(R)-methyl-1-cyclohexyl]ethyn-1-yl}-N6-(3-pentyl)adenine (34 mg) gave 28 as a white solid: yield 8 mg, 19%. $^1$H NMR (CD$_3$OD) δ 8.57 (m, 1H), 8.48 (m, 1H), 8.17 (s, 1H), 7.77 (m, 1H), 7.41 (m, 1H), 5.49 (s, 2H), 4.22 (m, 1H), 2.13–2.04, 1.93–1.37, 0.99–0.79 (3×m, 21H), 1.16 (t, 1H, J=12.3 Hz). LRMS ESI (M+H$^+$) 433.3.

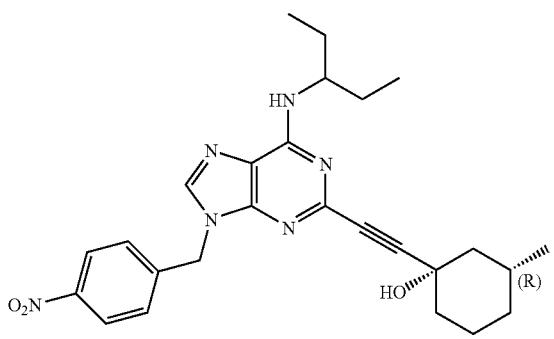

2-{2-[1(S)-Hydroxy-3(R)-methyl-1-cyclohexyl]ethyn-1-yl}-9-(4-nitrobenzyl)-N6-(3-pentyl)adenine (29). Using the representative procedure for N9-alkylation above 2-{2-[1(S)-hydroxy-3(R)-methyl-1-cyclohexyl]ethyn-1-yl}-N6-(3-pentyl)adenine (33 mg) gave 29 as a white solid: yield 36 mg, 78%. $^1$H NMR (CD$_3$OD) δ 8.19 (d, 2H, J=8.8 Hz), 8.16 (s, 1H), 7.46 (d, 2H, J=8.8 Hz), 5.55 (s, 2H), 4.22 (m, 1H), 2.12–2.02, 1.92–1.36, 1.00–0.78 (3×m, 21H), 1.15 (t, 1H, J=12.2 Hz). LRMS ESI (M+H$^+$) 477.3.

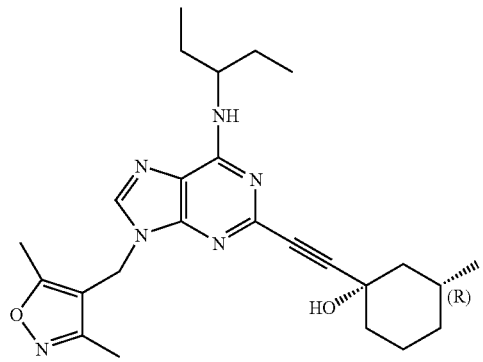

9-(3,5-Dimethyl-isoxazol-4-ylmethyl)-2-{2-[1(S)-hydroxy-3(R)-methyl-1-cyclohexyl]ethyn-1-yl}-N6-(3-pentyl)adenine (30). Using the representative procedure for N9-alkylation above 2-{2-[1(S)-hydroxy-3(R)-methyl-1-cyclohexyl]ethyn-1-yl}-N6-(3-pentyl)adenine (50 mg) gave 30 as a white crystalline solid: yield 50 mg, 76%. $^1$H NMR (CD$_3$OD) δ 8.08 (s, 1H), 5.18 (s, 2H), 4.19 (m, 1H), 2.50 (s, 3H), 2.23 (s, 3H), 2.13–2.04, 1.94–1.38, 0.99–0.80 (3×m, 21H), 1.18 (t, 1H, J=12.1 Hz). LRMS ESI (M+H$^+$) 451.3.

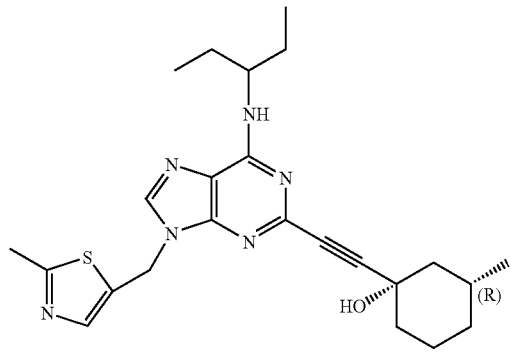

2-{2-[1(S)-Hydroxy-3(R)-methyl-1-cyclohexyl]ethyn-1-yl}-9-(2-methyl-thiazol-5-ylmethyl)-N6-(3-pentyl)adenine (31). 2-{2-[1-(S)-Hydroxy-3(R)-methyl-1-cyclohexyl]ethyn-1-yl}-N6-(3-pentyl)adenine (56 mg, 0.1640 mmol) and 4-chloromethyl-2-methylthiazole hydrochloride (127 mg, 0.6899 mmol) were stirred in DMF (8 mL) at 150° C. for 22 h. The reaction mixture was adhered to silica and purified by column chromatography, eluting with a gradient of DCM/MeOH (0–6%) to afford pure 31 as an off white solid: yield 2 mg, 3%. ¹H NMR (CD₃OD) δ 8.12 (s, 1H), 7.29 (s, 1H), 5.44 (s, 2H), 4.22 (m, 1H), 2.65 (s, 3H), 2.14–2.05, 1.94–1.37, 0.99–0.80 (3×m, 21H), 1.18 (t, 1H, J=12.2 Hz). LRMS ESI (M+H⁺) 453.2.

tyl)adenine (42 mg) gave 33 as a white solid: yield 31 mg, 55%. ¹H NMR (CD₃OD) δ 8.08 (s, 1H), 5.19 (s, 2H), 4.29 (m, 1H), 2.50 (s, 3H), 2.22 (s, 3H), 2.14–2.04, 1.95–1.57, 1.49–1.38, 0.99–0.82 (4×m, 16H), 1.24 (d, 3H, J=6.4 Hz), 1.18 (t, 1H, J=12.2 Hz). LRMS ESI (M+H⁺) 437.2.

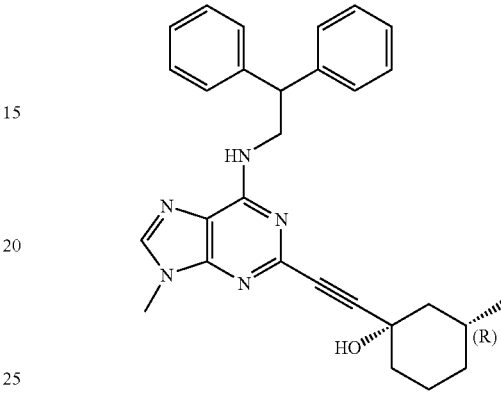

N6-(2-Diphenylethyl)-2-{2-[1(S)-hydroxy-3(R)-methyl-1-cyclohexyl]ethyn-1-yl}-9-methyladenine (34). Using the representative procedure for N9-alkylation above N6-(2-diphenylethyl)-2-{2-[1(S)-hydroxy-3(R)-methyl-1-cyclohexyl]ethyn-1-yl}adenine (14 mg) gave 34 as a white solid: yield 5 mg, 35%. LRMS ESI (M+H⁺) 466.3.

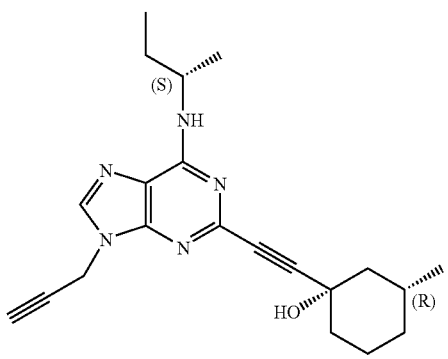

N6-[(S)-(+)-sec-Butyl]-2-{2-[1(S)-hydroxy-3(R)-methyl-1-cyclohexyl]ethyn-1-yl}-9-propargyl-adenine (32). Using the representative procedure for N9-alkylation above N6-[(S)-(+)-sec-butyl]-2-{2-[1-(S)-hydroxy-3(R)-methyl-1-cyclohexyl]ethyn-1-yl}-N6-(3-pentyl)adenine (29 mg) gave 32 as a white solid: yield 20 mg, 62%. ¹H NMR (CD₃OD) δ 8.17 (s, 1H), 5.03 (d, 2H, J=2.6 Hz), 4.32 (m, 1H), 2.97 (t, 1H, J=2.6 Hz), 2.14–2.06, 1.95–1.58, 1.49–1.38, 1.00–0.79 (4×m, 16H), 1.25 (d, 3H, J=6.4 Hz), 1.17 (t, 1H, J=12.2 Hz). LRMS ESI (M+H⁺) 366.1.

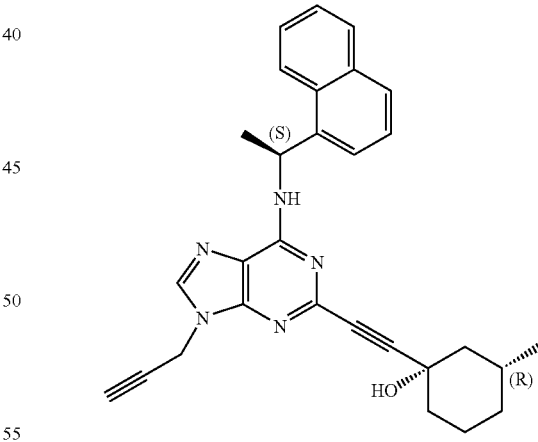

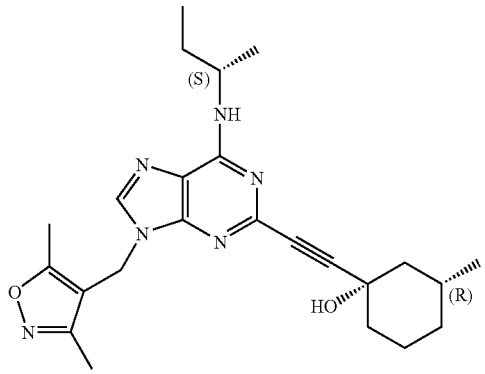

N6-[(s)-(+)-sec-Butyl]-9-(3,5-dimethyl-isoxazol-4-ylmethyl)-2-{2-[1(S)-hydroxy-3(R)-methyl-1-cyclohexyl]ethyn-1-yl}adenine (33). Using the representative procedure for N9-alkylation above N6-[(S)-(+)-sec-butyl]-2-{2-[1(S)-hydroxy-3(R)-methyl-1-cyclohexyl]ethyn-1-yl}-N6-(3-pen- 2-{2-[1(S)-Hydroxy-3(R)-methyl-1-cyclohexyl]ethyn-1-yl}-N6-[(s)-(−)-alpha-napthalen-1-yl-ethyl]-9-(propargyl) adenine (35). Using the representative procedure for N9-alkylation above 2-{2-[1(S)-hydroxy-1(R)-methyl-1-cyclohexyl]ethyn-1-yl}-N6-[(S)-(−)-alpha-napthalen-1-yl-ethyl]adenine (29 mg) gave 35 as a white solid: yield 22 mg, 70%. ¹H NMR (CD₃OD) δ 8.23 (m, 1H), 8.15 (s, 1H), 7.88–7.84 (m, 1H), 7.76 (d, 1H, J=8.4 Hz), 7.64 (d, 1H, J=7.0 Hz), 7.53–7.40 (m, 3H), 6.33 (br s, 1H), 5.00 (d, 2H, J=2.6 Hz), 2.96 (t, 1H, J=2.6 Hz), 2.08–1.99, 1.87–1.59, 1.45–1.33, 1.18–1.08, 0.95–0.70 (3×m, 12H). LRMS ESI (M+H⁺) 464.1.

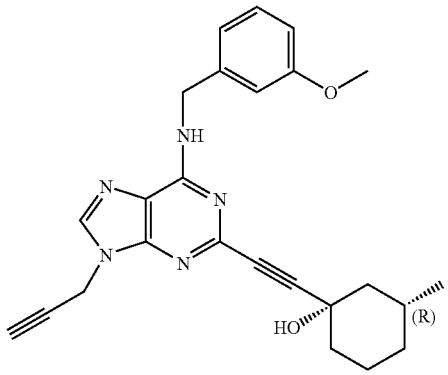

2-{2-[1(S)-Hydroxy-3(R)-methyl-1-cyclohexyl]ethyn-1-yl}-N6-(3-methoxybenzyl)-9-(propargyl)adenine (36). Using the representative procedure for N9-alkylation above 2-{2-[1(S)-Hydroxy-3(R)-methyl-1-cyclohexyl]ethyn-1-yl}-N6-(3-methoxybenzyl)adenine (48 mg) gave 36 as a white solid: yield 40 mg, 76%. $^1$H NMR (CD$_3$OD) δ 8.14 (s, 1H), 7.18 (t, 1H, J=7.9 Hz), 6.96–6.90 (m, 2H), 6.77 (m, 1H), 5.01 (d, 2H, J=2.6 Hz), 4.75 (br s, 2H), 3.74 (s, 3H), 2.97 (t, 1H, J=2.6 Hz), 2.13–2.04, 1.94–1.64, 1.48–1.37, 1.21–1.11, 0.96–0.77 (5×m, 12H). LRMS ESI (M+H⁺) 430.2.

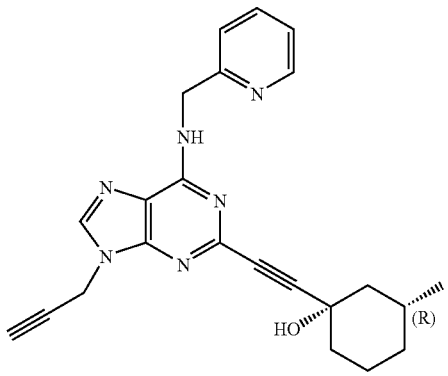

2-{2-[1(S)-Hydroxy-3(R)-methyl-1-cyclohexyl]ethyn-1-yl}-9-(propargyl)-N6-(pyridin-2-ylmethyl)adenine (37). Using the representative procedure for N9-alkylation above 2-{2-[1(S)-hydroxy-3(R)-methyl-1-cyclohexyl]ethyn-1-yl}-N6-(pyridin-2-ylmethyl)adenine (29 mg) gave 37 as a white solid: yield 27 mg, 84%. $^1$H NMR (CD$_3$OD) δ 8.49 (d, 1H, J=4.4 Hz), 8.20 (s, 1H), 7.76 (dt, 1H, J=1.8 Hz, J=7.7 Hz), 7.43 (d, 1H, J=7.9 Hz), 7.29 (m, 1H), 5.04 (d, 2H, J=2.6 Hz), 4.91 (br s, 2H), 2.98 (t, 1H, J=2.6 Hz), 2.10–2.03, 1.90–1.63, 1.47–1.36, 1.20–1.10, 0.96–0.73 (5×m, 12H). LRMS ESI (M+H⁺) 401.2.

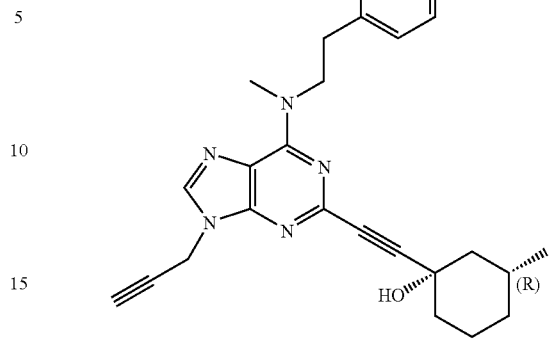

2-{2-[1(S)-Hydroxy-3(R)-methyl-1-cyclohexyl]ethyn-1-yl}-N6-[(methyl)(2-phenethyl)]-9-(propargyl)adenine (38). Using the representative procedure for N9-alkylation above 2-{2-[1(S)-hydroxy-3(R)-methyl-1-cyclohexyl]ethyn-1-yl}-N6-[(methyl)(2-phenethyl)]adenine (54 mg) gave 38 as a white solid: yield 47 mg, 79%. $^1$H NMR (CD$_3$OD) δ 8.09 (s, 1H), 7.30–7.11 (m, 5H), 5.00 (d, 2H, J=2.6 Hz), 4.19 (br s, 2H), 3.35 (br s, 3H), 2.98–2.91 (m, 3H), 2.14–2.06, 1.96–1.66, 1.50–1.39, 1.27–1.13, 0.98–0.80 (5×m, 12H). LRMS ESI (M+H⁺) 428.3.

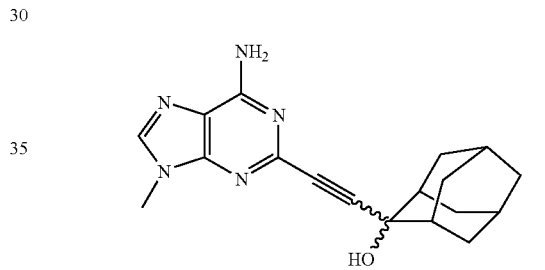

2-{2-[Hydroxy-adamantan-2-yl]ethyn-1-yl}-9-methyladenine (39). Using the representative procedure for N9-alkylation above 2-{2-[hydroxy-adamantan-2-yl]ethyn-1-yl}adenine (58 mg) gave 39 as a white solid: yield 39 mg, 64%. $^1$H NMR (CD$_3$OD) δ 8.08 (s, 1H), 3.80 (s, 3H), 2.37–2.22, 2.08–2.03, 1.89–1.74, 1.64–1.57 (4×m, 14H). LRMS ESI (M+H⁺) 324.2.

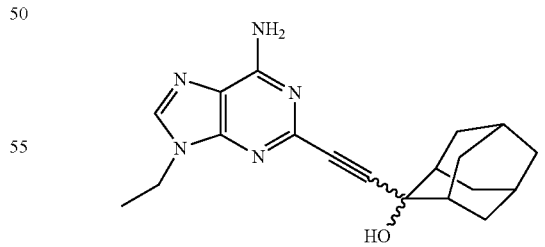

9-Ethyl-2-{2-[hydroxy-adamantan-2-yl]ethyn-1-yl}adenine (40). Using the representative procedure for N9-alkylation above 2-{2-[hydroxy-adamantan-2-yl]ethyn-1-yl}adenine (59 mg) gave 40 as a white solid: yield 42 mg, 65%. $^1$H NMR (CD$_3$OD) δ 8.15 (s, 1H), 4.25 (t, 2H, J=7.4 Hz), 2.36–2.22, 2.08–2.03, 1.89–1.74, 1.64–1.57 (4×m, 14H), 1.47 (t, 3H, J=7.3 Hz). LRMS ESI (M+H⁺) 338.2.

Hz), 2.36–2.22, 2.08–2.03, 1.90–1.74, 1.64–1.56, 1.35–1.23 (5×m, 28H), 0.87 (t, 3H, J=7.0 Hz). LRMS ESI (M+H⁺) 436.1.

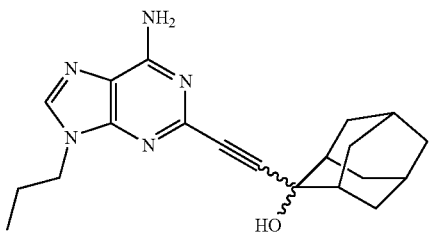

2-{2-[Hydroxy-adamantan-2-yl]ethyn-1-yl}-9-propyladenine (41). Using the representative procedure for N9-alkylation above 2-{2-[hydroxy-adamantan-2-yl]ethyn-1-yl}adenine (56 mg) gave 41 as a white solid: yield 46 mg, 72%. ¹H NMR (CD₃OD) δ 8.13 (s, 1H), 4.17 (t, 2H, J=7.2 Hz), 2.36–2.22, 2.08–2.03, 1.92–1.74, 1.64–1.57 (4×m, 16H), 0.93 (t, 3H, J=7.5 Hz). LRMS ESI (M+H⁺) 352.2.

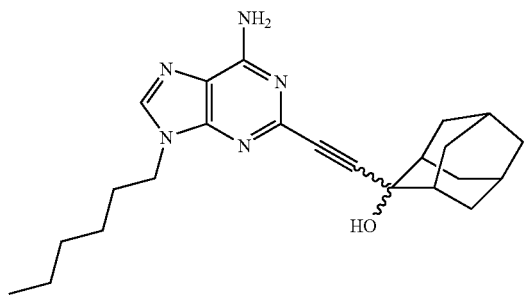

9-Hexyl-2-{2-[hydroxy-adamantan-2-yl]ethyn-1-yl}adenine (42). Using the representative procedure for N9-alkylation above 2-{2-[hydroxy-adamantan-2-yl]ethyn-1-yl}adenine (50 mg) gave 42 as a white solid: yield 43 mg, 68%. ¹H NMR (CD₃OD) δ 8.13 (s, 1H), 4.21 (t, 2H, J=7.0, 7.5 Hz), 2.37–2.22, 2.08–2.03, 1.91–1.74, 1.65–1.57, 1.37–1.27 (5×m, 22H), 0.88 (t, 3H). LRMS ESI (M+H⁺) 394.1.

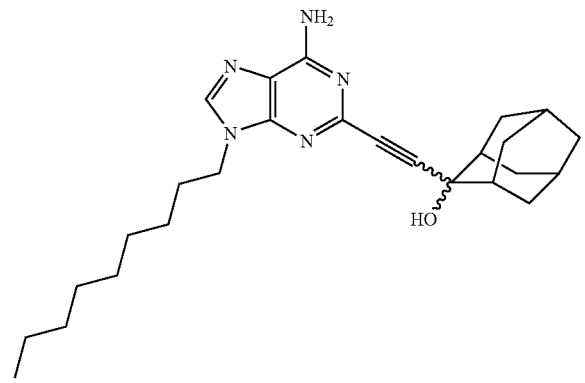

2-{2-[Hydroxy-adamantan-2-yl]ethyn-1-yl}-9-nonyladenine (43). Using the representative procedure for N9-alkylation above 2-{2-[hydroxy-adamantan-2-yl]ethyn-1-yl}adenine (43 mg) gave 43 as a white solid: yield 47 mg, 78%. ¹H NMR (CD₃OD) δ 8.13 (s, 1H), 4.20 (t, 2H, J=7.3

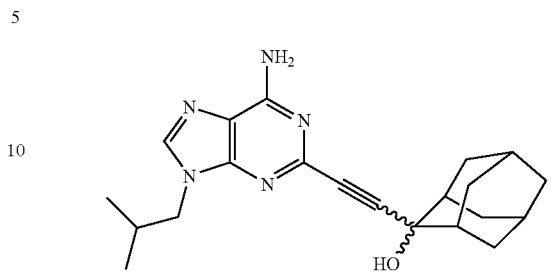

2-{2-[Hydroxy-adamantan-2-yl]ethyn-1-yl}-9-isobutyladenine (44). Using the representative procedure for N9-alkylation above 2-{2-[hydroxy-adamantan-2-yl]ethyn-1-yl}adenine (52 mg) gave 44 as a white solid: yield 46 mg, 75%. ¹H NMR (CD₃OD) δ 8.11 (s, 1H), 4.02 (d, 2H, J=7.5 Hz), 2.36–2.16, 2.08–2.03, 1.88–1.73, 1.64–1.56, (4×m, 15H), 0.91 (d, 6H, J=6.6 Hz). LRMS ESI (M+H⁺) 366.2.

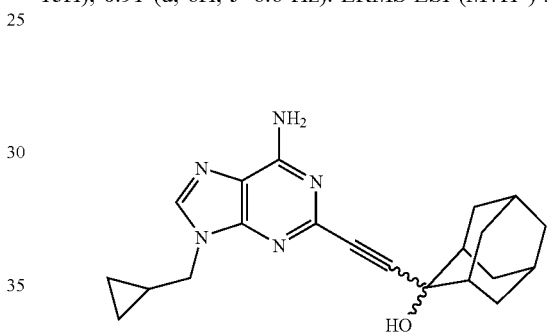

9-Cyclopropylmethyl-2-{2-[hydroxy-adamantan-2-yl]ethyn-1-yl}adenine (45). Using the representative procedure for N9-alkylation above 2-{2-[hydroxy-adamantan-2-yl]ethyn-1-yl}adenine (33 mg) gave 45 as a white solid: yield 11 mg, 28%. ¹H NMR (CD₃OD) δ 8.21 (s, 1H), 4.06 (d, 2H, J=7.3 Hz), 2.36–2.22, 2.08–2.03, 1.89–1.74, 1.65–1.57, (4×m, 14H), 1.42–1.27 (m, 1H), 0.65–0.58, 0.49–0.43 (2×m, 4H). LRMS ESI (M+H⁺) 364.2.

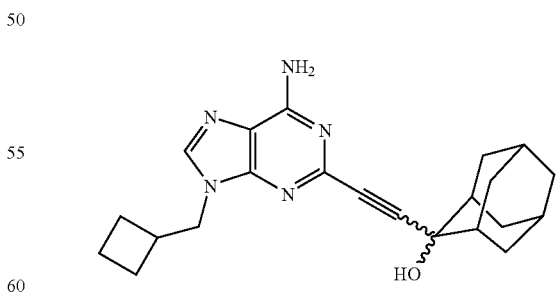

9-Cyclobutylmethyl-2-{2-[hydroxy-adamantan-2-yl]ethyn-1-yl}adenine (46). Using the representative procedure for N9-alkylation above 2-{2-[hydroxy-adamantan-2-yl]ethyn-1-yl}adenine (54 mg) gave 46 as a white crystalline solid: yield 21 mg, 32%. ¹H NMR (CD₃OD) δ 8.12 (s, 1H), 4.22 (d, 2H, J=7.5 Hz), 2.87 (quintet, 1H, J=7.7 Hz), 2.37–2.22, 2.09–1.74, 1.65–1.57, (3×m, 20H). LRMS ESI (M+H$^+$) 378.2.

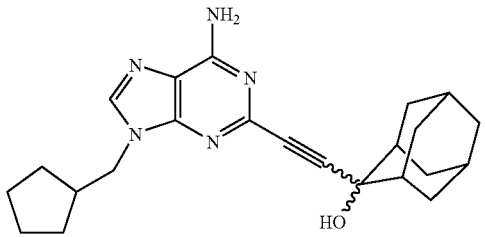

9-Cyclopentylmethyl-2-{2-[hydroxy-adamantan-2-yl]ethyn-1-yl}adenine (47). 2-{2-[Hydroxy-adamantan-2-yl]ethyn-1-yl}adenine (44 mg, 0.1422 mmol) was dissolved in DMF (20 mL) with heating. Anhydrous potassium carbonate (51 mg, 0.3690 mmol) and cyclopentylmethyl 4-methylbenzenesulfonate (54 mg, 0.2123 mmol) were added and the mixture stirred at 70° C. for 72 h. Extra cyclopentylmethyl 4-methylbenzenesulfonate (82 mg, 0.3224 mmol) was added and stirring continued at 100° C. a further 4.5 h. The reaction mixture was adhered to silica and purified by column chromatography, eluting with a gradient of DCM/MeOH (0–6%) to afford the pure 47 as a white solid: yield 38 mg, 68%. 1H NMR (CD$_3$OD) δ 8.15 (s, 1H), 4.14 (d, 2H, J=7.7 Hz), 2.48 (quintet, 1H, J=7.5 Hz), 2.37–2.22, 2.08–2.02, 1.89–1.58, 1.37–1.24 (4×m, 22H). LRMS ESI (M+H$^+$) 392.0.

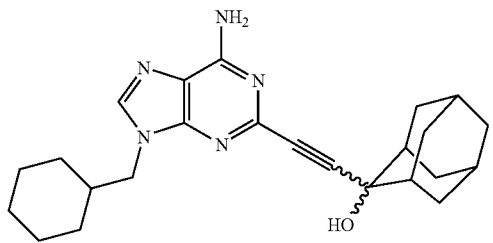

9-Cyclohexylmethyl-2-{2-[hydroxy-adamantan-2-yl]ethyn-1-yl}adenine (48). Using the representative procedure for N9-alkylation above 2-{2-[hydroxy-adamantan-2-yl]ethyn-1-yl}adenine (49 mg) gave 48 as a white solid: yield 45 mg, 70%. $^1$H NMR (CD$_3$OD) δ 8.10 (s, 1H), 4.04 (d, 2H, J=7.3Hz), 2.37–2.22, 2.09–2.03, 1.92–1.54, 1.31–0.96, (4×m, 25H). LRMS ESI (M+H$^+$) 406.3.

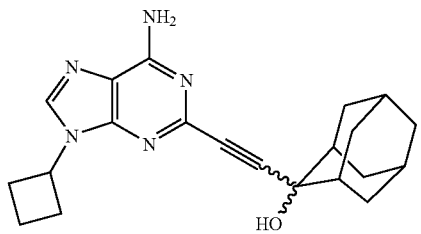

9-Cyclobutyl-2-{2-[hydroxy-adamantan-2-yl]ethyn-1-yl}adenine (49). Using the representative procedure for N9-alkylation above 2-{2-[hydroxy-adamantan-2-yl]ethyn-1-yl}adenine (34 mg) gave 49 as a white solid: yield 18 mg, 45%. $^1$H NMR (CD$_3$OD) δ 8.32 (s, 1H), 5.03 (m, 1H), 2.72–2.49, 2.38–2.22, 2.04–1.74, 1.64–1.57 (4×m, 20H). LRMS ESI (M+H$^+$) 364.2.

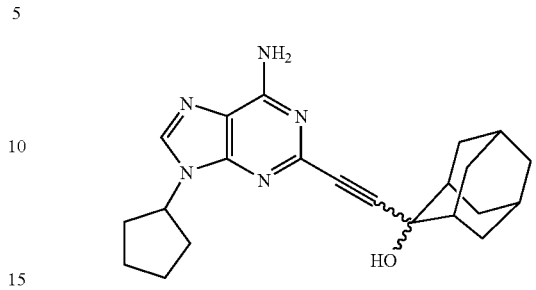

9-Cyclopentyl-2-{2-[hydroxy-adamantan-2-yl]ethyn-1-yl}adenine (50). Using the representative procedure for N9-alkylation above 2-{2-[hydroxy-adamantan-2-yl]ethyn-1-yl}adenine (473 mg) gave 50 as a white solid: yield 371 mg, 64%. $^1$H NMR (CD$_3$OD) δ 8.21 (s, 1H), 4.90 (m, 1H), 2.37–2.20, 2.08–1.73, 1.64–1.57 (4×m, 22H). LRMS ESI (M+H$^+$) 378.2.

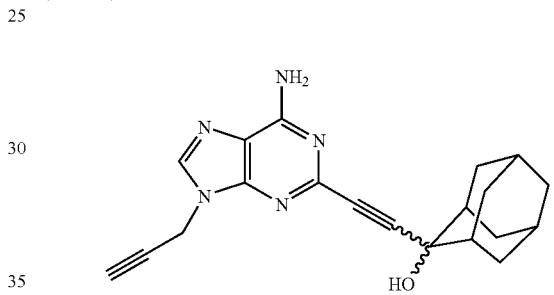

2-{2-[Hydroxy-adamantan-2-yl]ethyn-1-yl}-9-propargyl-adenine (51). Using the representative procedure for N9-alkylation above 2-{2-[hydroxy-adamantan-2-yl]ethyn-1-yl}adenine (510 mg) gave 51 as a white solid: yield 416 mg, 73%. $^1$H NMR (CD$_3$OD) δ 8.22 (s, 1H), 5.04 (d, 2H, J=2.6 Hz), 2.98 (t, 1H, J=2.5 Hz), 2.36–2.22, 2.08–2.03, 1.89–1.75, 1.65–1.57 (4×m, 14H). LRMS ESI (M+H$^+$) 348.2.

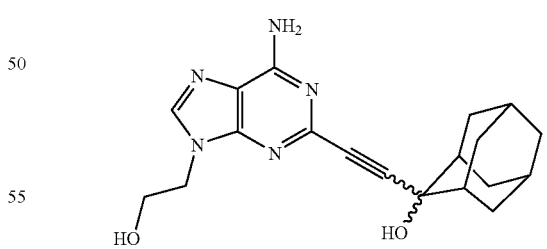

2-{2-[Hydroxy-adamantan-2-yl]ethyn-1-yl}-9-(2-hydroxyethyl)adenine (52). Using the representative procedure for N9-alkylation above 2-{2-[hydroxy-adamantan-2-yl]ethyn-1-yl}adenine (49 mg) gave 52 as a white solid: yield 21 mg, 38%. $^1$H NMR (CD$_3$OD) δ 8.12 (s, 1H), 4.31 (t, 2H, J=5.2 Hz), 3.87 (t, 2H, J=4.7 Hz), 2.36–2.21, 2.08–2.01, 1.89–1.73, 1.65–1.57 (4×m, 14H). LRMS ESI (M+H$^+$) 354.2.

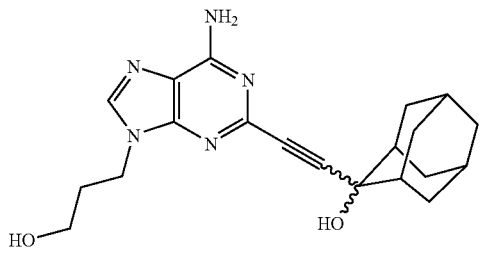

2-{2-[Hydroxy-adamantan-2-yl]ethyn-1-yl}-9-(2-hydroxypropyl)adenine (53). Using the representative procedure for N9-alkylation above 2-{2-[hydroxy-adamantan-2-yl]ethyn-1-yl}adenine (55 mg) gave 53 as a white solid: yield 37 mg, 57%. $^1$H NMR (CD$_3$OD) δ 8.13 (s, 1H), 4.32 (t, 2H, J=7.0 Hz), 3.55 (t, 2H, J=5.9, 6.2 Hz), 2.36–2.21, 2.11–2.00, 1.89–1.73, 1.65–1.57 (4×m, 16H). LRMS ESI (M+H$^+$) 368.2.

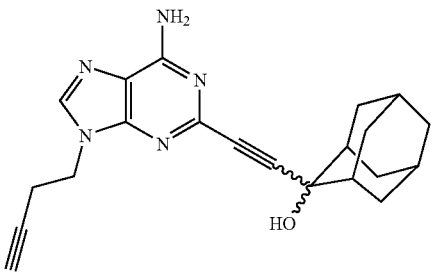

9-(But-3-ynyl)-2-{2-[hydroxy-adamantan-2-yl]ethyn-1-yl}adenine (62). Using the representative procedure for N9-alkylation above 2-{2-[hydroxy-adamantan-2-yl]ethyn-1-yl}adenine (52 mg) gave 62 as a white solid: yield 14 mg, 24%. $^1$H NMR (CD$_3$OD) δ 8.18 (s, 1H), 4.36 (t, 2H, J=6.6 Hz), 2.77 (dt, 2H, J=2.6, 6.6 Hz), 2.36 (t, 1H, J=2.6 Hz), 2.36–2.22, 2.08–2.03, 1.89–1.74, 1.64–1.57 (4×m, 16H). LRMS ESI (M+H$^+$) 362.0.

Isomer A

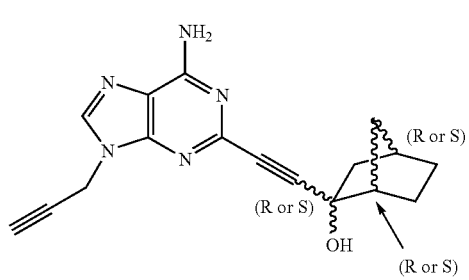

2-{2-[Hydroxy-norbornan-2-yl]ethyn-1-yl}-9-propargyladenine: Isomer A (60). Using the representative procedure for N9-alkylation above 2-{2-[hydroxy-norbornan-2-yl]ethyn-1-yl}adenine (42 mg) gave 60 as a white solid: yield 18 mg, 38%. $^1$H NMR (CD$_3$OD) δ 8.22 (s, 1H), 5.03 (s, 2H), 2.47–2.51 (m, 1H), 2.19–2.30 (m, 2H), 1.90–2.08 (m, 2H), 1.53–1.66 (m, 1H), 1.27–1.47 (m, 4H). LRMS ESI (M+H$^+$) 308.1.

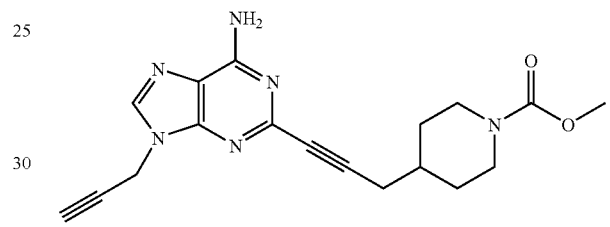

2-{3-[1-(Methoxycarbanoyl)piperidin-4-yl]propyn-1-yl}-9-propargyladenine (63). Using the representative procedure for N9-alkylation above 2-{3-[1-(methoxycarbanoyl)piperidin-4-yl]propyn-1-yl}adenine (53 mg) gave 63 as a white solid: yield 18 mg, 30%. $^1$H NMR (CD$_3$OD) δ 8.21 (s, 1H), 5.02 (s, 2H), 4.21–4.09 (m, 2H), 3.66 (s, 3H), 2.94–2.74 (m, 2H), 2.47–2.40 (m, 3H), 1.95–1.74 (m, 3H), 1.38–1.20 (m, 2H). LRMS ESI (M+H$^+$) 353.1.

The compounds in tables 1 to 7, or their pharmaceutically acceptable salts either as single stereoisomers or mixtures are representative examples of the invention.

Isomer B

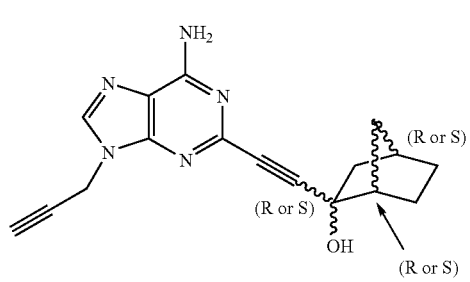

2-{2-[Hydroxy-norbornan-2-yl]ethyn-1-yl}-9-propargyladenine: Isomer B (61). Using the representative procedure for N9-alkylation above 2-{2-[hydroxy-norbornan-2-yl]ethyn-1-yl}adenine (31 mg) gave 61 as a white solid: yield 10 mg, 29%. $^1$H NMR (CD$_3$OD) δ 8.22 (s, 1H), 5.03 (s, 2H), 2.47–2.51 (m, 1H), 2.19–2.30 (m, 2H), 1.90–2.08 (m, 2H), 1.53–1.66 (m, 1H), 1.27–1.47 (m, 4H). LRMS ESI (M+H$^+$) 308.1.

TABLE 1

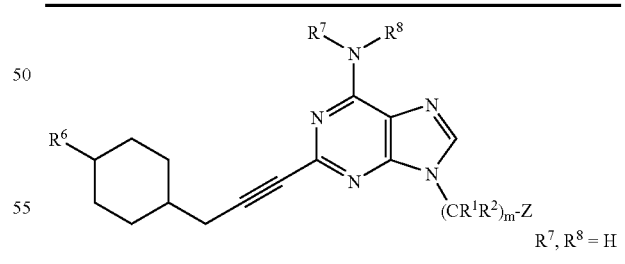

$R^7, R^8$ = H

| Compound | $(CR^1R^2)_m$-Z | $R^6$ |
|---|---|---|
| NC100 | Propargyl | CH$_2$OH |
| NC101 | c-Pentyl | CH$_2$OH |
| NC102 | Propargyl | CO$_2$H |
| NC103 | c-Pentyl | CO$_2$H |
| NC104 | Propargyl | CO$_2$Me |
| NC105 | c-Pentyl | CO$_2$Me |
| NC106 | Propargyl | CH$_2$OAc |
| NC107 | c-Pentyl | CH$_2$OAc |
| NC108 | Propargyl | CH$_2$N(CH$_3$)$_2$ |

TABLE 1-continued

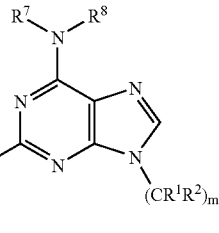

R⁷, R⁸ = H

| Compound | $(CR^1R^2)_m$-Z | $R^6$ |
|---|---|---|
| NC109 | c-Pentyl | $CH_2N(CH_3)_2$ |
| NC110 | Propargyl | $COOCH_2CH_2NHBoc$ |
| NC111 | c-Pentyl | $COOCH_2CH_2NHBoc$ |
| NC112 | Propargyl | $COOCH_2CH_2NH_2$ |
| NC113 | c-Pentyl | $COOCH_2CH_2NH_2$ |
| NC114 | Propargyl | $CONHCH_2CH_3$ |
| NC115 | c-Pentyl | $CONHCH_2CH_3$ |
| NC116 | Propargyl | $CONH_2$ |
| NC117 | c-Pentyl | $CONH_2$ |
| NC118 | Propargyl | CONHMe |
| NC119 | c-Pentyl | CONHMe |
| NC120 | Propargyl | Me, cis $CO_2Me$ |
| NC121 | c-Pentyl | Me, cis $CO_2Me$ |
| NC122 | Propargyl | Me, trans $CO_2Me$ |
| NC123 | c-Pentyl | Me, trans $CO_2Me$ |
| NC124 | Propargyl | $CH_2CH_3$ |
| NC125 | c-Pentyl | $CH_2CH_3$ |
| NC126 | Propargyl | H |
| NC127 | c-Pentyl | H |
| NC128 | Propargyl | $COCH_3$ |
| NC129 | c-Pentyl | $COCH_3$ |
| NC130 | Propargyl | $CHCH_3(OH)$ |
| NC131 | c-Pentyl | $CHCH_3(OH)$ |

TABLE 2

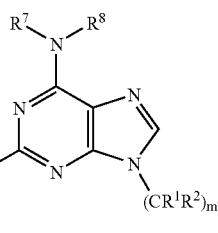

R⁷, R⁸ = H

| Compound | $(CR^1R^2)_m$-Z | $R^6$ |
|---|---|---|
| NC132 | Propargyl | H |
| NC133 | c-Pentyl | H |
| NC134 | Propargyl | $CO_2tBu$ |
| NC135 | c-Pentyl | $CO_2tBu$ |
| NC136 | Propargyl | $CO_2Et$ |
| NC137 | c-Pentyl | $CO_2Et$ |
| NC138 | Propargyl | $CO_2iBu$ |
| NC139 | c-Pentyl | $CO_2iBu$ |
| NC140 | Propargyl | $CO_2iPr$ |
| NC141 | c-Pentyl | $CO_2iPr$ |
| 63 | Propargyl | COMe |
| NC142 | c-Pentyl | COMe |
| NC143 | Propargyl | $COC(CH_3)_3$ |
| NC144 | c-Pentyl | $COC(CH_3)_3$ |
| NC145 | Propargyl | $COCH_2(CH_3)_3$ |
| NC146 | c-Pentyl | $COCH_2(CH_3)_3$ |
| NC147 | Propargyl | $C(O)N(CH_3)_2$ |
| NC148 | c-Pentyl | $C(O)N(CH_3)_2$ |
| NC149 | Propargyl | $C(O)N(CH_3)Et$ |
| NC150 | c-Pentyl | $C(O)N(CH_3)Et$ |
| NC142 | Propargyl | $C(O)N(CH_3)iPr$ |
| NC143 | c-Pentyl | $C(O)N(CH_3)iPr$ |

TABLE 2-continued

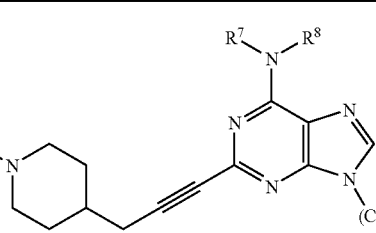

R⁷, R⁸ = H

| Compound | $(CR^1R^2)_m$-Z | $R^6$ |
|---|---|---|
| NC144 | Propargyl | $C(O)N(CH_3)iBu$ |
| NC145 | c-Pentyl | $C(O)N(CH_3)iBu$ |
| NC146 | Propargyl | $C(O)NH(CH_3)$ |
| NC147 | c-Pentyl | $C(O)NH(CH_3)$ |
| NC148 | Propargyl | $C(O)NH(Et)$ |
| NC149 | c-Pentyl | $C(O)NH(Et)$ |
| NC150 | Propargyl | $C(O)NH(iPr)$ |
| NC142 | c-Pentyl | $C(O)NH(iPr)$ |
| NC143 | Propargyl | $C(O)NH(iBu)$ |
| NC144 | c-Pentyl | $C(O)NH(iBu)$ |

TABLE 3

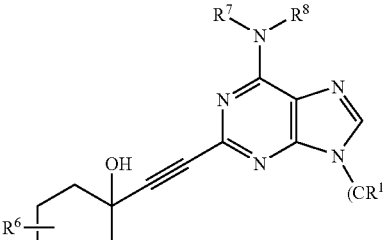

R⁷, R⁸ = H

| Compound | $(CR^1R^2)_m$-Z | $R^6$ |
|---|---|---|
| NC151 | Propargyl | H |
| NC152 | c-Pentyl | H |
| NC153 | Propargyl | 2-$CH_3$ |
| NC154 | c-Pentyl | 2-$CH_3$ |
| NC155 | Propargyl | 2-$C(CH_3)_3$ |
| NC156 | c-Pentyl | 2-$C(CH_3)_3$ |
| NC157 | Propargyl | 2-$C_6H_5$ |
| NC158 | c-Pentyl | 2-$C_6H_5$ |
| 2 | Propargyl | 3-$CH_3$ |
| 3 | c-Pentyl | 3-$CH_3$ |
| NC159 | Propargyl | 3-$(CH_3)_2$ |
| NC160 | c-Pentyl | 3-$(CH_3)_2$ |
| NC161 | Propargyl | 3-$CH_2CH_3$ |
| NC162 | c-Pentyl | 3-$CH_2CH_3$ |
| NC163 | Propargyl | 3-$(CH_3)_2$, 5-$(CH_3)_2$ |
| NC164 | c-Pentyl | 3-$(CH_3)_2$, 5-$(CH_3)_2$ |
| NC165 | Propargyl | 4-$CH_3$ |
| NC166 | c-Pentyl | 4-$CH_3$ |
| NC167 | Propargyl | 4-$C_2H_5$ |
| NC168 | c-Pentyl | 4-$C_2H_5$ |
| NC169 | Propargyl | 4-$C(CH_3)_3$ |
| NC170 | c-Pentyl | 4-$C(CH_3)_3$ |
| NC171 | Propargyl | 4-$C_6H_5$ |
| NC172 | c-Pentyl | 4-$C_6H_5$ |

TABLE 4

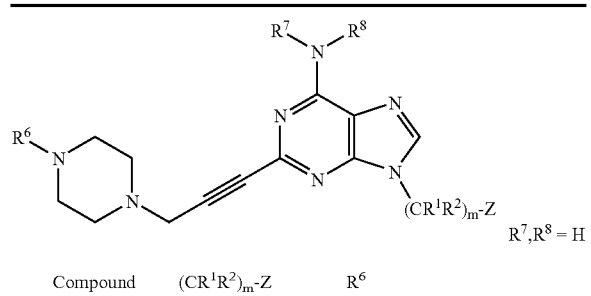

R⁷,R⁸ = H

| Compound | (CR¹R²)ₘ-Z | R⁶ |
|---|---|---|
| NC173 | Propargyl | H |
| NC174 | c-Pentyl | H |
| NC175 | Propargyl | cyclohexyl |
| NC176 | c-Pentyl | cyclohexyl |
| NC177 | Propargyl | CO₂Et |
| NC178 | c-Pentyl | CO₂Et |
| NC179 | Propargyl | CO₂tBu |
| NC180 | c-Pentyl | CO₂tBu |
| NC181 | Propargyl | COMe |
| NC182 | c-Pentyl | COMe |
| NC183 | Propargyl | CO₂iBu |
| NC184 | c-Pentyl | CO₂iBu |
| NC185 | Propargyl | 2-Pyrimidinyl |
| NC186 | c-Pentyl | 2-Pyrimidinyl |
| NC187 | Propargyl | COC(CH₃)₃ |
| NC188 | c-Pentyl | COC(CH₃)₃ |
| NC189 | Propargyl | COMe |
| NC190 | c-Pentyl | COMe |
| NC191 | Propargyl | COCH₂(CH₃)₃ |
| NC192 | c-Pentyl | COCH₂(CH₃)₃ |
| NC193 | Propargyl | COCH₃ |
| NC194 | c-Pentyl | COCH₃ |
| NC195 | Propargyl | C(O)N(CH₃)₂ |
| NC196 | c-Pentyl | C(O)N(CH₃)₂ |
| NC197 | Propargyl | C(O)N(CH₃)Et |
| NC198 | c-Pentyl | C(O)N(CH₃)Et |
| NC199 | Propargyl | C(O)N(CH₃)iPr |
| NC200 | c-Pentyl | C(O)N(CH₃)iPr |
| NC201 | Propargyl | C(O)N(CH₃)iBu |
| NC202 | c-Pentyl | C(O)N(CH₃)iBu |
| NC203 | Propargyl | C(O)NH(CH₃) |
| NC204 | c-Pentyl | C(O)NH(CH₃) |
| NC205 | Propargyl | C(O)NH(Et) |
| NC206 | c-Pentyl | C(O)NH(Et) |
| NC207 | Propargyl | C(O)NH(iPr) |
| NC208 | c-Pentyl | C(O)NH(iPr) |
| NC209 | Propargyl | C(O)NH(iBu) |
| NC210 | c-Pentyl | C(O)NH(iBu) |
| NC211 | Propargyl | CH₂OH |
| NC212 | c-Pentyl | CH₂OH |
| NC213 | Propargyl | CO₂H |
| NC214 | c-Pentyl | CO₂H |
| NC215 | Propargyl | CO₂Me |
| NC216 | c-Pentyl | CO₂Me |
| NC217 | Propargyl | CO₂Et |
| NC218 | c-Pentyl | CO₂Et |
| NC219 | Propargyl | CH₂OAc |
| NC220 | c-Pentyl | CH₂OAc |
| NC221 | Propargyl | CH₂N(CH₃)₂ |
| NC222 | c-Pentyl | CH₂N(CH₃)₂ |
| NC223 | Propargyl | COOCH₂CH₂NHBoc |
| NC224 | c-Pentyl | COOCH₂CH₂NHBoc |
| NC225 | Propargyl | COOCH₂CH₂NH₂ |
| NC226 | c-Pentyl | COOCH₂CH₂NH₂ |
| NC227 | Propargyl | CONHCH₂CH₃ |
| NC228 | c-Pentyl | CONHCH₂CH₃ |
| NC229 | Propargyl | CONH₂ |
| NC230 | c-Pentyl | CONH₂ |
| NC231 | Propargyl | CONHMe |
| NC232 | c-Pentyl | CONHMe |
| NC233 | Propargyl | CH₂CH₃ |
| NC234 | c-Pentyl | CH₂CH₃ |
| NC235 | Propargyl | COCH₃ |
| NC236 | c-Pentyl | COCH₃ |

TABLE 4-continued

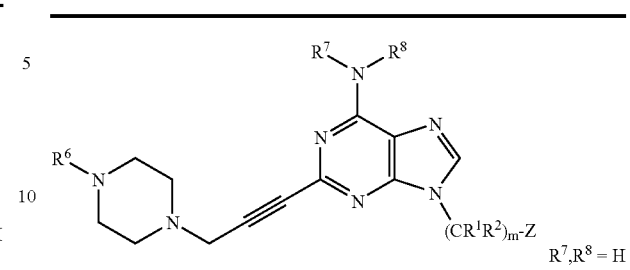

R⁷,R⁸ = H

| Compound | (CR¹R²)ₘ-Z | R⁶ |
|---|---|---|
| NC237 | Propargyl | CHCH₃(OH) |
| NC238 | c-Pentyl | CHCH₃(OH) |

TABLE 5

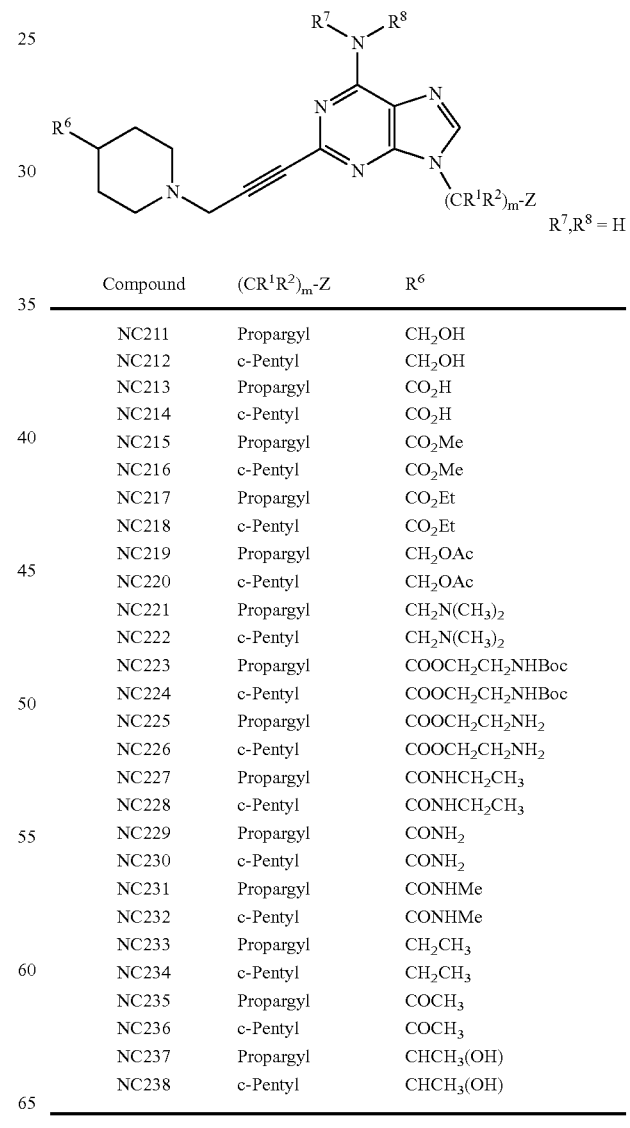

R⁷,R⁸ = H

| Compound | (CR¹R²)ₘ-Z | R⁶ |
|---|---|---|
| NC211 | Propargyl | CH₂OH |
| NC212 | c-Pentyl | CH₂OH |
| NC213 | Propargyl | CO₂H |
| NC214 | c-Pentyl | CO₂H |
| NC215 | Propargyl | CO₂Me |
| NC216 | c-Pentyl | CO₂Me |
| NC217 | Propargyl | CO₂Et |
| NC218 | c-Pentyl | CO₂Et |
| NC219 | Propargyl | CH₂OAc |
| NC220 | c-Pentyl | CH₂OAc |
| NC221 | Propargyl | CH₂N(CH₃)₂ |
| NC222 | c-Pentyl | CH₂N(CH₃)₂ |
| NC223 | Propargyl | COOCH₂CH₂NHBoc |
| NC224 | c-Pentyl | COOCH₂CH₂NHBoc |
| NC225 | Propargyl | COOCH₂CH₂NH₂ |
| NC226 | c-Pentyl | COOCH₂CH₂NH₂ |
| NC227 | Propargyl | CONHCH₂CH₃ |
| NC228 | c-Pentyl | CONHCH₂CH₃ |
| NC229 | Propargyl | CONH₂ |
| NC230 | c-Pentyl | CONH₂ |
| NC231 | Propargyl | CONHMe |
| NC232 | c-Pentyl | CONHMe |
| NC233 | Propargyl | CH₂CH₃ |
| NC234 | c-Pentyl | CH₂CH₃ |
| NC235 | Propargyl | COCH₃ |
| NC236 | c-Pentyl | COCH₃ |
| NC237 | Propargyl | CHCH₃(OH) |
| NC238 | c-Pentyl | CHCH₃(OH) |

TABLE 6

| Compound | (CR¹R²)$_m$-Z | R⁶ |
|---|---|---|
| NC239 | Propargyl | $CH_2OH$ |
| NC240 | c-Pentyl | $CH_2OH$ |
| NC241 | Propargyl | $CO_2H$ |
| NC242 | c-Pentyl | $CO_2H$ |
| NC243 | Propargyl | $CO_2Me$ |
| NC244 | c-Pentyl | $CO_2Me$ |
| NC245 | Propargyl | $CH_2OAc$ |
| NC246 | c-Pentyl | $CH_2OAc$ |
| NC247 | Propargyl | $CH_2N(CH_3)_2$ |
| NC248 | c-Pentyl | $CH_2N(CH_3)_2$ |
| NC249 | Propargyl | $COOCH_2CH_2NHBoc$ |
| NC250 | c-Pentyl | $COOCH_2CH_2NHBoc$ |
| NC251 | Propargyl | $COOCH_2CH_2NH_2$ |
| NC252 | c-Pentyl | $COOCH_2CH_2NH_2$ |
| NC253 | Propargyl | $CONHCH_2CH_3$ |
| NC254 | c-Pentyl | $CONHCH_2CH_3$ |
| NC255 | Propargyl | $CONH_2$ |
| NC256 | c-Pentyl | $CONH_2$ |
| NC257 | Propargyl | CONHMe |
| NC258 | c-Pentyl | CONHMe |
| NC259 | Propargyl | $CH_2CH_3$ |
| NC260 | c-Pentyl | $CH_2CH_3$ |
| NC261 | Propargyl | $COCH_3$ |
| NC262 | c-Pentyl | $COCH_3$ |
| NC263 | Propargyl | $CHCH_3(OH)$ |
| NC264 | c-Pentyl | $CHCH_3(OH)$ |

TABLE 7

| Compound | (CR¹R²)$_m$-Z | W | W' | R⁶ |
|---|---|---|---|---|
| NC265 | Propargyl | CH | CH | $CO_2Me$ |
| NC266 | c-Pentyl | CH | N | $CO_2Me$ |
| NC267 | Propargyl | N | CH | $CO_2Me$ |
| NC268 | c-Pentyl | N | N | $CO_2Me$ |
| NC269 | Propargyl | CH | CH | $CO_2Me$ |
| NC270 | c-Pentyl | CH | N | $CO_2Me$ |
| NC271 | Propargyl | N | CH | $CO_2Me$ |
| NC272 | c-Pentyl | N | N | $CO_2Me$ |
| NC273 | Propargyl | CH | CH | $CH_2OH$ |
| NC274 | c-Pentyl | CH | N | $CH_2OH$ |
| NC275 | Propargyl | N | CH | $CH_2OH$ |
| NC276 | c-Pentyl | N | N | $CH_2OH$ |
| NC277 | Propargyl | CH | CH | $CH_2OH$ |
| NC278 | c-Pentyl | CH | N | $CH_2OH$ |
| NC279 | Propargyl | N | CH | $CH_2OH$ |
| NC280 | c-Pentyl | N | N | $CH_2OH$ |
| NC281 | Propargyl | CH | CH | $CO_2H$ |
| NC282 | c-Pentyl | CH | N | $CO_2H$ |
| NC283 | Propargyl | N | CH | $CO_2H$ |
| NC284 | c-Pentyl | N | N | $CO_2H$ |
| NC285 | Propargyl | CH | CH | $CO_2H$ |
| NC286 | c-Pentyl | CH | N | $CO_2H$ |
| NC287 | Propargyl | N | CH | $CO_2H$ |
| NC288 | c-Pentyl | N | N | $CO_2H$ |
| NC289 | Propargyl | CH | CH | $CH_2OAc$ |
| NC290 | c-Pentyl | CH | N | $CH_2OAc$ |
| NC291 | Propargyl | N | CH | $CH_2OAc$ |
| NC292 | c-Pentyl | N | N | $CH_2OAc$ |
| NC293 | Propargyl | CH | CH | $CH_2OAc$ |
| NC294 | c-Pentyl | CH | N | $CH_2OAc$ |
| NC295 | Propargyl | N | CH | $CH_2OAc$ |
| NC296 | c-Pentyl | N | N | $CH_2OAc$ |
| NC297 | Propargyl | CH | CH | $CONH_2$ |
| NC298 | c-Pentyl | CH | N | $CONH_2$ |
| NC299 | Propargyl | N | CH | $CONH_2$ |
| NC300 | c-Pentyl | N | N | $CONH_2$ |
| NC301 | Propargyl | CH | CH | $CONH_2$ |
| NC302 | c-Pentyl | CH | N | $CONH_2$ |
| NC303 | Propargyl | N | CH | $CONH_2$ |
| NC304 | c-Pentyl | N | N | $CONH_2$ |
| NC305 | Propargyl | CH | CH | CONHMe |
| NC306 | c-Pentyl | CH | N | CONHMe |
| NC307 | Propargyl | N | CH | CONHMe |
| NC308 | c-Pentyl | N | N | CONHMe |
| NC309 | Propargyl | CH | CH | CONHMe |
| NC310 | c-Pentyl | CH | N | CONHMe |
| NC311 | Propargyl | N | CH | CONHMe |
| NC312 | c-Pentyl | N | N | CONHMe |
| NC313 | Propargyl | CH | CH | $CO_2tBu$ |
| NC314 | c-Pentyl | CH | N | $CO_2tBu$ |
| NC315 | Propargyl | N | CH | $CO_2tBu$ |
| NC316 | c-Pentyl | N | N | $CO_2tBu$ |
| NC317 | Propargyl | CH | CH | $CO_2tBu$ |
| NC318 | c-Pentyl | CH | N | $CO_2tBu$ |
| NC319 | Propargyl | N | CH | $CO_2tBu$ |
| NC320 | c-Pentyl | N | N | $CO_2tBu$ |
| NC321 | Propargyl | CH | CH | $CO_2Et$ |
| NC322 | c-Pentyl | CH | N | $CO_2Et$ |
| NC323 | Propargyl | N | CH | $CO_2Et$ |
| NC324 | c-Pentyl | N | N | $CO_2Et$ |
| NC325 | Propargyl | CH | CH | $CO_2Et$ |
| NC326 | c-Pentyl | CH | N | $CO_2Et$ |
| NC327 | Propargyl | N | CH | $CO_2Et$ |
| NC328 | c-Pentyl | N | N | $CO_2Et$ |
| NC329 | Propargyl | CH | CH | $CO_2iBu$ |
| NC330 | c-Pentyl | CH | N | $CO_2iBu$ |
| NC331 | Propargyl | N | CH | $CO_2iBu$ |
| NC332 | c-Pentyl | N | N | $CO_2iBu$ |
| NC333 | Propargyl | CH | CH | $CO_2iBu$ |
| NC334 | c-Pentyl | CH | N | $CO_2iBu$ |
| NC335 | Propargyl | N | CH | $CO_2iBu$ |
| NC336 | c-Pentyl | N | N | $CO_2iBu$ |
| NC337 | Propargyl | CH | CH | $CO_2iPr$ |
| NC338 | c-Pentyl | CH | N | $CO_2iPr$ |
| NC339 | Propargyl | N | CH | $CO_2iPr$ |
| NC340 | c-Pentyl | N | N | $CO_2iPr$ |
| NC341 | Propargyl | CH | CH | $CO_2iPr$ |
| NC342 | c-Pentyl | CH | N | $CO_2iPr$ |
| NC343 | Propargyl | N | CH | $CO_2iPr$ |

TABLE 7-continued

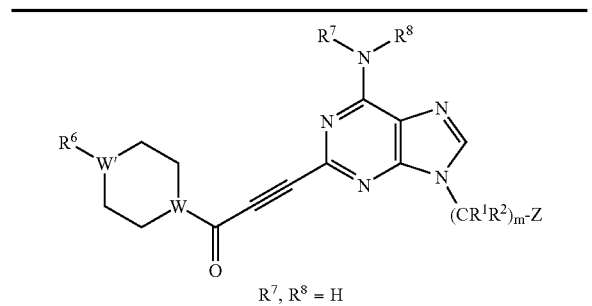

$R^7, R^8 = H$

| Compound | $(CR^1R^2)_m$-Z | W | W' | $R^6$ |
|---|---|---|---|---|
| NC344 | c-Pentyl | N | N | $CO_2iPr$ |
| NC345 | Propargyl | CH | CH | COMe |
| NC346 | c-Pentyl | CH | N | COMe |
| NC347 | Propargyl | N | CH | COMe |
| NC348 | c-Pentyl | N | N | COMe |
| NC349 | Propargyl | CH | CH | COMe |
| NC350 | c-Pentyl | CH | N | COMe |
| NC351 | Propargyl | N | CH | COMe |
| NC352 | c-Pentyl | N | N | COMe |
| NC353 | Propargyl | CH | CH | $COC(CH_3)_3$ |
| NC354 | c-Pentyl | CH | N | $COC(CH_3)_3$ |
| NC355 | Propargyl | N | CH | $COC(CH_3)_3$ |
| NC356 | c-Pentyl | N | N | $COC(CH_3)_3$ |
| NC357 | Propargyl | CH | CH | $COC(CH_3)_3$ |
| NC358 | c-Pentyl | CH | N | $COC(CH_3)_3$ |
| NC359 | Propargyl | N | CH | $COC(CH_3)_3$ |
| NC360 | c-Pentyl | N | N | $COC(CH_3)_3$ |
| NC361 | Propargyl | CH | CH | $COCH_2(CH_3)_3$ |
| NC362 | c-Pentyl | CH | N | $COCH_2(CH_3)_3$ |
| NC363 | Propargyl | N | CH | $COCH_2(CH_3)_3$ |
| NC364 | c-Pentyl | N | N | $COCH_2(CH_3)_3$ |
| NC365 | Propargyl | CH | CH | $COCH_2(CH_3)_3$ |
| NC366 | c-Pentyl | CH | N | $COCH_2(CH_3)_3$ |
| NC367 | Propargyl | N | CH | $COCH_2(CH_3)_3$ |
| NC368 | c-Pentyl | N | N | $COCH_2(CH_3)_3$ |
| NC369 | Propargyl | CH | CH | $C(O)N(CH_3)_2$ |
| NC370 | c-Pentyl | CH | N | $C(O)N(CH_3)_2$ |
| NC371 | Propargyl | N | CH | $C(O)N(CH_3)_2$ |
| NC372 | c-Pentyl | N | N | $C(O)N(CH_3)_2$ |
| NC373 | Propargyl | CH | CH | $C(O)N(CH_3)_2$ |
| NC374 | c-Pentyl | CH | N | $C(O)N(CH_3)_2$ |
| NC375 | Propargyl | N | CH | $C(O)N(CH_3)_2$ |
| NC376 | c-Pentyl | N | N | $C(O)N(CH_3)_2$ |
| NC377 | Propargyl | CH | CH | $C(O)N(CH_3)Et$ |
| NC378 | c-Pentyl | CH | N | $C(O)N(CH_3)Et$ |
| NC379 | Propargyl | N | CH | $C(O)N(CH_3)Et$ |
| NC380 | c-Pentyl | N | N | $C(O)N(CH_3)Et$ |
| NC381 | Propargyl | CH | CH | $C(O)N(CH_3)Et$ |
| NC382 | c-Pentyl | CH | N | $C(O)N(CH_3)Et$ |
| NC383 | Propargyl | N | CH | $C(O)N(CH_3)Et$ |
| NC384 | c-Pentyl | N | N | $C(O)N(CH_3)Et$ |
| NC385 | Propargyl | CH | CH | $C(O)N(CH_3)iPr$ |
| NC386 | c-Pentyl | CH | N | $C(O)N(CH_3)iPr$ |
| NC387 | Propargyl | N | CH | $C(O)N(CH_3)iPr$ |
| NC388 | c-Pentyl | N | N | $C(O)N(CH_3)iPr$ |
| NC389 | Propargyl | CH | CH | $C(O)N(CH_3)iPr$ |
| NC390 | c-Pentyl | CH | N | $C(O)N(CH_3)iPr$ |
| NC391 | Propargyl | N | CH | $C(O)N(CH_3)iPr$ |
| NC392 | c-Pentyl | N | N | $C(O)N(CH_3)iPr$ |
| NC393 | Propargyl | CH | CH | $C(O)N(CH_3)iBu$ |
| NC394 | c-Pentyl | CH | N | $C(O)N(CH_3)iBu$ |
| NC395 | Propargyl | N | CH | $C(O)N(CH_3)iBu$ |
| NC396 | c-Pentyl | N | N | $C(O)N(CH_3)iBu$ |
| NC397 | Propargyl | CH | CH | $C(O)N(CH_3)iBu$ |
| NC398 | c-Pentyl | CH | N | $C(O)N(CH_3)iBu$ |
| NC399 | Propargyl | N | CH | $C(O)N(CH_3)iBu$ |
| NC400 | c-Pentyl | N | N | $C(O)N(CH_3)iBu$ |
| NC401 | Propargyl | CH | CH | C(O)NH(Et) |
| NC402 | c-Pentyl | CH | N | C(O)NH(Et) |
| NC403 | Propargyl | N | CH | C(O)NH(Et) |
| NC404 | c-Pentyl | N | N | C(O)NH(Et) |
| NC405 | Propargyl | CH | CH | C(O)NH(Et) |

TABLE 7-continued

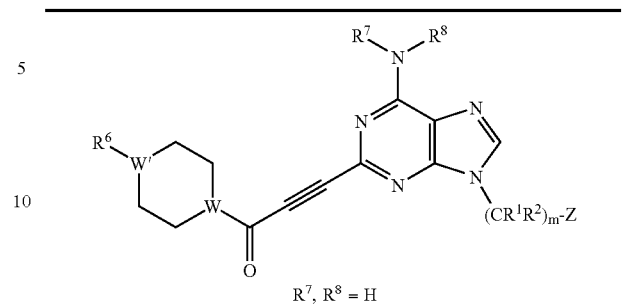

$R^7, R^8 = H$

| Compound | $(CR^1R^2)_m$-Z | W | W' | $R^6$ |
|---|---|---|---|---|
| NC406 | c-Pentyl | CH | N | C(O)NH(Et) |
| NC407 | Propargyl | N | CH | C(O)NH(Et) |
| NC408 | c-Pentyl | N | N | C(O)NH(Et) |
| NC409 | Propargyl | CH | CH | C(O)NH(iPr) |
| NC410 | c-Pentyl | CH | N | C(O)NH(iPr) |
| NC411 | Propargyl | N | CH | C(O)NH(iPr) |
| NC412 | c-Pentyl | N | N | C(O)NH(iPr) |
| NC413 | Propargyl | CH | CH | C(O)NH(iPr) |
| NC414 | c-Pentyl | CH | N | C(O)NH(iPr) |
| NC415 | Propargyl | N | CH | C(O)NH(iPr) |
| NC416 | c-Pentyl | N | N | C(O)NH(iPr) |
| NC417 | Propargyl | CH | CH | C(O)NH(iBu) |
| NC418 | c-Pentyl | CH | N | C(O)NH(iBu) |
| NC419 | Propargyl | N | CH | C(O)NH(iBu) |
| NC420 | c-Pentyl | N | N | C(O)NH(iBu) |
| NC421 | Propargyl | CH | CH | C(O)NH(iBu) |
| NC422 | c-Pentyl | CH | N | C(O)NH(iBu) |
| NC423 | Propargyl | N | CH | C(O)NH(iBu) |
| NC424 | c-Pentyl | N | N | C(O)NH(iBu) |
| NC425 | Propargyl | CH | CH | $CH_2OCOCH_3$ |
| NC426 | c-Pentyl | CH | N | $CH_2OCOCH_3$ |
| NC427 | Propargyl | N | CH | $CH_2OCOCH_3$ |
| NC428 | c-Pentyl | N | N | $CH_2OCOCH_3$ |
| NC429 | Propargyl | CH | CH | $CH_2OCOCH_3$ |
| NC430 | c-Pentyl | CH | N | $CH_2OCOCH_3$ |
| NC431 | Propargyl | N | CH | $CH_2OCOCH_3$ |
| NC432 | c-Pentyl | N | N | $CH_2OCOCH_3$ |
| NC433 | Propargyl | CH | CH | $CH_2OCOEt$ |
| NC434 | c-Pentyl | CH | N | $CH_2OCOEt$ |
| NC435 | Propargyl | N | CH | $CH_2OCOEt$ |
| NC436 | c-Pentyl | N | N | $CH_2OCOEt$ |
| NC437 | Propargyl | CH | CH | $CH_2OCOEt$ |
| NC438 | c-Pentyl | CH | N | $CH_2OCOEt$ |
| NC439 | Propargyl | N | CH | $CH_2OCOEt$ |
| NC440 | c-Pentyl | N | N | $CH_2OCOEt$ |
| NC441 | Propargyl | CH | CH | $CH_2OCOiPr$ |
| NC442 | c-Pentyl | CH | N | $CH_2OCOiPr$ |
| NC443 | Propargyl | N | CH | $CH_2OCOiPr$ |
| NC444 | c-Pentyl | N | N | $CH_2OCOiPr$ |
| NC445 | Propargyl | CH | CH | $CH_2OCOiPr$ |
| NC446 | c-Pentyl | CH | N | $CH_2OCOiPr$ |
| NC447 | Propargyl | N | CH | $CH_2OCOiPr$ |
| NC448 | c-Pentyl | N | N | $CH_2OCOiPr$ |
| NC449 | Propargyl | CH | CH | $CH_2OCOiBu$ |
| NC450 | c-Pentyl | CH | N | $CH_2OCOiBu$ |
| NC451 | Propargyl | N | CH | $CH_2OCOiBu$ |
| NC452 | c-Pentyl | N | N | $CH_2OCOiBu$ |
| NC453 | Propargyl | CH | CH | $CH_2OCOiBu$ |
| NC454 | c-Pentyl | CH | N | $CH_2OCOiBu$ |
| NC455 | Propargyl | N | CH | $CH_2OCOiBu$ |
| NC456 | c-Pentyl | N | N | $CH_2OCOiBu$ |

Evaluation of Novel $A_{2A}$ Antagonists in Four Mouse Models of PD: The $A_{2A}$ Receptor Antagonist ATL-2 Enhances Motor Function in a Dose-dependent Manner in Normal and Dopamine-depleted Mice.

In the set of experiments, we perform a dose response study of ATL-2 in stimulating motor activity in normal mice, and then we further extend this to dopamine-depleted mice. Adult male mice are habituated for 120 minutes and treated (i.p.) with saline or varying doses of compound, and their locomotor activity recorded for 120 minutes.

In a second set of experiments, we utilize the MPTP treatment paradigm to create animal model of PD by severely depleting dopamine in mice. We use a single MPTP treatment paradigm (40 mg/kg) which has been reproducibly reducing dopamine to 30–40% of normal dopamine contents in striatum in our previous studies.[35,74] Adult male mice (~25 mg/kg) are treated with single dose of MPTP (40 mg/kg). Thirty minutes after the MPTP treatment, mice are injected (i.p.) with vehicle or compounds of the invention at the same doses discussed above. Their motor activity is recorded for 180 minutes.

Results: Based on our previous experiments with other $A_{2A}R$ antagonists and our pilot study, we observe the maximal stimulant dose as well as sub-threshold doses of ATL compounds in normal and MPTP-treated mice. Without being bound by any theory, it is proposed that motor stimulant effect may manifest best in dopamine-depleted animals than normal animals, indicating that $A_{2A}R$ antagonists preferentially act at the $A_{2A}R$ in a PD condition to stimulate motor activity.

$A_{2A}$ receptor antagonists synergize with L-dopa to stimulate motor activity in dopamine-depleted mice.

We further tested the ability of these compounds to synergistically enhance motor function in conjunction with L-dopa, the standard therapy. Mice are injected (i.p.) with MPTP at a dose (1–2.5 mg/kg) that markedly decreases striatal dopamine levels. Thirty minutes later (when the mice exhibit an immobility), the mice are then randomly assigned to the following different treatment groups (n=10): (1) L-dopa (25 mg/kg); (2) ATL-2 (0.3, 1, 3, and 10 mg/kg), and (3) L-dopa (25 mg/kg)+ATL-2 (0.3, 1, 3, and 10 mg/kg). Locomotor behavior is monitored for 120 min before and after the treatment.

Results: Based on the Preliminary Results and on the known feature of other $A_{2A}R$ antagonists, a synergistic effect of ATL-2 with L-dopa in stimulating locomotor activity in dopamine-depleted mice is observed. This synergistic effect of ATL-2 and L-dopa is exhibited in a left-shift of the dose-response curve.

$A_{2A}$ Antagonists Potently and Specifically Attenuate MPTP-induced Neurotoxicity by Inhibiting MPTP Metabolism.

C57Bl/6 mice (n=10–12 mice per group) are pretreated with the $A_{2A}$ antagonist ATL-2 (0.3, 1.0, 3.0 and 10.0 mg/kg, i.p) 5 min prior to each of four MPTP (40 mg/kg) injections at 2 hr intervals. These doses are selected based on our preliminary results (with CSC) and on motor and neuroprotective effects (against ischemia) by SCH58261 and DPCPX. The specificities for the $A_{2A}R$ in these dose ranges of ATL-2 have been confirmed using $A_{2A}$ KO mice. Seven days after the MPTP (±CSC, SCH58261 or CPA) treatment, the striatum from one side are dissected out and processed for HPLC analysis of dopamine and DOPAC levels. The other half brain is quickly frozen for sectioning coronally through the striatum and substantial nigra. DAT binding density in striatum may be determined by receptor autoradiography using $^3$H-mazindol as a specific ligand. Quantitation of DAT ($^3$H-mazindol) binding autoradiography may be performed by densitometry analysis. The numbers of dopaminergic neurons may be determined by TH immunohistochemistry in the substantial nigra. Stereological methods may be used to estimate the absolute reduction in TH$^+$ nigral neurons in MPTP-treated WT mice and any attenuation in those pretreated with ATL-2. In the same sections, cell counts may also be performed for TH$^+$ neurons in the more medial VTA, which is less affected in MPTP treated mice as well as in PD.

Results: Guided by our preliminary results, neuroprotection in a dose-dependent manner (at least from 0.5 to 5 mg/kg range) may be observed. The potency of $A_{2A}$ antagonists for neuroprotection may be observed with their potency for motor stimulation and for possible attenuation of behavioral sensitization (see above). Similarly, the potency of CSC or SCH58261 for neuroprotection against MPTP may be compared to that for neuroprotection against ischemic injury and excitotoxicity. A significant difference in an $A_{2A}$ antagonist's potency in neuroprotection against MPTP and against ischemia or excitotoxicity may suggest different mechanisms and sites of action (e.g. glial versus neuronal compartments which may have different G-protein coupling mechanisms). On the other hand, the same potency of $A_{2A}$ antagonists for motor stimulation, neuroprotection and possibly delayed sensitization to L-dopa would suggest that the same type of $A_{2A}R$ is responsible for all these potential benefits of $A_{2A}$ antagonists in different animal models of PD.

$A_{2A}$ Antagonists Delay and $A_{2A}$ Agonists Accelerate L-dopa-induced Locomotor Sensitization in Unilateral 6-OHDA-lesioned Mice.

The ability of ATL-2 to modify the development of L-dopa-induced locomotor sensitization in hemiparkinsonian mice are tested. C57BL/6 mice (from the Jackson's lab, Bar Harbor, Mich.) are lesioned with 6-OHDA by unilateral intrastriatal using a standard lesioning protocol. Seven days after the 6-OHDA (or MPP$^+$) treatment, mice are injected with L-dopa (2.0 mg/kg, daily) for 14 days. Five min prior to each L-dopa treatment, the mice receive intraperitoneal pretreatment with: (1) vehicle, (2) ATL-2 (3 mg/kg) or (3) ATL-2 (10 mg/kg). In these dose ranges, the selective $A_{2A}$ antagonists have been shown to produce motor stimulant effects (see Preliminary Results). Rotational responses to L-dopa are recorded on the days 1, 3, 5, 7, 10 and 15. Following the behavioral measurement, mice may be sacrificed and their brains sectioned through striatum and substantia nigra. Striatal enkephalin mRNA levels are determined by in situ hybridization histochemistry. Similarly, DAT ($^3$H-mazindol) binding is measured by receptor autoradiography to ensure successful and equivalent lesions among different experimental groups.

Results: Based on our previous study with SCH58261 in this repeated L-dopa-induced sensitization model, ATL-2 delays or prevent the development of locomotor sensitization. The prevention or delayed appearance with L-dopa locomotor sensitization by co-injection of an $A_{2A}$ antagonist indicates an important role of the $A_{2A}R$ in the development of L-dopa-induced behavioral sensitization. Furthermore, this helps exclude the possibility that an attenuated behavioral sensitization to chronic L-dopa observed in $A_{2A}$ KO mice results from a developmental effect of $A_{2A}R$ deficiency. Thus combined genetic and pharmacological approaches provide the clearest assessment of the $A_{2A}R$'s role in the development of behavioral sensitization to L-dopa, and provides insights into its role in L-dopa-induced dyskinesia.

Methods

Animal Treatments and Catalepsy Behavioral Assessments:

WT and $A_{2A}$ KO mice (generated as above) as well as commercially procured C57Bl/6 mice (Taconic, N.Y.) may be used for this study. Since our pilot study and other reports [40, 88] indicate that animal age is a critical factor in determining the extent of an MPTP lesion, animal body weight around 25–30 grams (corresponding to approximately 10 weeks of age) is tightly controlled. The mice are housed in temperature and humidity-controlled rooms with a 24-hour 1:1 light:dark cycle. Adenosinergic and dopaminergic agents are injected at the volume of 0.1 ml/10 gram body weight of mice. Other adenosinergic and dopaminergic drugs are purchased from RBI (Natick, Mass.). From our previous work, we have adapted a special solvent (15% DMSO, 15% Alkamuls-EL 620 and 70% saline) for dissolving $A_{2A}$ antagonists, including CSC and SCH58261.

Catalepsy behavior may be induced by haloperidol (1 mg/kg, i.p.) or reserpine (5 mg/kg, i.p. see below). Catalepsy score may be determined by the bar and grid tests. For the bar test, both mouse forepaws are placed on a 6 cm-high horizontal bar (diameter 0.7 cm). In the grid test, mice are allowed to cling to a metal-framed vertical grid (1.3 cm squares). The latency from paw placement until the first complete removal of one paw from the support is measured (maximal test duration 180 sec). Upon the completion of behavioral assessment, mice are sacrificed and the brains are processed for neurochemical and histochemical analyses.

Dopamine Depletion by the Treatment with MPTP or 6-OHDA:

a) Intraperitoneal Injection of MPTP: The MPTP administration regimen (20 mg/kg×4 at 2 hr interval) has been shown to produce severe dopamine depletion (consistently greater than ~80% in our Preliminary Results FIGS. 6 and 7). Naive C57Bl/6 mice are pretreated with adenosine antagonists 5 min prior to MPTP treatment.

b) Intrastriatal Injection of 6-OHDA: Wild-type C57Bl/6 or A2AR mutant mice are anesthetized with Avertin and positioned in a stereotaxic frame. Three microliters of 6-OHDA (3 µg/µl) are injected into the left striatum (coordinates from bregma: AP+0.0, L+2.5.0, DV −4.4) via a infusion minipump over a 4 min period. Due to its photolability, 6-OHDA is dissolved in 0.01% ascorbic acid and injected under a light-protected environment.

c) Post-treatment Care: Dopamine-depleted mice may be continually monitored, and special care may be taken to maintain mouse body temperature with a heating blanket or warming lights. During the first 48 hours post-operation, mashed food pellets and water are provided to the mice inside the cage at floor-level for easy access.

Neurochemical Analysis:

(a) Measurements of Catecholamines and Indoleamines in Striatum by HPLC: To measure tissue catecholamine and indoleamine levels, mice are decapitated, their brains are removed rapidly, and striata are dissected out and frozen on dry ice. Striata are weighed frozen and then homogenized in 200 µl of 150 mM trichloroacetic acid containing 0.1 mM EDTA and 1 µM epinephrine (as an internal standard). Homogenates are centrifuged for 5 min at 15,000 g. The catecholamines in the supernatant are separated over a reverse-phase hydrophobic interaction C-18 HPLC column (Beckman, 5µ ODS) and measured using an electrochemical detector (ESA Coulochem 5100A) with electrodes set in series at oxidizing (+0.22 V) and then reducing (−0.35 V) potentials. Both the retention time and the ratio of oxidation to reduction currents for given sample peaks are compared against those for external standards to ensure proper identification of analytes.

(b) Stereologic quantitation of neuronal loss in substantia nigra: One week after lesioning, mice may be perfusion-fixed and their brains may be microtome-cut into 40 µm coronal free-floating sections. Every sixth section may be processed for TH immunohistochemistry using a 1:1,000 dilution of a polyclonal rabbit antiserum against rat TH (Eugene Tech. Intl., NJ). Immunostaining is completed using standard avidin-biotin procedures described previously [18,130]. A non-biased stereological technique is employed to quantify the effect of treatment on total TH+ nigra (pars compacta) cell counts as described previously [81]. All counts are performed by a single observer who is unaware of the treatment group at the time of neuronal estimates. Based on our pilot studies in WT mice MPP+ at this dose (3 µg/striatum) produced a ~40% loss of ipsilateral TH+ nigral neurons.

(c) A2A receptor binding autoradiography: Twenty micron striatal sections are preincubated for 5 minutes with ice-cold buffer (509 mM Tris-HCl, 5 mM KCl and 300 mM NaCl, pH 7.9) and then incubated for 60 minutes in the same buffer containing 6 nM 3H-SCH58261 (provided generously by Dr. E. Ongini) [131]. The slides are washed twice and then air-dried before exposure to Hyperfilm (Amersham, IL) for 2–4 weeks. The films are analyzed with a video-based image analysis system (MultiAnalyst; Biorad), and total striatal 3H-SCH58261 binding (fmol/mg tissue) is calculated using a tritium-labeled calibration standard [17,131].

Statistical Analysis

Single statistical comparisons of an A2AR KO group to its WT control are generally performed using a Student's t test, two-tailed. Comparison of more than two factors (e.g. genotype, drug treatment and time course) and their interactions are made using 2-way ANOVA followed by Newman-Keuls post hoc analysis. If data are not normally distributed, non-parametric tests (Kruskal-Wallis or Mann-Whitney U test) are used.

Vertebrate Animals. Mice are the only animals that are be used in experiments. The mice are monitored daily (co-investigators or technician) under the supervision of a staff veterinarian. In the majority of the experiments the mice are kept under SPF conditions with no more than 5 mice/cage of females and 4 mice/cage of males. All husbandry and veterinary care meets NIH and AAALAC standards for humane care for use of laboratory animals. In addition, because of daily observation of all animals, any moribund animal is humanely euthanized by $CO_2$.

Models of PD are used to investigate pre-clinical efficacy and pharmacokinetics of A2AAR antagonist. Because we have used these model in our laboratory, the model is now well characterized and the experimental manipulation of mice for these studies are well established.

REFERENCES

1. Hauser R A, Hubble J P, Truong D D. Randomized trial of the adenosine A(2A) receptor antagonist istradefylline in advanced PD. Neurology. 2003;61:297–303.
2. Lang A E, Lozano A M. Parkinson's disease. Second of two parts. N Engl J Med. 1998; 339:1130–1143.
3. Agid Y, Cervera P, Hirsch E, Javoy-Agid F, Lehericy S, Raisman R, Ruberg M. Biochemistry of Parkinson's disease 28 years later: a critical review. Mov Disord. 1989;4 Suppl 1:S126-S144.
4. Lang A E, Lozano A M. Parkinson's disease. Second of two parts. N Engl J Med. 1998;339:1130–1143.
5. Lang A E, Lozano A M. Parkinson's disease. First of two parts. N Engl J Med. 1998;339:1044–1053.
6. Obeso J A, Olanow C W, Nutt J G. Levodopa motor complications in Parkinson's disease. Trends Neurosci. 2000;23:S2-S7.

7. Bezard E, Brotchie J M, Gross C E. Pathophysiology of levodopa-induced dyskinesia: potential for new therapies. Nat Rev Neurosci. 2001;2:577–588.
8. Fahn S. The spectrum of levodopa-induced dyskinesias. Ann Neurol. 2000;47:S2-S9.
9. Fahn S. The spectrum of levodopa-induced dyskinesias. Ann Neurol. 2000;47:S2-S9.
10. Jenner P. Pathophysiology and biochemistry of dyskinesia: clues for the development of non-dopaminergic treatments. J Neurol. 2000;247 Suppl 2:II43-II50.
11. Melamed E, Offen D, Shirvan A, Djaldetti R, Barzilai A, Ziv I. Levodopa toxicity and apoptosis. Ann Neurol. 1998;44:S149-S154.
12. Jenner P. Pathophysiology and biochemistry of dyskinesia: clues for the development of non-dopaminergic treatments. J Neurol. 2000;247 Suppl 2:II43-II50.
13. Chen J F. The adenosine A(2A) receptor as an attractive target for Parkinson's disease treatment. Drug News Perspect. 2003;16:597–604.
14. Schwarzschild M A, Chen J F, Ascherio A. Caffeinated clues and the promise of adenosine A(2A) antagonists in PD. Neurology. 2002;58:1154–1160.
15. Ferre S, Fredholm B B, Morelli M, Popoli P, Fuxe K. Adenosine-dopamine receptor-receptor interactions as an integrative mechanism in the basal ganglia. Trends Neurosci. 1997;20:482–487.
16. Richardson P J, Gubitz A K, Freeman T C, Dixon A K. Adenosine receptor antagonists and Parkinson's disease: actions of the A2A receptor in the striatum. Adv Neurol. 1999;80:111–119.
17. Schwarzschild M A, Chen J F, Ascherio A. Caffeinated clues and the promise of adenosine A(2A) antagonists in PD. Neurology. 2002;58:1154–1160.
18. Fink J S, Weaver D R, Rivkees S A, Peterfreund R A, Pollack A E, Adler E M, Reppert S M. Molecular cloning of the rat A2 adenosine receptor: selective co-expression with D2 dopamine receptors in rat striatum. Brain Res Mol Brain Res. 1992;14:186–195.
19. Schiffmann S N, Jacobs O, Vanderhaeghen J J. Striatal restricted adenosine A2 receptor (RDC8) is expressed by enkephalin but not by substance P neurons: an in situ hybridization histochemistry study. J Neurochem. 1991; 57:1062–1067.
20. Schiffmann S N, Vanderhaeghen J J. Adenosine A2 receptors regulate the gene expression of striatopallidal and striatonigral neurons. J Neurosci. 1993;13:1080–1087.
21. Ferre S, Rubio A, Fuxe K. Stimulation of adenosine A2 receptors induces catalepsy. Neurosci Lett. 1991;130: 162–164.
22. Ferre S, Fuxe K, Von Euler G, Johansson B, Fredholm B B. Adenosine-dopamine interactions in the brain. Neurosci. 1992;51:501–512.
23. Fredholm B B, Battig K, Holmen J, Nehlig A, Zvartau E E. Actions of caffeine in the brain with special reference to factors that contribute to its widespread use. Pharmacol Rev. 1999;51:83–133.
24. Barraco R A, Martens K A, Parizon M, Normile H J. Adenosine A2a receptors in the nucleus accumbens mediate locomotor depression. Brain Res Bull. 1993;31:397–404.
25. Ferre S, Von Euler G, Johansson B, Fredholm B B, Fuxe K. Stimulation of high-affinity adenosine A2 receptors decreases the affinity of dopamine D2 receptors in rat striatal membranes. Proc Natl Acad Sci USA. 1991;88: 7238–7241.
26. Fuxe K, Ferre S, Zoli M, Agnati L F. Integrated events in central dopamine transmission as analyzed at multiple levels. Evidence for intramembrane adenosine A2A/dopamine D2 and adenosine A1/dopamine D1 receptor interactions in the basal ganglia. Brain Res Brain Res Rev. 1998;26:258–273.
27. Aoyama S, Kase H, Borrelli E. Rescue of locomotor impairment in dopamine D2 receptor-deficient mice by an adenosine A2A receptor antagonist. J Neurosci. 2000;20: 5848–5852.
28. Chen J F, Moratalla R, Impagnatiello F, Grandy D K, Cuellar B, Rubinstein M, Beilstein M A, Hackett E, Fink J S, Low M J, Ongini E, Schwarzschild M A. The role of the D(2) dopamine receptor (D(2)R) in A(2A) adenosine receptor (A(2A)R)-mediated behavioral and cellular responses as revealed by A(2A) and D(2) receptor knockout mice. Proc Natl Acad Sci USA. 2001;98:1970–1975.
29. Thompson R D, Secunda S, Daly J W, Olsson R A. N6,9-disubstituted adenines: potent, selective antagonists at the A1 adenosine receptor. J Med Chem. 1991;34: 2877–2882.
30. Mori A, Shindou T, Ichimura M, Nonaka H, Kase H. The role of adenosine A2a receptors in regulating GABAergic synaptic transmission in striatal medium spiny neurons. J Neurosci. 1996;16:605–611.
31. Richardson P J, Gubitz A K, Freeman T C, Dixon A K. Adenosine receptor antagonists and Parkinson's disease: actions of the A2A receptor in the striatum. Adv Neurol. 1999;80:111–119.
32. Svenningsson P, Le Moine C, Fisone G, Fredholm B B. Distribution, biochemistry and function of striatal adenosine A2A receptors. Prog Neurobiol. 1999;59:355–396.
33. Canals M, Marcellino D, Fanelli F, Ciruela F, de Benedetti P, Goldberg S R, Neve K, Fuxe K, Agnati L F, Woods A S, Ferre S, Lluis C, Bouvier M, Franco R. Adenosine A2A-dopamine D2 receptor-receptor heteromerization: qualitative and quantitative assessment by fluorescence and bioluminescence energy transfer. J Biol Chem. 2003; 278:46741–46749.
34. Fredholm B B, Battig K, Holmen J, Nehlig A, Zvartau E E. Actions of caffeine in the brain with special reference to factors that contribute to its widespread use [Review]. Pharmacol Rev. 1999;51:83–133.
35. Chen J F, Moratalla R, Impagnatiello F, Grandy D K, Cuellar B, Rubinstein M, Beilstein M A, Hackett E, Fink J S, Low M J, Ongini E, Schwarzschild M A. The role of the D(2) dopamine receptor (D(2)R) in A(2A) adenosine receptor (A(2A)R)-mediated behavioral and cellular responses as revealed by A(2A) and D(2) receptor knockout mice. Proc Natl Acad Sci USA. 2001;98:1970–1975.
36. Grondin R, Bedard P J, Hadj T A, Gregoire L, Mori A, Kase H. Antiparkinsonian effect of a new selective adenosine A2A receptor antagonist in MPTP-treated monkeys. Neurology. 1999;52:1673–1677.
37. Kanda T, Jackson M J, Smith L A, Pearce R K, Nakamura J, Kase H, Kuwana Y, Jenner P. Combined use of the adenosine A(2A) antagonist KW-6002 with L-DOPA or with selective D1 or D2 dopamine agonists increases antiparkinsonian activity but not dyskinesia in MPTP-treated monkeys. Exp Neurol. 2000;162:321–327.
38. Kanda T, Jackson M J, Smith L A, Pearce R K, Nakamura J, Kase H, Kuwana Y, Jenner P. Adenosine A2A antagonist: a novel antiparkinsonian agent that does not provoke dyskinesia in parkinsonian monkeys. Ann Neurol. 1998;43:507–513.

39. Kanda T, Tashiro T, Kuwana Y, Jenner P. Adenosine A2A receptors modify motor function in MPTP-treated common marmosets. Neuroreport. 1998;9:2857–2860.
40. Pinna A, Fenu S, Morelli M. Motor stimulant effects of the adenosine A(2A) receptor antagonist SCH 58261 do not develop tolerance after repeated treatments in 6-hydroxydopamine-lesioned rats. Synapse. 2001;39:233–238.
41. Pinna A, di Chiara G, Wardas J, Morelli M. Blockade of A2a adenosine receptors positively modulates turning behaviour and c-Fos expression induced by D1 agonists in dopamine-denervated rats. Eur J Neurosci. 1996;8:1176–1181.
42. Aoyama S, Kase H, Borrelli E. Rescue of locomotor impairment in dopamine D2 receptor-deficient mice by an adenosine A2A receptor antagonist. Journal of Neuroscience. 2000;20:5848–5852.
43. Grondin R, Bedard P J, Hadj T A, Gregoire L, Mori A, Kase H. Antiparkinsonian effect of a new selective adenosine A2A receptor antagonist in MPTP-treated monkeys. Neurology. 1999;52:1673–1677.
44. Kanda T, Jackson M J, Smith L A, Pearce R K, Nakamura J, Kase H, Kuwana Y, Jenner P. Adenosine A2A antagonist: a novel antiparkinsonian agent that does not provoke dyskinesia in parkinsonian monkeys. Ann Neurol. 1998;43:507–513.
45. Kanda T, Jackson M J, Smith L A, Pearce R K, Nakamura J, Kase H, Kuwana Y, Jenner P. Combined use of the adenosine A(2A) antagonist KW-6002 with L-DOPA or with selective D1 or D2 dopamine agonists increases antiparkinsonian activity but not dyskinesia in MPTP-treated monkeys. Exp Neurol. 2000;162:321–327.
46. Halldner L, Lozza G, Lindstrom K, Fredholm B B. Lack of tolerance to motor stimulant effects of a selective adenosine A(2A) receptor antagonist. Eur J Pharmacol. 2000;406:345–354.
47. Pinna A, Fenu S, Morelli M. Motor stimulant effects of the adenosine A(2A) receptor antagonist SCH 58261 do not develop tolerance after repeated treatments in 6-hydroxydopamine-lesioned rats. Synapse. 2001;39:233–238.
48. Kanda T, Jackson M J, Smith L A, Pearce R K, Nakamura J, Kase H, Kuwana Y, Jenner P. Combined use of the adenosine A(2A) antagonist KW-6002 with L-DOPA or with selective D1 or D2 dopamine agonists increases antiparkinsonian activity but not dyskinesia in MPTP-treated monkeys. Exp Neurol. 2000;162:321–327.
49. Fredduzzi S, Moratalla R, Monopoli A, Cuellar B, Xu K, Ongini E, Impagnatiello F, Schwarzschild M A, Chen J F. Persistent behavioral sensitization to chronic L-DOPA requires A2A adenosine receptors. J Neurosci. 2002;22:1054–1062.
50. Bibbiani F, Oh J D, Petzer J P, Castagnoli N, Jr., Chen J F, Schwarzschild M A, Chase TN. A2A antagonist prevents dopamine agonist-induced motor complications in animal models of Parkinson's disease. Exp Neurol. 2003;184:285–294.
51. Chen J F, Huang Z, Ma J, Zhu J, Moratalla R, Standaert D, Moskowitz M A, Fink J S, Schwarzschild M A. A(2A) adenosine receptor deficiency attenuates brain injury induced by transient focal ischemia in mice. J Neurosci. 1999;19:9192–9200.
52. Monopoli A, Casati C, Lozza G, Forlani A, Ongini E. Cardiovascular pharmacology of the A2A adenosine receptor antagonist, SCH 58261, in the rat. J Pharmacol Exp Ther. 1998;285:9–15.
53. Phillis J W. The effects of selective A1 and A2a adenosine receptor antagonists on cerebral ischemic injury in the gerbil. Brain Res. 1995;705:79–84.
54. Jones P A, Smith R A, Stone T W. Protection against hippocampal kainate excitotoxicity by intracerebral administration of an adenosine A2A receptor antagonist. Brain Res. 1998;800:328–335.
55. Jones P A, Smith R A, Stone T W. Protection against kainate-induced excitotoxicity by adenosine A2A receptor agonists and antagonists. Neuroscience. 1998;85:229–237.
56. Popoli P, Pintor A, Domenici M R, Frank C, Tebano M T, Pezzola A, Scarchilli L, Quarta D, Reggio R, Malchiodi-Albedi F, Falchi M, Massotti M. Blockade of striatal adenosine A2A receptor reduces, through a presynaptic mechanism, quinolinic acid-induced excitotoxicity: possible relevance to neuroprotective interventions in neurodegenerative diseases of the striatum. J Neurosci. 2002;22:1967–1975.
57. Dall'Igna O P, Porciuncula L O, Souza D O, Cunha R A, Lara D R, Dall'Igna O P. Neuroprotection by caffeine and adenosine A2A receptor blockade of beta-amyloid neurotoxicity. Br J Pharmacol. 2003;138:1207–1209.
58. Chen J F, Xu K, Petzer J P, Staal R, Xu Y H, Beilstein M, Sonsalla P K, Castagnoli K, Castagnoli N, Jr., Schwarzschild M A. Neuroprotection by caffeine and A(2A) adenosine receptor inactivation in a model of Parkinson's disease. J Neurosci. 2001;21:RC143.
59. Chen J F, Xu K, Petzer J P, Staal R, Xu Y H, Beilstein M, Sonsalla P K, Castagnoli K, Castagnoli N, Jr., Schwarzschild M A. Neuroprotection by caffeine and A(2A) adenosine receptor inactivation in a model of Parkinson's disease. J Neurosci. 2001;21:RC143.
60. Ikeda K, Kurokawa M, Aoyama S, Kuwana Y. Neuroprotection by adenosine A2A receptor blockade in experimental models of Parkinson's disease. J Neurochem. 2002;80:262–270.
61. Martinez-Mir M I, Probst A, Palacios J M. Adenosine A2 receptors: selective localization in the human basal ganglia and alterations with disease. Neuroscience. 1991;42:697–706.
62. Ross G W, Abbott R D, Petrovitch H, Morens D M, Grandinetti A, Tung K H, Tanner C M, Masaki K H, Blanchette P L, Curb J D, Popper J S, White L R. Association of coffee and caffeine intake with the risk of Parkinson disease. JAMA. 2000;283:2674–2679.
63. Ascherio A, Zhang S M, Heman M A, Kawachi I, Colditz G A, Speizer F E, Willett W C. Prospective study of caffeine consumption and risk of Parkinson's disease in men and women. Ann Neurol. 2001;50:56–63.
64. Hauser R A, Hubble J P, Truong D D. Randomized trial of the adenosine A(2A) receptor antagonist istradefylline in advanced PD. Neurology. 2003;61:297–303.
65. Bara-Jimenez W, Sherzai A, Dimitrova T, Favit A, Bibbiani F, Gillespie M, Morris M J, Mouradian M M, Chase T N. Adenosine A(2A) receptor antagonist treatment of Parkinson's disease. Neurology. 2003;61:293–296.
66. Bara-Jimenez W, Sherzai A, Dimitrova T, Favit A, Bibbiani F, Gillespie M, Morris M J, Mouradian M M, Chase T N. Adenosine A(2A) receptor antagonist treatment of Parkinson's disease. Neurology. 2003;61:293–296.
67. Zocchi C, Ongini E, Ferrara S, Baraldi P G, Dionisotti S. Binding of the radioligand [3H]-SCH 58261, a new 68. Keddie J R, Poucher S M, Shaw G R, Brooks R, Collis M G. In vivo characterisation of ZM 241385, a selective adenosine A2A receptor antagonist. Eur J Pharmacol. 1996;301:107–113.
69. Mori A, Shindou T, Ichimura M, Nonaka H, Kase H. The role of adenosine A2a receptors in regulating GABAergic synaptic transmission in striatal medium spiny neurons. J Neurosci. 1996;16:605–611.
70. Todde S, Moresco R M, Simonelli P, Baraldi P G, Cacciari B, Spalluto G, Varani K, Monopoli A, Matarrese M, Carpinelli A, Magni F, Kienle M G, Fazio F. Design, radiosynthesis, and biodistribution of a new potent and selective ligand for in vivo imaging of the adenosine A(2A) receptor system using positron emission tomography. J Med Chem. 2000;43:4359–4362.
71. Colotta V, Catarzi D, Varano F, Cecchi L, Filacchioni G, Martini C, Trincavelli L, Lucacchini A. 4-Amino-6-benzylamino-1,2-dihydro-2-phenyl-1,2,4-triazolo[4,3-alpha]-quinoxalin-1-one: a new A2A adenosine receptor antagonist with high selectivity versus A1 receptors. Arch Pharm (Weinheim). 1999;332:39–41.
72. Thompson R D, Secunda S, Daly J W, Olsson R A. N6,9-disubstituted adenines: potent, selective antagonists at the A1 adenosine receptor. J Med Chem. 1991;34:2877–2882.
73. Iwasaki K, Kusachi S, Tominaga Y, Kita T, Taniguchi G. Coronary artery spasm demonstrated by coronary angiography in a patient with acute myocarditis resembling acute myocardial infarction; a case report. Jpn J Med. 1991;30:573–577.
74. Chen J F, Steyn S, Staal R, Petzer J P, Xu K, Van Der Schyf C J, Castagnoli K, Sonsalla P K, Castagnoli N, Jr., Schwarzschild M A. 8-(3-Chlorostyryl)caffeine may attenuate MPTP neurotoxicity through dual actions of monoamine oxidase inhibition and A2A receptor antagonism. J Biol Chem. 2002;277:36040–36044.

The entire disclosure of all documents cited throughout this application are incorporated herein by reference.

The invention claimed is:

1. A compound of the formula I:

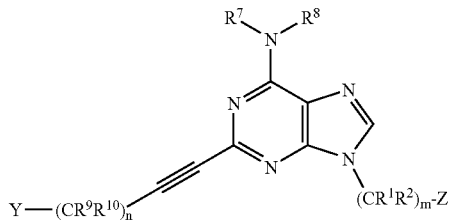

I wherein:

$R^1$ and $R^2$ are each independently selected from the group consisting of hydrogen, halogen, —$NH_2$, —OH, —SH, —$NHCH_3$, —$N(CH_3)_2$, —$OCH_3$, —$SCH_3$, ($C_1$–$C_8$) alkyl, aryl and aryl($C_1$–$C_8$)alkyl, wherein $R^1$ and $R^2$ are optionally substituted with 1 to 4 substituents of $R^a$, wherein the alkyl is optionally interrupted by 1–4 heteroatoms selected from —O—, —S—, —SO—, —$S(O)_2$— or amino (—$NR^a$—), or where $R^1$ and $R^2$ are independently absent, with the proviso that $R^a$ is not SH or halogen when the $R^1$ or $R^2$ to which $R^a$ is bound is halogen, —$NH_2$, —OH, —SH, —$NHCH_3$, —$N(CH_3)_2$, —$OCH_3$ or —$SCH_3$;

$R^3$ is selected from the group consisting of hydrogen, halo, —$OR^a$, $SR^a$, ($C_1$–$C_8$)alkyl, cyano, nitro, trifluoromethyl, trifluoromethoxy, ($C_3$–$C_8$)cycloalkyl, heterocycle, hetrocycle($C_1$–$C_8$)alkyl, aryl, aryl($C_1$–$C_8$)alkyl, heteroaryl, heteroaryl($C_1$–$C_8$)alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$—, —$SSR^a$, $R^aS(=O)$—, and $R^aS(=O)_2$—; or if the ring formed from the group $CR^3R^4R^5$ is aryl or heteroaryl or partially unsaturated, then $R^3$ can be absent;

$R^4$ and $R^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —$S(O)_2$— or amine (—$NR^a$—) in the ring, wherein any ring comprising $R^4$ and $R^5$ is optionally further substituted with from 1 to 14 $R^6$ groups; wherein each $R^6$ is independently selected from the group consisting of halo, —$OR^a$, —$SR^a$, substituted or unsubstituted ($C_1$–$C_8$)alkyl, cyano, nitro, trifluoromethyl, trifluoromethoxy, ($C_3$–$C_8$)cycloalkyl, ($C_6$–$C_{12}$) bicycloalkyl, heterocycle, hetrocyclyl($C_1$–$C_8$)alkyl, aryl, aryl($C_1$–$C_8$)alkyl, heteroaryl, heteroaryl($C_1$–$C_8$) alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$—, —$SSR^a$, and $R^aS(=O)$— or two $R^6$ groups and the atom to which they are attached combined to form C=O or C=S, or wherein two $R^6$ groups together with the atom or atoms to which they are attached can form a carbocyclic or heterocyclic ring;

$R^7$ and $R^8$ are each independently hydrogen, ($C_1$–$C_8$) alkyl, ($C_3$–$C_8$)cycloalkyl, aryl aryl($C_1$–$C_8$)alkylene, heteroaryl, heteroaryl($C_1$–$C_8$)alkylene; or wherein $R^7$ and $R^8$ together with the nitrogen atom to which they attach form a heterocycle or heteroaromatic ring;

$R^9$ and $R^{10}$ are each independently selected from the group consisting of hydrogen, halogen, —$NH_2$, —OH, —SH, —$NHCH_3$, —$N(CH_3)_2$, —$OCH_3$, —$SCH_3$, ($C_1$–$C_8$)alkyl, aryl and aryl($C_1$–$C_8$)alkyl, wherein $R^9$ and $R^{10}$ are optionally substituted with 1 to 4 substituents of $R^a$, wherein the alkyl is optionally interrupted by 1 to 4 heteroatoms selected from —O—, —S—, —SO—, —$S(O)_2$— or amino (—$NR^a$—), or where $R^9$ and $R^{10}$ are independently absent, with the proviso that $R^a$ is not SH or halogen in the case where the $R^9$ or $R^{10}$ to which $R^a$ is bound is halogen, —$NH_2$, —OH, —SH, —$NHCH_3$, —$N(CH_3)_2$, —$OCH_3$ or —$SCH_3$;

Y is —$CR^3R^4R^5$ or $NR^4R^5$;

Z is selected from the group consisting of halogen, vinyl, allyl, 1-propenyl, isopropenyl, ethynyl, 1-propynyl, 2-propynyl, 1,3-bytadienyl, penta-1,3-dienyl, penta-1,4-dienyl, hexa-1,3-dienyl, hexa-1,3,5-trienyl, ($C_3$–$C_8$) cycloalkyl, ($C_6$–$C_{12}$)bicycloalkyl, ($C_6$–$C_{20}$)polycyclyl, heterocyclyl, cycloalkyl($C_1$–$C_8$)alkyl, bicycloalkyl ($C_6$–$C_{12}$)alkyl, heterocyclyl($C_1$–$C_8$)alkyl, aryl, aryl ($C_1$–$C_8$)alkyl, heteroaryl, heteroaryl($C_1$–$C_8$)alkyl, —$NR^aR^b$, —$SR^a$, cyano, nitro, trifluoromethyl, trifluoromethoxy, —$CO_2R^a$, $R^aC(=O)O$—, $R^aC(=O)$—, —OCO$_2$R$^a$, R$^a$R$^b$NC(=O)O—, R$^b$OC(=O)NR$^a$—, R$^a$R$^b$NC(=O)—, R$^a$C(=O)NR$^b$—, R$^a$R$^b$NC(=O)NR$^b$—, R$^a$R$^b$NC(=S)NR$^b$—, R$^a$OC(=S)—, R$^a$C(=S)—, —SSR$^a$, R$^a$S(=O)—, —OS(O$_2$)R$^a$, —OS(=O)OR$^a$, —OS(O$_2$)OR$^a$ and —O(SO$_2$)NR$^a$R$^b$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, (C$_1$–C$_8$)alkyl, aryl, aryl(C$_1$–C$_8$)alkyl, (C$_3$–C$_8$)cycloalkyl, (C$_6$–C$_{12}$)bicycloalkyl, cycloalkyl (C$_1$–C$_8$)alkyl, bicycloalkyl(C$_6$–C$_{12}$)alkyl, heteroaryl and heteroaryl(C$_1$–C$_8$)alkyl, wherein the alkyl and cycloalkyl are optionally interrupted with 1–4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and (C$_1$–C$_8$)alkyl; and m is 0 to 8; n is 0, 1, 2 or 3, provided that when m is 0, Z is not halogen, cyano, or nitro or is not attached via a heteroatom, and when n is 0, Y is not —NR$^4$R$^5$; or a pharmaceutically acceptable salt thereof, optionally in the form of a single stereoisomer or mixture of stereoisomers thereof.

2. A compound of the formula II:

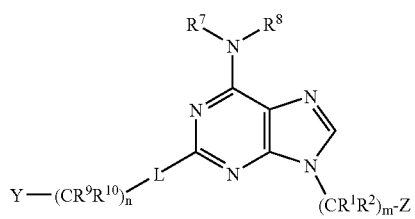

II wherein:

R$^1$ and R$^2$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$) alkyl, aryl and aryl(C$_1$–C$_8$)alkyl, wherein R$^1$ and R$^2$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^1$ and R$^2$ are independently absent, with the proviso that R$^a$ is not thio or halogen when the R$^1$ or R$^2$ to which R$^a$ is bound is halogen, —NH$_2$, —OH, —SH, —NHCH$_3$, —N(CH$_3$)$_2$, —OCH$_3$ or —SCH$_3$;

R$^3$ is selected from the group consisting of hydrogen, halo, —OR$^a$, —SR$^a$, (C$_1$–C$_8$)alkyl, cyano, nitro, trifluoromethyl, trifluoromethoxy, (C$_3$–C$_8$)cycloalkyl, heterocycle, hetrocycle(C$_1$–C$_8$)alkyl, aryl, aryl(C$_1$–C$_8$) alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC (=O)O—, R$^b$OC(=O)N(R$^a$)—, R$^a$R$^b$N—, R$^a$R$^b$NC (=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, R$^a$S(=O)$_2$—, or if the ring formed from the group CR$^3$R$^4$R$^5$ is aryl or heteroaryl or partially unsaturated, then R$^3$ can be absent;

R$^4$ and R$^5$ together with the atoms to which they are attached form a saturated or partially unsaturated, mono-, bi- or tricyclic, or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —S(O)$_2$— or amine (—NR$^c$—) in the ring, wherein any ring comprising R$^4$ and R$^5$ is optionally further substituted with from 1 to 14 R$^6$ groups; wherein each R$^6$ is independently selected from the group consisting of hydrogen, halo, —OR$^a$, —SR$^a$, substituted or unsubstituted (C$_1$–C$_8$)alkyl, cyano, nitro, trifluoromethyl, trifluoromethoxy, (C$_3$–C$_8$)cycloalkyl, (C$_6$–C$_{12}$)bicycloalkyl, heterocycle, hetrocyclyl(C$_1$–C$_8$) alkyl, aryl, aryl(C$_1$–C$_8$)alkyl, heteroaryl, heteroaryl (C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, or two R$^6$ groups and the atom to which they are attached combined to form C=O or C=S, or wherein two R$^6$ groups together with the atom or atoms to which they are attached can form a carbocyclic or heterocyclic ring;

R$^7$ and R$^8$ are each independently hydrogen, (C$_1$–C$_8$) alkyl, (C$_3$–C$_8$)cycloalkyl, aryl or aryl(C$_1$–C$_8$)alkylene, heteroaryl, heteroaryl(C$_1$–C$_8$)alkylene-; or wherein R$^7$ and R$^8$ together with the nitrogen atom to which they attach form a heterocycle or heteroaromatic ring;

R$^9$ and R$^{10}$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$)alkyl, aryl and aryl(C$_1$–C$_8$)alkyl, wherein R$^9$ and R$^{10}$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^9$ and R$^{10}$ are independently absent, with the proviso that R$^a$ is not SH or halogen in the case where R$^9$ and R$^{10}$ to which R$^a$ is bound is halogen, —NH$_2$, —OH, —SH, —NHCH$_3$, —N(CH$_3$)$_2$, —OCH$_3$ and —SCH$_3$;

L is a linker selected from the group consisting of —(C$_1$–C$_3$)alkyl-C≡C—, —C≡C—(C$_1$–C$_3$)alkyl-, —(CH$_2$)$_{1-3}$—CH=CH—, —CH=CH—(CH$_2$)$_{1-3}$—, —(CH$_2$)$_{1-2}$—CH=CH—CH$_2$— and —CH$_2$—CH=CH—(CH$_2$)$_{1-2}$—;

Y is —CR$^3$R$^4$R$^5$ or NR$^4$R$^5$;

Z is selected from the group consisting of halogen, vinyl, allyl, 1-propenyl, isopropenyl, ethynyl, 1-propynyl, 2-propynyl, 1,3-bytadienyl, penta-1,3-dienyl, penta-1,4-dienyl, hexa-1,3-dienyl, hexa-1,3,5-trienyl, (C$_3$–C$_8$) cycloalkyl, (C$_6$–C$_{12}$)bicycloalkyl, (C$_6$–C$_{20}$)polycyclyl, heterocyclyl, cycloalkyl(C$_1$–C$_8$)alkyl, bicycloalkyl (C$_6$–C$_{12}$)alkyl, heterocyclyl(C$_1$–C$_8$)alkyl, aryl, aryl (C$_1$–C$_8$)alkyl, heteroaryl, heteroaryl(C$_1$–C$_8$)alkyl, —NR$^a$R$^b$, —SR$^a$, cyano, nitro, trifluoromethyl, trifluoromethoxy, —CO$_2$R$^a$, R$^a$C(=O)O—, R$^a$C(=O)—, —OCO$_2$R$^a$, R$^a$R$^b$NC(=O)O—, R$^b$OC(=O)NR$^a$—, R$^a$R$^b$NC(=O)—, R$^a$C(=O)NR$^b$—, R$^a$R$^b$NC(=O) NR$^b$—, R$^a$R$^b$NC(=S)NR$^b$—, R$^a$OC(=S)—, R$^a$C(=S)—, —SSR$^a$, R$^a$S(=O)—, —OS(O$_2$)R$^a$, —OS(=O)OR$^a$, —OS(O$_2$)OR$^a$ and —O(SO$_2$)NR$^a$R$^b$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, (C$_1$–C$_8$)alkyl, aryl, aryl(C$_1$–C$_8$)alkyl, (C$_3$–C$_8$)cycloalkyl, (C$_6$–C$_{12}$)bicycloalkyl, cycloalkyl (C$_1$–C$_8$)alkyl, bicycloalkyl(C$_6$–C$_{12}$)alkyl, heteroaryl and heteroaryl(C$_1$–C$_8$)alkyl, wherein the alkyl and cycloalkyl are optionally interrupted with 1 to 4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and (C$_1$–C$_8$)alkyl; and m is 0 to 8; n is 0, 1, 2 or 3 provided that when m is 0, Z is not halogen, cyano, nitro or is not attached via or a heteroatom; or a pharmaceutically acceptable salt thereof, optionally in the form of a single stereoisomer or mixture of stereoisomers thereof.

3. The compound of claim 1, wherein (CR$^1$R$^2$)$_m$ together is selected from the group consisting of methylene, ethylene, propylene, butylene, pentylene, hexylene, heptylene, octylene, iso-propylene, iso-butylene, sec-butylene and tert-butylene.

4. The compound of claim 1, wherein (CR$^1$R$^2$)$_m$ together is selected from the group consisting of methylene, ethylene, propylene and iso-propylene.

5. A compound of the formula I:

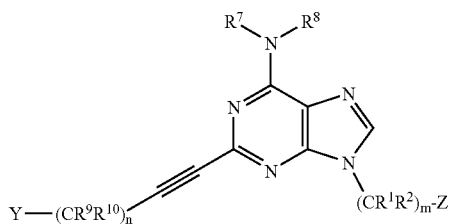

I wherein:
(CR$^1$R$^2$)$_m$-Z together is selected from the group consisting of —CH$_2$CH=CH$_2$, —CH$_2$C≡CH, —CH$_2$C≡CCH$_3$ or —CH$_2$CH$_2$C≡CH;

Y is —CR$^3$R$^4$R$^5$ or NR$^4$R$^5$;

R$^3$ is selected from the group consisting of hydrogen, halo, —OR$^a$, SR$^a$, (C$_1$–C$_8$)alkyl, cyano, nitro, trifluoromethyl, trifluoromethoxy, (C$_3$–C$_8$)cycloalkyl, heterocycle, hetrocycle(C$_1$–C$_8$)alkyl, aryl, aryl(C$_1$–C$_8$)alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC (=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, R$^a$S(=O)$_2$—; or if the ring formed from the group CR$^3$R$^4$R$^5$ is aryl or heteroaryl or partially unsaturated, then R$^3$ can be absent;

R$^4$ and R$^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —S(O)$_2$— or amine (—NR$^a$—) in the ring, wherein any ring comprising R$^4$ and R$^5$ is optionally further substituted with from 1 to 14 R$^6$ groups; wherein each R$^6$ is independently selected from the group consisting of halo, —OR$^a$, —SR$^a$, substituted or unsubstituted (C$_1$–C$_8$)alkyl, cyano, nitro, trifluoromethyl, trifluoromethoxy, (C$_3$–C$_8$)cycloalkyl, (C$_6$–C$_{12}$) bicycloalkyl, heterocycle, hetrocyclyl(C$_1$–C$_8$)alkyl, aryl, aryl(C$_1$–C$_8$)alkyl, heteroaryl, heteroaryl(C$_1$–C$_8$) alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC (=S)—, R$^a$C(=S)—, —SSR$^a$, R$^a$S(=O)— or two R$^6$ groups and the atom to which they are attached combined to form C=O or C=S, or wherein two R$^6$ groups together with the atom or atoms to which they are attached can form a carbocyclic or heterocyclic ring;

R$^7$ and R$^8$ are each independently hydrogen, (C$_1$–C$_8$) alkyl, (C$_3$–C$_8$)cycloalkyl, aryl or aryl(C$_1$–C$_8$)alkylene, heteroaryl, heteroaryl(C$_1$–C$_8$)alkylene-; or wherein R$^7$ and R$^8$ together with the nitrogen atom to which they attach form a heterocycle or heteroaromatic ring;

R$^9$ and R$^{10}$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$)alkyl, aryl and aryl(C$_1$–C$_8$)alkyl, wherein R$^9$ and R$^{10}$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^9$ and R$^{10}$ are independently absent, with the proviso that R$^a$ is not SH or halogen in the case where the R$^9$ or R$^{10}$ to which R$^a$ is bound is halogen, —NH$_2$, —OH, —SH, —NHCH$_3$, —N(CH$_3$)$_2$, —OCH$_3$ or —SCH$_3$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, (C$_1$–C$_8$)alkyl, aryl, aryl(C$_1$–C$_8$)alkyl, (C$_3$–C$_8$)cycloalkyl, (C$_6$–C$_{12}$)bicycloalkyl, cycloalkyl (C$_1$–C$_8$)alkyl, bicycloalkyl(C$_6$–C$_{12}$)alkyl, heteroaryl and heteroaryl(C$_1$–C$_8$)alkyl, wherein the alkyl and cycloalkyl are optionally interrupted with 1–4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and (C$_1$–C$_8$)alkyl; and n is 0, 1, 2 or 3; or a pharmaceutically acceptable salt thereof, optionally in the form of a single stereoisomer or mixture of stereoisomers thereof.

6. The compound of claim 1, wherein (CR$^1$R$^2$)$_m$-Z together is —CH$_2$C≡CH.

7. The compound of claim 1, wherein R$_1$ and R$_2$ are hydrogen or are absent, m is 2 to 8 and the group (CR$^1$R$^2$)$_m$ optionally comprises 1 to 4 alkenyl or alkynyl conjugated or unconjugated groups.

8. The compound of claim 1, wherein m is 1 to 8 and Z is selected from the group consisting of —NH$_2$, —SH, —NR$^b$R$^b$, —SR$^a$ and cyano.

9. The compound of claim 1, wherein Z is an aryl, (C$_3$–C$_8$)cycloalkyl, (C$_6$–C$_{12}$)bicycloalkyl, or (C$_6$–C$_{20}$)polycyclyl, wherein the ring atoms are optionally interrupted by 1 to 8 heteroatoms selected from the group consisting of —O—, —S—, —SO—, —S(O)$_2$— and amino (—NR$^a$—).

10. A compound of the formula I:

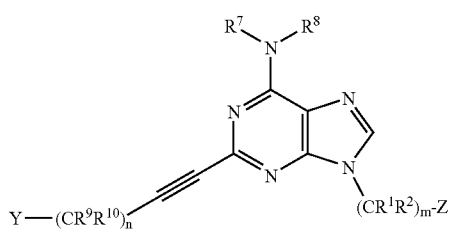

I wherein:
Z is selected from the group consisting of cyclopropyl, cyclobutyl, cyclopentyl, cyclohexyl, cycloheptyl and cyclooctyl ring optionally substituted with 1 to 4 substituents of R$^a$;

Y is —CR$^3$R$^4$R$^5$ or NR$^4$R$^5$;

R$^1$ and R$^2$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$) alkyl, aryl and aryl(C$_1$–C$_8$)alkyl, wherein R$^1$ and R$^2$ are optionally substituted with 1 to 4 substituents of R$^a$, wherein the alkyl is optionally interrupted by 1–4 heteroatoms selected from —O—, —S—, —SO—, —S(O)$_2$— or amino (—NR$^a$—), or where R$^1$ and R$^2$ are independently absent, with the proviso that R$^a$ is not SH or halogen when the R$^1$ or R$^2$ to which R$^a$ is bound is halogen, —NH$_2$, —OH, —SH, —NHCH$_3$, —N(CH$_3$)$_2$, —OCH$_3$ or —SCH$_3$;

R$^3$ is selected from the group consisting of hydrogen, halo, —OR$^a$, SR$^a$, (C$_1$–C$_8$)alkyl, cyano, nitro, trifluoromethyl, trifluoromethoxy, (C$_3$–C$_8$)cycloalkyl, heterocycle, hetrocycle(C$_1$–C$_8$)alkyl, aryl, aryl(C$_1$–C$_8$)alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, R$^a$S(=O)$_2$—; or if the ring formed from the group CR$^3$R$^4$R$^5$ is aryl or heteroaryl or partially unsaturated, then R$^3$ can be absent;

R$^4$ and R$^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —S(O)$_2$— or amine (—NR$^a$—) in the ring, wherein any ring comprising R$^4$ and R$^5$ is optionally further substituted with from 1 to 14 R$^6$ groups; wherein each R$^6$ is independently selected from the group consisting of halo, —OR$^a$, —SR$^a$, substituted or unsubstituted (C$_1$–C$_8$)alkyl, cyano, nitro, trifluoromethyl, trifluoromethoxy, (C$_3$–C$_8$)cycloalkyl, (C$_6$–C$_{12}$) bicycloalkyl, heterocycle, hetrocyclyl(C$_1$–C$_8$)alkyl, aryl, aryl(C$_1$–C$_8$)alkyl, heteroaryl, heteroaryl(C$_1$–C$_8$) alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC (=S)—, R$^a$C(=S)—, —SSR$^a$, R$^a$S(=O)— or two R$^6$ groups and the atom to which they are attached combined to form C=O or C=S, or wherein two R$^6$ groups together with the atom or atoms to which they are attached can form a carbocyclic or heterocyclic ring;

R$^7$ and R$^8$ are each independently hydrogen, (C$_1$–C$_8$) alkyl, (C$_3$–C$_8$)cycloalkyl, aryl or aryl(C$_1$–C$_8$)alkylene, heteroaryl, heteroaryl(C$_1$–C$_8$)alkylene; or wherein R$^7$ and R$^8$ together with the nitrogen atom to which they attach form a heterocycle or heteroaromatic ring;

R$^9$ and R$^{10}$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$)alkyl, aryl and aryl(C$_1$–C$_8$)alkyl, wherein R$^9$ and R$^{10}$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^9$ and R$^{10}$ are independently absent, with the proviso that R$^a$ is not SH or halogen in the case where the R$^9$ or R$^{10}$ to which R$^a$ is bound is halogen, —NH$_2$, —OH, —SH, —NHCH$_3$, —N(CH$_3$)$_2$, —OCH$_3$ or —SCH$_3$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, (C$_1$–C$_8$)alkyl, aryl, aryl(C$_1$–C$_8$)alkyl, (C$_3$–C$_8$)cycloalkyl, (C$_6$–C$_{12}$)bicycloalkyl, cycloalkyl (C$_1$–C$_8$)alkyl, bicycloalkyl(C$_6$–C$_{12}$)alkyl, heteroaryl and heteroaryl(C$_1$–C$_8$)alkyl, wherein the alkyl and cycloalkyl are optionally interrupted with 1–4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and (C$_1$–C$_8$)alkyl; and m is 0 to 8; n is 0, 1, 2 or 3, provided that when n is 0, Y is not —NR$^4$R$^5$; or a pharmaceutically acceptable salt thereof, optionally in the form of a single stereoisomer or mixture of stereoisomers thereof.

11. The compound of claim 10, wherein Z is selected from the group consisting of cyclopropyl, cyclobutyl, cyclopentyl and cyclohexyl, where m is 0 or 1.

12. The compound of claim 10, wherein Z is cyclopentyl and where m is 0.

13. The compound of claim 10, wherein Z is cyclobutyl, m is 1 and R$^1$ and R$^2$ are hydrogen.

14. A compound of formula I:

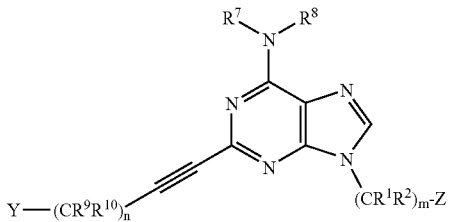

wherein Y is selected from the group consisting of

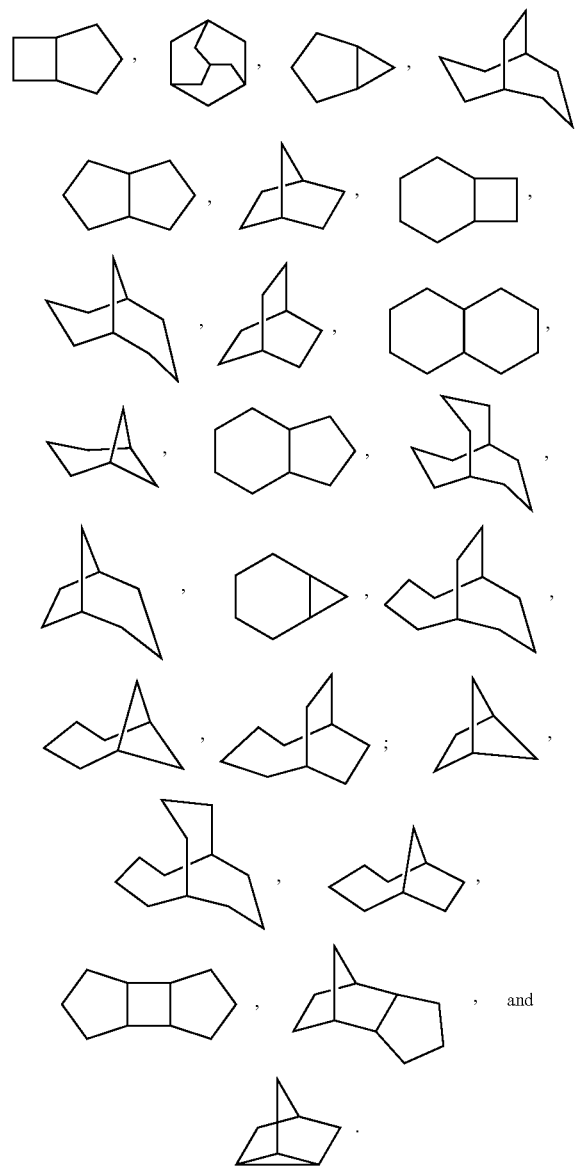

wherein Y optionally comprises 1, 2 or 3 double bonds; each carbon in the ring is optionally replaced by or interrupted by 1 to 6 heteroatoms selected from —O—, —S—, —SO—, —S(O)$_2$—, or amino (—NR$^a$—), and is optionally further substituted with from 1 to 10 R$^6$ groups, provided that the Y or Z ring is not attached at a bridgehead carbon atom or at a trisubstituted carbon atom;

Z is selected from the group consisting of halogen, vinyl, allyl, 1-propenyl, isopropenyl, ethynyl, 1-propynyl, 2-propynyl, 1,3-bytadienyl, penta-1,3-dienyl, penta-1,4-dienyl, hexa-1,3-dienyl, hexa-1,3,5-trienyl, (C$_3$–C$_8$)cycloalkyl, (C$_6$–C$_{12}$)bicycloalkyl, (C$_6$–C$_{20}$)polycyclyl, heterocyclyl, cycloalkyl(C$_1$–C$_8$)alkyl, bicycloalkyl (C$_6$–C$_{12}$)alkyl, heterocyclyl(C$_1$–C$_8$)alkyl, aryl, aryl(C$_1$–C$_8$)alkyl, heteroaryl, heteroaryl(C$_1$–C$_8$)alkyl, —NR$^a$R$^b$, —SR$^a$, cyano, nitro, trifluoromethyl, trifluoromethoxy, —CO$_2$R$^a$, R$^a$C(=O)O—, R$^a$C(=O)—, —OCO$_2$R$^a$, R$^a$R$^b$NC(=O)O—, R$^b$OC(=O)NR$^a$—, R$^a$R$^b$NC(=O)—, R$^a$C(=O)NR$^b$—, R$^a$R$^b$NC(=O)NR$^b$—, R$^a$R$^b$NC(=S)NR$^b$—, R$^a$OC(=S)—, R$^a$C(=S)—, —SSR$^a$, R$^a$S(=O)—, —OS(O$_2$)R$^a$, —OS(=O)OR$^a$, —OS(O$_2$)OR$^a$ and —O(SO$_2$)NR$^a$R$^b$;

R$^1$ and R$^2$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$)alkyl, aryl and aryl(C$_1$–C$_8$)alkyl, wherein R$^1$ and R$^2$ are optionally substituted with 1 to 4 substituents of R$^a$, wherein the alkyl is optionally interrupted by 1–4 heteroatoms selected from —O—, —S—, —SO—, —S(O)$_2$— or amino (—NR$^a$—), or where R$^1$ and R$^2$ are independently absent, with the proviso that R$^a$ is not SH or halogen when the R$^1$ or R$^2$ to which R$^a$ is bound is halogen, —NH$_2$, —OH, —SH, —NHCH$_3$, —N(CH$_3$)$_2$, —OCH$_3$ or —SCH$_3$;

R$^6$ is independently selected from the group consisting of halo, —OR$^a$, —SR$^a$, substituted or unsubstituted (C$_1$–C$_8$)alkyl, cyano, nitro, trifluoromethyl, trifluoromethoxy, (C$_3$–C$_8$)cycloalkyl, (C$_6$–C$_{12}$)bicycloalkyl, heterocycle, hetrocyclyl(C$_1$–C$_8$)alkyl, aryl, aryl(C$_1$–C$_8$)alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)— or two R$^6$ groups and the atom to which they are attached combined to form C=O or C=S, or wherein two R$^6$ groups together with the atom or atoms to which they are attached can form a carbocyclic or heterocyclic ring;

R$^7$ and R$^8$ are each independently hydrogen, (C$_1$–C$_8$)alkyl, (C$_3$–C$_8$)cycloalkyl, aryl or aryl(C$_1$–C$_8$)alkylene, heteroaryl, heteroaryl(C$_1$–C$_8$)alkylene-; or wherein R$^7$ and R$^8$ together with the nitrogen atom to which they attach form a heterocycle or heteroaromatic ring;

R$^9$ and R$^{10}$ are each independently selected from the group consisting of hydrogen, halogen, —NH$_2$, —OH, —SH, —NHCH$_3$, —N(CH$_3$)$_2$, —OCH$_3$, —SCH$_3$, (C$_1$–C$_8$)alkyl, aryl and aryl(C$_1$–C$_8$)alkyl, wherein R$^9$ and R$^{10}$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^9$ and R$^{10}$ are independently absent, with the proviso that R$^a$ is not SH or halogen in the case where the R$^9$ or R$^{10}$ to which R$^a$ is bound is halogen, —NH$_2$, —OH, —SH, —NHCH$_3$, —N(CH$_3$)$_2$, —OCH$_3$ or —SCH$_3$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, (C$_1$–C$_8$)alkyl, aryl, aryl(C$_1$–C$_8$)alkyl, ($C_3$–$C_8$)cycloalkyl, ($C_6$–$C_{12}$)bicycloalkyl, cycloalkyl($C_1$–$C_8$)alkyl, bicycloalkyl($C_6$–$C_{12}$)alkyl, heteroaryl and heteroaryl($C_1$–$C_8$)alkyl, wherein the alkyl and cycloalkyl are optionally interrupted with 1–4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and ($C_1$–$C_8$)alkyl; and m is 0 to 8; n is 0, 1, 2 or 3, provided that when m is 0, Z is not halogen, cyano, or nitro or attached via a heteroatom; or a pharmaceutically acceptable salt thereof, optionally in the form of a single stereoisomer or mixture of stereoisomers thereof.

15. A compound of formula I:

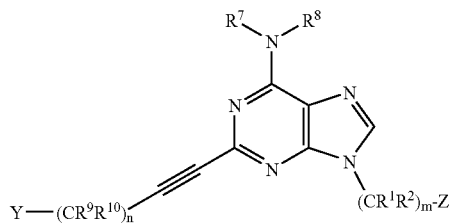

I wherein R$^1$ and R$^2$ are hydrogen, m is 0, 1, 2 or 3 and Z is the moiety derived from the ring selected from the group consisting of furan, dihydro-furan, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with from 1 to 10 R$^a$ groups;

Y is —CR$^4$R$^5$ or NR$^4$R$^5$;

R$^3$ is selected from the group consisting of hydrogen, halo, —OR$^a$, SR$^a$, ($C_1$–$C_8$)alkyl, cyano, nitro, trifluoromethyl, trifluoromethoxy, ($C_3$–$C_8$)cycloalkyl, heterocycle, hetrocycle($C_1$–$C_8$)alkyl, aryl, aryl($C_1$–$C_8$)alkyl, heteroaryl, heteroaryl($C_1$–$C_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, R$^a$S(=O)$_2$—; or if the ring formed from the group CR$^3$R$^4$R$^5$ is aryl or heteroaryl or partially unsaturated, then R$^3$ can be absent;

R$^4$ and R$^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —S(O)$_2$— or amine (—NR$^a$—) in the ring, wherein any ring comprising R$^4$ and R$^5$ is optionally further substituted with from 1 to 14 R$^6$ groups; wherein each R$^6$ is independently selected from the group consisting of halo, —OR$^a$, —SR$^a$, substituted or unsubstituted ($C_1$–$C_8$)alkyl, cyano, nitro, trifluoromethyl, trifluoromethoxy, ($C_3$–$C_8$)cycloalkyl, ($C_6$–$C_{12}$)bicycloalkyl, heterocycle, hetrocyclyl($C_1$–$C_8$)alkyl, aryl, aryl($C_1$–$C_8$)alkyl, heteroaryl, heteroaryl($C_1$–$C_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)— or two R$^6$ groups and the atom to which they are attached combined to form C=O or C=S, or wherein two R$^6$ groups together with the atom or atoms to which they are attached can form a carbocyclic or heterocyclic ring;

R$^7$ and R$^8$ are each independently hydrogen, ($C_1$–$C_8$) alkyl, ($C_3$–$C_8$)cycloalkyl, aryl or aryl($C_1$–$C_8$)alkylene, heteroaryl, heteroaryl($C_1$–$C_8$)alkylene; or wherein R$^7$ and R$^8$ together with the nitrogen atom to which they attach form a heterocycle or heteroaromatic ring;

R$^9$ and R$^{10}$ are each independently selected from the group consisting of hydrogen, halogen, —NH$_2$, —OH, —SH, —NHCH$_3$, —N(CH$_3$)$_2$, —OCH$_3$, —SCH$_3$, ($C_1$–$C_8$)alkyl, aryl and aryl($C_1$–$C_8$)alkyl, wherein R$^9$ and R$^{10}$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^9$ and R$^{10}$ are independently absent, with the proviso that R$^a$ is not SH or halogen in the case where the R$^9$ or R$^{10}$ to which R$^a$ is bound is halogen, —NH$_2$, —OH, —SH, —NHCH$_3$, —N(CH$_3$)$_2$, —OCH$_3$ or —SCH$_3$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, ($C_1$–$C_8$)alkyl, aryl, aryl($C_1$–$C_8$)alkyl, ($C_3$–$C_8$)cycloalkyl, ($C_6$–$C_{12}$)bicycloalkyl, cycloalkyl($C_1$–$C_8$)alkyl, bicycloalkyl($C_6$–$C_{12}$)alkyl, heteroaryl and heteroaryl($C_1$–$C_8$)alkyl, wherein the alkyl and cycloalkyl are optionally interrupted with 1–4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and ($C_1$–$C_8$)alkyl; and m is 0 to 8; n is 0, 1, 2 or 3, provided that when n is 0, Z is not attached via a heteroatom, and when n is 0, Y is not —NR$^4$R$^5$; or a pharmaceutically acceptable salt thereof, optionally in the form of a single stereoisomer or mixture of stereoisomers thereof.

16. The compound of claim 15, wherein R$^1$ and R$^2$ are hydrogen, m is 0 or 1, and Z is the moiety derived from the ring selected from the group consisting of furan, thiophene, pyrrole, 2H-pyrrole, oxazole, thiazole, imidazole, pyrazole, isoxazole, isothiazole, 1,2,3-oxadiazole, 1,2,4-oxadiazole, 1,2,3-triazole, 1,2,4-triazole, 1,3,4-thiadiazole and 1H-tetrazole, wherein each Z group is optionally substituted with from 1 to 3 $R^a$ groups selected from the group consisting of methyl, ethyl, propyl, iso-propyl, —$NH_2$, —OH, —SH, —$NHCH_3$, —$N(CH_3)_2$, —$OCH_3$ and —$SCH_3$.

17. The compound of claim 1, wherein Z is selected from the group consisting of —$CO_2R^a$, $R^aC(=O)O$—, $R^aC(=O)$—, —$OCO_2R^a$, $R^aR^bNC(=O)O$—, $R^bOC(=O)NR^a$—, $R^aR^bN$—, $R^aR^bNC(=O)$—, $R^aC(=O)NR^b$—, $R^aR^bNC(=O)NR^b$—, $R^aR^bNC(=S)NR^b$—, $R^aOC(=S)$—, $R^aC(=S)$—, —$SSR^a$, $R^aS(=O)$—, $R^aS(O_2)$—, —$OS(=O)OR^a$, —$OS(O_2)OR^a$ and —$OS(O_2)NR^aR^b$, wherein m is 1 to 8.

18. The compound of claim 17, wherein Z is selected from the group consisting of —$CO_2R^a$, $R^aC(=O)O$—, $R^aC(=O)$—, —$OCO_2R^a$, $R^aR^bNC(=O)O$—, $R^bOC(=O)NR^a$—, $R^aR^bN$—, $R^aR^bNC(=O)$—, $R^aC(=O)NR^b$—, $R^aR^bNC(=O)NR^b$—, $R^aR^bNC(=S)NR^b$—, $R^aOC(=S)$—, $R^aC(=S)$—, —$SSR^a$, $R^aS(=O)$—, $R^aS(=O)_2$—, —$OS(O_2)R^a$, —$OS(=O)OR^a$, —$OS(O_2)OR^a$ and —$O(SO_2)NR^aR^b$, and wherein $(R^1R^2)_m$ together is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH=CHCH_2$—, —$CH_2CH=CH$—, —$CH=CHCH_2CH_2$—, —$CH_2CH=CHCH_2$—, —$CH_2CH_2CH=CH$—, —$C≡CCH_2$—, —$CH_2C≡C$—, —$C≡CCH_2CH_2$—, —$CH_2C≡CCH_2$— and —$CH_2CH_2C≡C$—.

19. The compound of claim 17, wherein Z is —$CO_2R^a$, $R^aC(=O)$—, $R^aR^bN$—, $R^aOC(=S)$—, $R^aC(=S)$—, $R^aS(=O)$—, $R^aS(=O)_2$—, —$OS(O_2)R^a$, —$OS(=O)OR^a$, —$OS(O_2)OR^a$, or —$OS(O_2)NR^aR^b$, and wherein $(CR^1R^2)_m$ together is selected from the group consisting of —$CH_2$—, —$CH_2CH_2$—, —$CH_2CH_2CH_2$—, —$CH_2CH_2CH_2CH_2$—, —$CH_2CH_2CH_2CH_2CH_2$—, —$CH_2CH_2CH_2CH_2CH_2CH_2$—, —$CH=CHCH_2$—, —$CH_2CH=CH$—, —$CH=CHCH_2CH_2$—, —$CH_2CH=CHCH_2$—, —$CH_2CH_2CH=CH$—, —$C≡CCH_2$—, —$CH_2C≡C$—, —$C≡CCH_2CH_2$—, —$CH_2C≡CCH_2$— and —$CH_2CH_2C≡C$—.

20. The compound of claim 1, wherein each $R^9$ is independently selected from the group consisting of hydrogen, halo, —$OR^a$, —$SR^a$, ($C_1$–$C_8$)alkyl, cyano, nitro, trifluoromethyl, trifluoromethoxy, ($C_3$–$C_8$)cycloalkyl, heterocyclyl, heterocyclyl($C_1$–$C_8$)alkylene-, aryl, aryl($C_1$–$C_8$)alkylene-, heteroaryl, heteroaryl($C_1$–$C_8$)alkylene-, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$—, —$SSR^a$, $R^aS(=O)$—, $R^aS(=O)_2$—.

21. The compound of claim 1, wherein $R^3$ is selected from the group consisting of hydrogen, halo, —$OR^a$, —$SR^a$, cyano, nitro, trifluoromethyl, trifluoromethoxy, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$, $SSR^a$, $R^aS(=O)$—, and $R^aS(=O)_2$—; or if the ring formed from the group $CR^3R^4R^5$ is aryl or heteroaryl or partially unsaturated then $R^3$ can be absent.

22. The compound of claim 1, wherein $R^3$ is selected from the group consisting of hydrogen, OH, $OCH_3$, OAc, $NH_2$, $NHCH_3$, $N(CH_3)_2$ and NHAc.

23. The compound of claim 22, wherein $R^3$ is hydrogen or OH.

24. The compound of claim 1, wherein $R^4$ and $R^5$ together with the atom to which they are attached form a saturated or partially unsaturated, mono-, bi- or tricyclic ring, or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —$S(O)_2$— or amine (—$NR^a$—) in the ring, wherein any ring comprising $R^4$ and $R^5$ is optionally further substituted with from 1 to 14 $R^6$ groups; wherein each $R^6$ is independently selected from the group consisting of halo, —$OR^a$, —$SR^a$, ($C_1$–$C_8$)alkyl, cyano, nitro, trifluoromethyl, trifluoromethoxy, ($C_1$–$C_8$)cycloalkyl, ($C_6$–$C_{12}$)bicycloalkyl, heterocycle, hetrocyclyl($C_1$–$C_8$)alkyl, aryl, aryl ($C_1$–$C_8$)alkyl, heteroaryl, heteroaryl($C_1$–$C_8$)alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$—, —$SSR^a$, $R^aS(=O)$—, or two $R^6$ groups and the atom to which they are attached combined to form C=O or C=S, or wherein two $R^6$ groups together with the atom or atoms to which they are attached can form a carbocyclic or heterocyclic ring.

25. The compound of claim 24, wherein the ring comprising $R^4$ and $R^5$ and the atom to which they are attached is selected from the group consisting of cyclopentane, cyclohexane, piperidine, dihydro-pyridine, tetrahydro-pyridine, pyridine, piperazine, decaline, tetrahydro-pyrazine, dihydro-pyrazine, pyrazine, dihydro-pyrimidine, tetrahydro-pyrimidine, hexahydro-pyrimidine, pyrazine, imidazole, dihydro-imidazole, imidazolidine, pyrazole, dihydro-pyrazole, pyrazolidine, norbornane and adamantane, each unsubstituted or substituted.

26. The compound of claim 25, wherein the ring comprising $R^4$ and $R^5$ and the atom to which they are attached is selected from the group consisting of cyclohexane, piperidine, piperazine, norbornane, adamantane, each unsubstituted or substituted.

27. The compound of claim 1, wherein each $R^6$ is independently selected from the group consisting of substituted or unsubstituted ($C_1$–$C_8$)alkyl, —$OR^a$, —$CO_2R^a$, $R^aC(=O)$—, $R^aC(=O)O$—, $R^aR^bN$—, $R^aR^bNC(=O)$— and aryl, provided that when the ring comprising $R^4$ and $R^5$ contains a ring heteroatom that is O or S, the ring heteroatom that is O or S is not substituted with $R^6$.

28. The compound of claim 1, wherein each $R^6$ is independently selected from the group consisting of OH, $OCH_3$, methyl, ethyl, t-butyl, —$CO_2R^a$, —$CONR^aR^b$, OAc, $NH_2$, $NHCH_3$, $N(CH_3)_2$, NHEt and $N(Et)_2$, provided that when the ring comprising $R^4$ and $R^5$ contains a ring heteroatom that is O or S, the ring heteroatom that is O or S is not substituted with $R^6$.

29. The compound of claim 28, wherein each $R^6$ is independently selected from the group consisting of methyl, ethyl, —$CO_2R^a$, —$CONR^aR^b$ and OAc, provided that when the ring comprising $R^4$ and $R^5$ contains a heteroatom, the heteroatom is not substituted with OAc.

30. The compound of claim 1, wherein number of $R^6$ groups substituted on the $R^4R^5$ ring is from 1 to 4.

31. A compound of formula I:

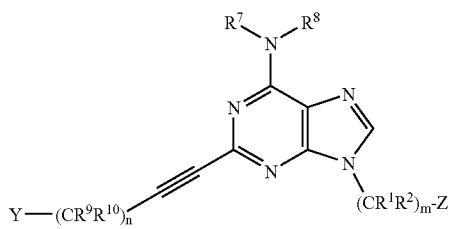

wherein $R^7$ and $R^8$ are each independently selected from the group consisting of hydrogen, $(C_1-C_8)$alkyl-, aryl$(C_1-C_8)$ alkylene-, mono- or bicyclic-, aromatic or nonaromatic ring having 3, 4, 5, 6, 7, 8, 9 or 10 ring atoms, wherein the ring atoms are optionally interrupted by 1, 2, 3 or 4 heteroatoms selected from the group consisting of —O—, —S—, —SO—, —S(O)$_2$— or amine (—NR$^a$—) in the ring, and each is optionally substituted with from 1, 2, 3 or 4 R$^a$ groups;

Y is —CR$^3$R$^4$R$^5$ or NR$^4$R$^5$;

Z is selected from the group consisting of halogen, vinyl, allyl, 1-propenyl, isopropenyl, ethynyl, 1-propynyl, 2-propynyl, 1,3-bytadienyl, penta-1,3-dienyl, penta-1,4-dienyl, hexa-1,3-dienyl, hexa-1,3,5-trienyl, $(C_3-C_8)$ cycloalkyl, $(C_6-C_{12})$bicycloalkyl, $(C_6-C_{20})$polycyclyl, heterocyclyl, cycloalkyl$(C_1-C_8)$alkyl, bicycloalkyl $(C_6-C_{12})$alkyl, heterocyclyl$(C_1-C_8)$alkyl, aryl, aryl $(C_1-C_8)$alkyl, heteroaryl, heteroaryl$(C_1-C_8)$alkyl, —NR$^a$R$^b$, —SR$^a$, cyano, nitro, trifluoromethyl, trifluoromethoxy, —CO$_2$R$^a$, R$^a$C(=O)O—, R$^a$C(=O)—, —OCO$_2$R$^a$, R$^a$R$^b$NC(=O)O—, R$^b$OC(=O)NR$^a$—, R$^a$R$^b$NC(=O)—, R$^a$C(=O)NR$^b$—, R$^a$R$^b$NC(=O) NR$^b$—, R$^a$R$^b$NC(=S)NR$^b$—, R$^a$OC(=S)—, R$^a$C (=S)—, —SSR$^a$, R$^a$S(=O)—, —OS(O)$_2$R$^a$, —OS (=O)OR$^a$, —OS(O$_2$)OR$^a$ and —O(SO$_2$)NR$^a$R$^b$;

R$^1$ and R$^2$ are each independently selected from the group consisting of hydrogen, halogen, —NH$_2$, —OH, —SH, —NHCH$_3$, —N(CH$_3$)$_2$, —OCH$_3$, —SCH$_3$, $(C_1-C_8)$ alkyl, aryl and aryl$(C_1-C_8)$alkyl, wherein R$^1$ and R$^2$ are optionally substituted with 1 to 4 substituents of R$^a$, wherein the alkyl is optionally interrupted by 1–4 heteroatoms selected from —O—, —S—, —SO—, —S(O)$_2$— or amino (—NR$^a$—), or where R$^1$ and R$^2$ are independently absent, with the proviso that R$^a$ is not SH or halogen when the R$^1$ or R$^2$ to which R$^a$ is bound is halogen, —NH$_2$, —OH, —SH, —NHCH$_3$, —N(CH$_3$)$_2$, —OCH$_3$ or —SCH$_3$;

R$^3$ is selected from the group consisting of hydrogen, halo, —OR$^a$, SR$^a$, $(C_1-C_8)$alkyl, cyano, nitro, trifluoromethyl, trifluoromethoxy, $(C_3-C_8)$cycloalkyl, heterocycle, hetrocycle$(C_1-C_8)$alkyl, aryl, aryl$(C_1-C_8)$alkyl, heteroaryl, heteroaryl$(C_1-C_8)$alkyl, —CO$_2$R$^a$, R$^a$C (=O)O—, R$^a$C(=O)—, —OCO$_2$R$^a$, R$^a$R$^b$NC(=O) O—, R$^b$OC(=O)N(R$^a$)—, R$^a$R$^b$N—, R$^a$R$^b$NC (=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, and R$^a$S(=O)$_2$—; or if the ring formed from the group CR$^3$R$^4$R$^5$ is aryl or heteroaryl or partially unsaturated, then R$^3$ can be absent;

R$^4$ and R$^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —S(O)$_2$— or amine (—NR$^a$—) in the ring, wherein any ring comprising R$^4$ and R$^5$ is optionally further substituted with from 1 to 14 R$^6$ groups; wherein each R$^6$ is independently selected from the group consisting of halo, —OR$^a$, —SR$^a$, substituted or unsubstituted $(C_1-C_8)$alkyl, cyano, nitro, trifluoromethyl, trifluoromethoxy, $(C_3-C_8)$cycloalkyl, $(C_6-C_{12})$ bicycloalkyl, heterocycle, hetrocyclyl$(C_1-C_8)$alkyl, aryl, aryl$(C_1-C_8)$alkyl, heteroaryl, heteroaryl$(C_1-C_8)$ alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC (=S)—, R$^a$C(=S)—, —SSR$^a$, R$^a$S(=O)— or two R$^6$ groups and the atom to which they are attached combined to form C=O or C=S, or wherein two R$^6$ groups together with the atom or atoms to which they are attached can form a carbocyclic or heterocyclic ring;

R$^9$ and R$^{10}$ are each independently selected from the group consisting of hydrogen, halogen, —NH$_2$, —OH, —SH, —NHCH$_3$, —N(CH$_3$)$_2$, —OCH$_3$, —SCH$_3$, $(C_1-C_8)$alkyl, aryl and aryl$(C_1-C_8)$alkyl, wherein R$^9$ and R$^{10}$ are optionally substituted with 1 to 4 substituents of R$^a$, wherein the alkyl is optionally interrupted by 1 to 4 heteroatoms selected from —O—, —S—, —SO—, —S(O)$_2$— or amino (—NR$^a$—), or where R$^9$ and R$^{10}$ are independently absent, with the proviso that R$^a$ is not SH or halogen in the case where the R$^9$ or R$^{10}$ to which R$^a$ is bound is halogen, —NH$_2$, —OH, —SH, —NHCH$_3$, —N(CH$_3$)$_2$, —OCH$_3$ or —SCH$_3$;

R$^a$ and R$^b$ are each independently selected from the group consisting of hydrogen, halogen, —NH$_2$, —OH, —SH, —NHCH$_3$, —N(CH$_3$)$_2$, —OCH$_3$, —SCH$_3$, propargyl, cyano, —OS(O$_2$)H, —OS(O$_2$)OH, —OS(O$_2$)CH$_3$, —OS(O$_2$)OCH$_3$, $(C_1-C_8)$alkyl, aryl, aryl$(C_1-C_8)$alkyl, $(C_3-C_8)$cycloalkyl, $(C_6-C_{12})$bicycloalkyl, cycloalkyl $(C_1-C_8)$alkyl, bicycloalkyl$(C_6-C_{12})$alkyl, heteroaryl and heteroaryl$(C_1-C_8)$alkyl, wherein the alkyl and cycloalkyl are optionally interrupted with 1–4 heteroatoms selected from the group consisting of —O—, —S—, —SO—, —S(O)$_2$— and amino (—NR$^c$—); and wherein the alkyl, cycloalkyl, aryl and heteroaryl are optionally substituted with 1, 2, 3 or 4 substituents selected from the group consisting of —OR$^c$, —NR$^c$R$^c$, SR$^c$, cyano, —OS(O$_2$)H, —OS(O$_2$)OH, —OS(O$_2$)CH$_3$ and —OS(O$_2$)OCH$_3$, provided that the point of attachment of R$^a$ or R$^b$ is not a heteroatom when it is attached to another heteroatom;

R$^c$ is selected from the group consisting of hydrogen and $(C_1-C_8)$alkyl; and m is 0 to 8; n is 0, 1, 2 or 3, provided that when m is 0, Z is not halogen, cyano, or nitro or is not attached via a heteroatom, and when n is 0, Y is not —NR$^4$R$^5$; or a pharmaceutically acceptable salt thereof, optionally in the form of a single stereoisomer or mixture of stereoisomers thereof.

32. The compound of claim 31, wherein R$^7$ is selected from the group consisting of hydrogen, methyl, ethyl, propyl, butyl, 3-pentyl, iso-propyl, iso-butyl, sec-butyl, tert-butyl, phenyl and benzyl.

33. The compound of claim 32, wherein R$^7$ is hydrogen, methyl, 3-pentyl or sec-butyl.

34. The compound of claim 1, wherein —NR$^7$R$^8$ is selected from the group consisting of amino, methylamino, dimethylamino, ethylamino, 3-pentylamino, (diphenylethyl)-amino, (pyridylmethyl)-amino, diethylamino and benzylamino.

35. The compound of claim 34, wherein —NR$^7$R$^8$ is selected from the group consisting of amino, methylamino, dimethylamino, ethylamino, diethylamino, 3-pentylamino and benzylamino.

36. The compound of claim 35, wherein —NR$^7$R$^8$ is amino.

37. The compound of claim 31, wherein R$^7$ is selected from the group consisting of benzyl, phenethyl, phenylpropyl and each is optionally substituted with from 1, 2 or 3 substituents of R$^a$.

38. The compound of claim 37, wherein R$^7$ is selected from the group consisting of benzyl, phenethyl, phenylpropyl and each is optionally substituted with from 1, 2 or 3 substituents of R$^a$ selected from the group consisting of methyl, ethyl, propyl, and methoxy.

39. The compound of claim 38, wherein R$^7$ is benzyl and R$^a$ is methoxy.

40. The compound of claim 1, wherein R$^9$ is independently selected from the group consisting of hydrogen, fluoro, —OH, —CH$_2$OH, —OCH$_3$, —NH$_2$, —NHCH$_3$, and —N(CH$_3$)$_2$.

41. The compound of claim 40, wherein R$^9$ is independently hydrogen or OH.

42. The compound of claim 1, wherein each R$^{10}$ is independently selected from the group consisting of hydrogen, fluoro, (C$_1$–C$_8$)alkyl, aryl, and aryl(C$_1$–C$_8$)alkylene-.

43. The compound of claim 42, wherein R$^{10}$ is independently selected from the group consisting of hydrogen, (C$_1$–C$_8$)alkyl, and benzyl.

44. The compound of claim 43, wherein R$^{10}$ is hydrogen.

45. The compound of claim 1, wherein R$^a$ and R$^b$ are each independently selected from the group consisting of hydrogen, (C$_1$–C$_4$)alkyl, aryl and aryl(C$_1$–C$_8$)alkylene.

46. The compound of claim 45, wherein R$^a$ and R$^b$ are each independently selected from the group consisting of hydrogen, methyl, ethyl, phenyl and benzyl.

47. The compound of claim 45, wherein R$^a$ is (C$_1$–C$_8$) alkyl.

48. The compound of claim 47, wherein R$^a$ is selected from the group consisting of methyl, ethyl, propyl and butyl.

49. The compound of claim 1, wherein Y is —CR$^3$R$^4$R$^5$ or NR$^4$R$^5$, and is selected from the group consisting of:

wherein q is 0, 1, 2, 3 or 4; R$^3$ is selected from the group consisting of hydrogen, halo, —OR$^a$, —SR$^a$, (C$_1$–C$_8$)alkyl, cyano, nitro, trifluoromethyl, trifluoromethoxy, (C$_3$–C$_8$)cycloalkyl, heterocycle, hetrocycle(C$_1$–C$_8$)alkyl, aryl, aryl (C$_1$–C$_8$)alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N (R$^b$)—, R$^a$R$^b$NC(=S)N(R$^b$)—, R$^a$OC(=S)—, R$^a$C (=S)—, —SSR$^a$, R$^a$S(=O)—, R$^a$S(=O)$_2$—; and each R$^6$ is independently selected from the group consisting of halo, —OR$^a$, —SR$^a$, substituted or unsubstituted (C$_1$–C$_8$)alkyl, cyano, nitro, trifluoromethyl, trifluoromethoxy, (C$_1$–C$_8$)cycloalkyl, (C$_6$–C$_{12}$)bicycloalkyl, heterocycle, hetrocyclyl (C$_1$–C$_8$)alkyl, aryl, aryl(C$_1$–C$_8$)alkyl, heteroaryl, heteroaryl (C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC (=O)N(R$^b$)—, R$^a$R$^b$NC(=S)N(R$^b$)—, R$^a$OC(=S)—, R$^a$C (=S)—, —SSR$^a$, and R$^a$S(=O)—, provided that R$^6$ is not halogen or a heteroatom when R$^6$ is attached to a heteroatom.

50. The compound of claim 1, wherein Y is —CR$^3$R$^4$R$^5$ or NR$^4$R$^5$ and is selected from the group consisting of:

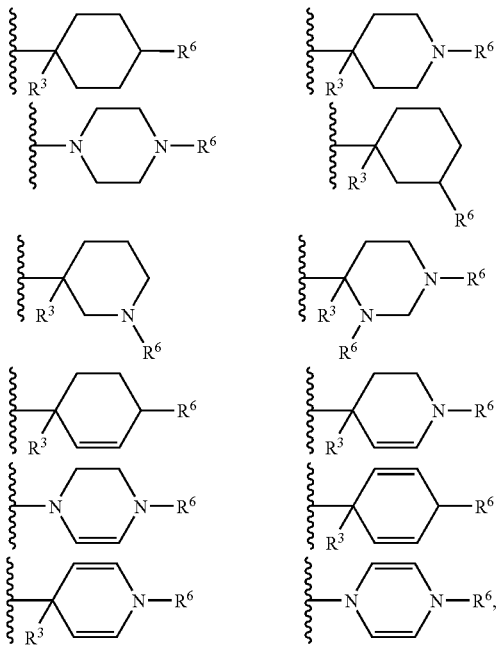

wherein R$^3$ is selected from the group consisting of hydrogen, halo, —OR$^a$, —SR$^a$, (C$_1$–C$_8$)alkyl, cyano, nitro, trifluoromethyl, trifluoromethoxy, (C$_3$–C$_8$)cycloalkyl, heterocycle, hetrocycle(C$_1$–C$_8$)alkyl, aryl, aryl(C$_1$–C$_8$)alkyl, heteroaryl, heteroaryl(C$_1$–C$_8$)alkyl, —CO$_2$R$^a$, R$^a$C(=O) O—, R$^a$C(=O)—, —OCO$_2$R$^a$, R$^a$R$^b$NC(=O)O—, R$^b$OC (=O)N(R$^a$)—, R$^a$R$^b$N—, R$^a$R$^b$NC(=O)—, R$^a$C(=O)N (R$^b$), R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, and R$^a$S (=O)$_2$—; and each R$^6$ is independently selected from the group consisting of halo, —OR$^a$, —SR$^a$, substituted or unsubstituted (C$_1$–C$_8$)alkyl, cyano, nitro, trifluoromethyl, trifluoromethoxy, (C$_3$–C$_8$)cycloalkyl, (C$_6$–C$_{12}$)bicycloalkyl, heterocycle, hetrocyclyl(C$_1$–C$_8$)alkyl, aryl, aryl(C$_1$–C$_8$) alkyl, heteroaryl, heteroaryl(C$_1$–C$_8$)alkyl, —CO$_2$R$^a$, R$^a$C (=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, and R$^a$S(=O)—.

51. The compound of claim 1, wherein the ring formed by R$^a$R$^b$ together with the atom to which they are attached is selected from: 2-methylcyclohexan-1-yl, 2,2-dimethylcyclohexan-1-yl, 2-ethylcyclohexan-1-yl, 2,2-diethylcyclohexan-1-yl, 2-tert-butylcyclohexan-1-yl, 2-phenylcyclohexan-1-yl, 3-methylcyclohexan-1-yl, 3-ethylcyclohexan-1-yl, 3,3-dimethylcyclohexan-1-yl, 4-methylcyclohexan-1-yl, 4-ethylcyclohexan-1-yl, 4,4-dimethylcyclohexan-1-yl, 4-tert-butylcyclohexan-1-yl, 4-phenylcyclohexan-1-yl, 3,3,5,5-tetramethylcyclohexan-1-yl, 2,4-dimethylcyclopentan-1-yl, 4-(carboxyl)cyclohexan-1-yl, 4-(carboxymethyl)cyclohexan-1-yl and 4-(carboxyethyl)cyclohexan-1-yl.

52. The compound of claim 1, wherein the ring formed by R$^a$R$^b$ together with the atom to which they are attached is selected from: piperidin-4-yl, 1-carboxypiperiden-4-yl, 1-(methoxycarbonyl)piperidin-4-yl, 1-(ethoxycarbonyl)piperidin-4-yl, 1-(n-propoxycarbonyl)piperidin-4-yl, 1-(2,2-dimethylpropoxycarbonyl)piperidin-4-yl, piperidin-1-yl, 4-carboxypiperiden-1-yl, 4-(methoxycarbonyl)piperidine-1-yl, 4-(ethoxycarbonyl)piperidine-1-yl, 4-(n-propoxy)piperidine-1-yl, 4-(2,2-dimethylpropoxycarbonyl)piperidine-1-yl, piperidin-3-yl, 1-carboxypiperidene-3-yl, 1-(methoxycarbonyl)piperidine-3-yl, 1-(ethoxycarbonyl)piperidine-3-yl, 1-(n-propoxycarbonyl)piperidine-3-yl, 1-(2,2-dimethylpropoxycarbonyl)piperidine-3-yl, 3-carboxypiperidene-1-yl, 3-(methoxycarbonyl)piperidine-1-yl, 3-(ethoxycarbonyl)piperidine-1-yl, 3-(n-propoxycarbonyl)piperidine-1-yl, 3-(2,2-dimethylpropoxycarbonyl)piperidine-1-yl, piperazin-1-yl, 1-caboxypiperazin-4-yl, 1-(methoxycarbonyl)piperazin-4-yl, 1-(ethoxycarbonyl)piperazin-4-yl and 1-(n-propoxycarbonyl)piperazin-4-yl.

53. The compound of claim 1, wherein the ring formed by R$^a$R$^b$ together with the atom to which they are attached is selected from: 2-methylcyclohexan-1-yl, 2,2-dimethylcyclohexan-1-yl, 2-ethylcyclohexan-1-yl, 2,2-diethylcyclohexan-1-yl, 2-tert-butylcyclohexan-1-yl, 2-phenylcyclohexan-1-yl, 3-methylcyclohexan-1-yl, 3-ethylcyclohexan-1-yl, 3,3-dimethylcyclohexan-1-yl, 4-methylcyclohexan-1-yl, 4-ethylcyclohexan-1-yl, 4,4-dimethylcyclohexan-1-yl, 4-tert-butylcyclohexan-1-yl, 4-phenylcyclohexan-1-yl, 3,3,5,5-tetramethylcyclohexan-1-yl, 2,4-dimethylcyclopentan-1-yl, 4-(carboxyl)cyclohexan-1-yl, 4-(carboxymethyl)cyclohexan-1-yl, 4-(carboxyethyl)cyclohexan-1-yl, piperidin-4-yl, 1-(methoxycarbonyl)piperidin-4-yl, 1-(2,2-dimethylpropoxycarbonyl)piperidin-4-yl, piperidin-1-yl, 4-(methoxycarbonyl)piperidine-1-yl, 4-(2,2-dimethylpropoxycarbonyl)piperidine-1-yl, piperidin-3-yl, 1-(methoxycarbonyl)piperidine-3-yl, 1-(2,2-dimethylpropoxycarbonyl)piperidine-3-yl, 3-(methoxycarbonyl)piperidine-1-yl and 3-(2,2-dimethylpropoxycarbonyl)piperidine-1-yl.

54. The compound of claim 2, wherein Z is an aryl, (C$_3$–C$_8$)cycloalkyl, (C$_6$–C$_{12}$)bicycloalkyl, or (C$_3$–C$_{20}$)polycyclyl, wherein the ring atoms are optionally interrupted by 1–8 heteroatoms selected from the group consisting of —O—, —S—, —SO—, —S(O)$_2$— and amino (—NR$^a$—).

55. A compound of formula II:

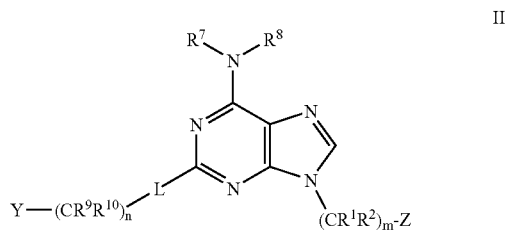

wherein R$^1$ and R$^2$ are hydrogen, m is 0, 1, 2 or 3 and Z is selected from the group consisting of furan, dihydro-furan, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with from 1 to 10 R$^a$ groups;

L is a linker selected from the group consisting of —(C$_1$–C$_3$)alkyl-C≡C—, —C≡C—(C$_1$–C$_3$)alkyl-, —(CH$_2$)$_{1-3}$—CH=CH—, —CH=CH—(CH$_2$)$_{1-3}$—, —(CH$_2$)$_{1-2}$—CH=CH—CH$_2$— and —CH$_2$—CH=CH—(CH$_2$)$_{1-2}$—;

Y is —CR$^3$R$^4$R$^5$ or NR$^4$R$^5$;

R$^3$ is selected from the group consisting of hydrogen, halo, —OR$^a$, SR$^a$, (C$_1$–C$_8$)alkyl, cyano, nitro, trifluoromethyl, trifluoromethoxy, (C$_3$–C$_8$)cycloalkyl, heterocycle, hetrocycle(C$_1$–C$_8$)alkyl, aryl, aryl(C$_1$–C$_8$)alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, R$^a$S(=O)—, and R$^a$S(=O)$_2$—; or if the ring formed from the group CR$^3$R$^4$R$^5$ is aryl or heteroaryl or partially unsaturated, then R$^3$ can be absent;

R$^4$ and R$^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —S(O)$_2$— or amine (—NR$^a$—) in the ring, wherein any ring comprising R$^4$ and R$^5$ is optionally further substituted with from 1 to 14 R$^6$ groups; wherein each R$^6$ is independently selected from the group consisting of halo, —OR$^a$, —SR$^a$, substituted or unsubstituted (C$_1$–C$_8$)alkyl, cyano, nitro, trifluoromethyl, trifluoromethoxy, (C$_3$–C$_8$)cycloalkyl, (C$_6$–C$_{12}$)bicycloalkyl, heterocycle, hetrocyclyl(C$_1$–C$_8$)alkyl, aryl, aryl(C$_1$–C$_8$)alkyl, heteroaryl, heteroaryl(C$_1$–C$_8$)alkyl, —CO$_2$R$^a$, R$^a$C(=O)O—, R$^a$C(=O)—, —OCO$_2$R$^a$, R$^a$R$^b$NC(=O)O—, R$^b$OC(=O)N(R$^a$)—, R$^a$R$^b$N—, R$^a$R$^b$NC(=O)—, R$^a$C(=O)N(R$^b$)—, R$^a$R$^b$NC(=O)N(R$^b$)—, R$^a$R$^b$NC(=S)N(R$^b$)—, R$^a$OC(=S)—, R$^a$C(=S)—, —SSR$^a$, and R$^a$S(=O)— or two $R^6$ groups and the atom to which they are attached combined to form C=O or C=S, or wherein two $R^6$ groups together with the atom or atoms to which they are attached can form a carbocyclic or heterocyclic ring;

$R^7$ and $R^8$ are each independently hydrogen, $(C_1-C_8)$ alkyl, $(C_3-C_8)$cycloalkyl, aryl or aryl$(C_1-C_8)$alkylene, heteroaryl, heteroaryl$(C_1-C_8)$alkylene; or wherein $R^7$ and $R^8$ together with the nitrogen atom to which they attach form a heterocycle or heteroaromatic ring;

$R^9$ and $R^{10}$ are each independently selected from the group consisting of hydrogen, halogen, —$NH_2$, —OH, —SH, —$NHCH_3$, —$N(CH_3)_2$, —$OCH_3$, —$SCH_3$, $(C_1-C_8)$alkyl, aryl and aryl$(C_1-C_8)$alkyl, wherein $R^9$ and $R^{10}$ are optionally substituted with 1 to 4 substituents of $R^a$, wherein the alkyl is optionally interrupted by 1 to 4 heteroatoms selected from —O—, —S—, —SO—, —$S(O)_2$— or amino (—$NR^a$—), or where $R^9$ and $R^{10}$ are independently absent, with the proviso that $R^a$ is not SH or halogen in the case where the $R^9$ or $R^{10}$ to which $R^a$ is bound is halogen, —$NH_2$, —OH, —SH, —$NHCH_3$, —$N(CH_3)_2$, —$OCH_3$ or —$SCH_3$;

$R^a$ and $R^b$ are each independently selected from the group consisting of hydrogen, halogen, —$NH_2$, —OH, —SH, —$NHCH_3$, —$N(CH_3)_2$, —$OCH_3$, —$SCH_3$, propargyl, cyano, —$OS(O_2)H$, —$OS(O_2)OH$, —$OS(O_2)CH_3$, —$OS(O_2)OCH_3$, $(C_1-C_8)$alkyl, aryl, aryl$(C_1-C_8)$alkyl, $(C_3-C_8)$cycloalkyl, $(C_6-C_{12})$bicycloalkyl, cycloalkyl$(C_1-C_8)$alkyl, bicycloalkyl$(C_6-C_{12})$alkyl, heteroaryl and heteroaryl$(C_1-C_8)$alkyl, wherein the alkyl and cycloalkyl are optionally interrupted with 1–4 heteroatoms selected from the group consisting of —O—, —S—, —SO—, —$S(O)_2$— and amino (—$NR^c$—); and wherein the alkyl, cycloalkyl, aryl and heteroaryl are optionally substituted with 1, 2, 3 or 4 substituents selected from the group consisting of —$OR^c$, —$NR^cR^c$, $SR^c$, cyano, —$OS(O_2)H$, —$OS(O_2)OH$, —$OS(O_2)CH_3$ and —$OS(O_2)OCH_3$, provided that the point of attachment of $R^a$ or $R^b$ is not a heteroatom when it is attached to another heteroatom;

$R^c$ is selected from the group consisting of hydrogen and $(C_1-C_8)$alkyl; and m is 0 to 8; n is 0, 1, 2 or 3, provided that when n is 0, Z is not attached via a heteroatom, and when n is 0, Y is not —$NR^4R^5$; or a pharmaceutically acceptable salt thereof, optionally in the form of a single stereoisomer or mixture of stereoisomers thereof.

56. A compound selected from the group:
9-Cyclopropylmethyl-2-{2-[1(S)-hydroxy-3(R)-methyl-1-cyclohexyl]ethyn-1-yl}adenine (1);
2-{2-[1(S)-Hydroxy-3(R)-methyl-1-cyclohexyl]ethyn-1-yl}-9-propargyladenine (2);
9-Cyclopentyl-2-{2-[1(S)-hydroxy-3(R)-methyl-1-cyclohexyl]ethyn-1-yl}adenine (3);
9-Cyanomethyl-2-{2-[1(S)-hydroxy-3(R)-methyl-1-cyclohexyl]ethyn-1-yl}adenine (4);
2-{2-[1(S)-Hydroxy-3(R)-methyl-1-cyclohexyl]ethyn-1-yl}-9-(4-methoxybenzyl)adenine (5);
9-(3,4-Dichlorobenzyl)-2-{2-[1(S)-hydroxy-3(R)-methyl-1-cyclohexyl]ethyn-1-yl}adenine (6);
2-{2-[1(S)-Hydroxy-3(R)-methyl-1-cyclohexyl]ethyn-1-yl}-9-(4-trifluoromethylbenzyl)adenine (7);
9-(3,5-Dimethyl-isoxazol-4-ylmethyl)-2-{2-[1(S)-hydroxy-3(R)-methyl-1-cyclohexyl]ethyn-1-yl}adenine (8);
2-{2-[1(S)-Hydroxy-3(R)-methyl-1-cyclohexyl]ethyn-1-yl}-9-[2-(trifluoromethylphenyl)thiazol-4-ylmethyl]adenine (9);
2-{2-[Hydroxy-adamantan-2-yl]ethyn-1-yl}-9-(3-(thiophen-2-yl)prop-2-ynyl)adenine (10);
9-Cyclopropylmethyl-2-{2-[1(S)-hydroxy-3(R)-methyl-1-cyclohexyl]ethyn-1-yl}-N6-(3-pentyl)adenine (14);
9-Cyclopentyl-2-{2-[1(S)-hydroxy-3(R)-methyl-1-cyclohexyl]ethyn-1-yl}-N6-(3-pentyl)adenine (15);
9-Allyl-2-{2-[1(S)-hydroxy-3(R)-methyl-1-cyclohexyl]ethyn-1-yl}-N6-(3-pentyl)adenine (16);
2-{2-[1(S)-Hydroxy-3(R)-methyl-1-cyclohexyl]ethyn-1-yl}-N6-(3-pentyl)-9-(propargyl)adenine (17);
2-{2-[1(S)-Hydroxy-3(R)-methyl-1-cyclohexyl]ethyn-1-yl}-N6-(3-pentyl)-9-(pent-4-ynyl)adenine (18);
9-(2-Chloroethyl)-2-{2-[1(S)-hydroxy-3(R)-methyl-1-cyclohexyl]ethyn-1-yl}-N6-(3-pentyl)adenine (21);
9-([1,3]-Dioxolan-2-ylmethyl)-2-{2-[1(S)-hydroxy-3(R)-methyl-1-cyclohexyl]ethyn-1-yl}-N6-(3-pentyl)adenine (22);
2-{2-[1(S)-Hydroxy-3(R)-methyl-1-cyclohexyl]ethyn-1-yl}-N6-(3-pentyl)-9-(tetrahydro-pyran-2-ylmethyl)adenine (23);
2-{2-[1(S)-Hydroxy-3(R)-methyl-1-cyclohexyl]ethyn-1-yl}-N6-(3-pentyl)-9-(isopropylcarboxylate)adenine (24);
9-(Acetic acid ethyl ester)-2-{2-[1(S)-hydroxy-3(R)-methyl-1-cyclohexyl]ethyn-1-yl}-N6-(3-pentyl)adenine (25);
2-{2-[1(S)-Hydroxy-3(R)-methyl-1-cyclohexyl]ethyn-1-yl}-9-(2-oxo-oxazolidin-5-ylmethyl)-N6-(3-pentyl)adenine (26);
9-Benzyl-2-{2-[1(S)-hydroxy-3(R)-methyl-1-cyclohexyl]ethyn-1-yl}-N6-(3-pentyl)adenine (27);
2-{2-[1(S)-Hydroxy-3(R)-methyl-1-cyclohexyl]ethyn-1-yl}-N6-(3-pentyl)-9-(pyridin-3-ylmethyl)adenine (28);
2-{2-[1(S)-Hydroxy-3(R)-methyl-1-cyclohexyl]ethyn-1-yl}-9-(4-nitrobenzyl)-N6-(3-pentyl)adenine (29);
9-(3,5-Dimethyl-isoxazol-4-ylmethyl)-2-{2-[1(S)-hydroxy-3(R)-methyl-1-cyclohexyl]ethyn-1-yl}-N6-(3-pentyl)adenine (30);
2-{2-[1(S)-Hydroxy-3(R)-methyl-1-cyclohexyl]ethyn-1-yl}-9-(2-methyl-thiazol-5-ylmethyl)-N6-(3-pentyl)adenine (31);
N6-[(S)-(+)-sec-Butyl]-2-{2-[1(S)-hydroxy-3(R)-methyl-1-cyclohexyl]ethyn-1-yl}-9-propargyl-adenine (32);
N6-[(s)-(+)-sec-Butyl]-9-(3,5-dimethyl-isoxazol-4-ylmethyl)-2-{2-[1(S)-hydroxy-3(R)-methyl-1-cyclohexyl]ethyn-1-yl}adenine (33);
2-{2-[1(S)-Hydroxy-3(R)-methyl-1-cyclohexyl]ethyn-1-yl}-N6-[(s)-(–)-alpha-napthalen-1-yl-ethyl]-9-(propargyl)adenine (35);
2-{2-[1(S)-Hydroxy-3(R)-methyl-1-cyclohexyl]ethyn-1-yl}-N6-(3-methoxybenzyl)-9-(propargyl)adenine (36);
2-{2-[1(S)-Hydroxy-3(R)-methyl-1-cyclohexyl]ethyn-1-yl}-9-(propargyl)-N6-(pyridin-2-ylmethyl)adenine (37);
2-{2-[1(S)-Hydroxy-3(R)-methyl-1-cyclohexyl]ethyn-1-yl}-N6-[(methyl)(2-phenethyl)]-9-(propargyl)adenine (38);
9-Cyclopropylmethyl-2-{2-[hydroxy-adamantan-2-yl]ethyn-1-yl}adenine (45);
9-Cyclobutylmethyl-2-{2-[hydroxy-adamantan-2-yl]ethyn-1-yl}adenine (46);
9-Cyclopentylmethyl-2-{2-[hydroxy-adamantan-2-yl]ethyn-1-yl}adenine (47);

9-Cyclohexylmethyl-2-{2-[hydroxy-adamantan-2-yl]ethyn-1-yl}adenine (48);

9-Cyclobutyl-2-{2-[hydroxy-adamantan-2-yl]ethyn-1-yl}adenine (49);

9-Cyclopentyl-2-{2-[hydroxy-adamantan-2-yl]ethyn-1-yl}adenine (50);

2-{2-[Hydroxy-adamantan-2-yl]ethyn-1-yl}-9-propargyladenine (51);

2-{2-[Hydroxy-norbornan-2-yl]ethyn-1-yl}-9-propargyladenine;

9-(But-3-ynyl)-2-{2-[hydroxy-adamantan-2-yl]ethyn-1-yl}adenine (62); and

2-{3-[1-(Methoxycarbanoyl)piperidin-4-yl]propyn-1-yl}-9-propargyladenine (63); or a pharmaceutically acceptable salt thereof, optionally in the form of a single stereoisomer or mixture of stereoisomers thereof.

57. A compound selected from the group in Tables 1 to 7, or a pharmaceutically acceptable salt thereof, optionally in the form of a single stereoisomer or mixture of stereoisomers thereof wherein c-Pentyl is cyclopentyl and Me is methyl:

TABLE 1

| Compound | $(CR^1R^2)_m$-Z | $R^6$ |
|---|---|---|
| NC100 | Propargyl | $CH_2OH$ |
| NC101 | c-Pentyl | $CH_2OH$ |
| NC102 | Propargyl | $CO_2H$ |
| NC103 | c-Pentyl | $CO_2H$ |
| NC104 | Propargyl | $CO_2Me$ |
| NC105 | c-Pentyl | $CO_2Me$ |
| NC106 | Propargyl | $CH_2OAc$ |
| NC107 | c-Pentyl | $CH_2OAc$ |
| NC108 | Propargyl | $CH_2N(CH_3)_2$ |
| NC109 | c-Pentyl | $CH_2N(CH_3)_2$ |
| NC110 | Propargyl | $COOCH_2CH_2NHBoc$ |
| NC111 | c-Pentyl | $COOCH_2CH_2NHBoc$ |
| NC112 | Propargyl | $COOCH_2CH_2NH_2$ |
| NC113 | c-Pentyl | $COOCH_2CH_2NH_2$ |
| NC114 | Propargyl | $CONHCH_2CH_3$ |
| NC115 | c-Pentyl | $CONHCH_2CH_3$ |
| NC116 | Propargyl | $CONH_2$ |
| NC117 | c-Pentyl | $CONH_2$ |
| NC118 | Propargyl | CONHMe |
| NC119 | c-Pentyl | CONHMe |
| NC120 | Propargyl | Me, cis $CO_2Me$ |
| NC121 | c-Pentyl | Me, cis $CO_2Me$ |
| NC122 | Propargyl | Me, trans $CO_2Me$ |
| NC123 | c-Pentyl | Me, trans $CO_2Me$ |
| NC124 | Propargyl | $CH_2CH_3$ |
| NC125 | c-Pentyl | $CH_2CH_3$ |
| NC128 | Propargyl | $COCH_3$ |
| NC129 | c-Pentyl | $COCH_3$ |
| NC130 | Propargyl | $CHCH_3(OH)$ |
| NC131 | c-Pentyl | $CHCH_3(OH)$ |

TABLE 2

| Compound | $(CR^1R^2)_m$-Z | $R^6$ |
|---|---|---|
| NC134 | Propargyl | $CO_2tBu$ |
| NC135 | c-Pentyl | $CO_2tBu$ |
| NC136 | Propargyl | $CO_2Et$ |
| NC137 | c-Pentyl | $CO_2Et$ |
| NC138 | Propargyl | $CO_2iBu$ |
| NC139 | c-Pentyl | $CO_2iBu$ |
| NC140 | Propargyl | $CO_2iPr$ |
| NC141 | c-Pentyl | $CO_2iPr$ |
| 63 | Propargyl | COMe |
| NC142 | c-Pentyl | COMe |
| NC143 | Propargyl | $COC(CH_3)_3$ |
| NC144 | c-Pentyl | $COC(CH_3)_3$ |
| NC145 | Propargyl | $COCH_2(CH_3)_3$ |
| NC146 | c-Pentyl | $COCH_2(CH_3)_3$ |
| NC147 | Propargyl | $C(O)N(CH_3)_2$ |
| NC148 | c-Pentyl | $C(O)N(CH_3)_2$ |
| NC149 | Propargyl | $C(O)N(CH_3)Et$ |
| NC150 | c-Pentyl | $C(O)N(CH_3)Et$ |
| NC142 | Propargyl | $C(O)N(CH_3)iPr$ |
| NC143 | c-Pentyl | $C(O)N(CH_3)iPr$ |
| NC144 | Propargyl | $C(O)N(CH_3)iBu$ |
| NC145 | c-Pentyl | $C(O)N(CH_3)iBu$ |
| NC146 | Propargyl | $C(O)NH(CH_3)$ |
| NC147 | c-Pentyl | $C(O)NH(CH_3)$ |
| NC148 | Propargyl | $C(O)NH(Et)$ |
| NC149 | c-Pentyl | $C(O)NH(Et)$ |
| NC150 | Propargyl | $C(O)NH(iPr)$ |
| NC142 | c-Pentyl | $C(O)NH(iPr)$ |
| NC143 | Propargyl | $C(O)NH(iBu)$ |
| NC144 | c-Pentyl | $C(O)NH(iBu)$ |

TABLE 3

| Compound | $(CR^1R^2)_m$-Z | $R^6$ |
|---|---|---|
| NC153 | Propargyl | 2-$CH_3$ |
| NC154 | c-Pentyl | 2-$CH_3$ |
| NC155 | Propargyl | 2-$C(CH_3)_3$ |
| NC156 | c-Pentyl | 2-$C(CH_3)_3$ |
| NC157 | Propargyl | 2-$C_6H_5$ |
| NC158 | c-Pentyl | 2-$C_6H_5$ |
| 2 | Propargyl | 3-$CH_3$ |
| 3 | c-Pentyl | 3-$CH_3$ |
| NC159 | Propargyl | 3-$(CH_3)_2$ |
| NC160 | c-Pentyl | 3-$(CH_3)_2$ |
| NC161 | Propargyl | 3-$CH_2CH_3$ |
| NC162 | c-Pentyl | 3-$CH_2CH_3$ |

TABLE 3-continued

Structure: 6-(NR⁷R⁸)-purine with 2-alkynyl-(1-hydroxycyclohexyl) substituent bearing R⁶, and N9-(CR¹R²)ₘ-Z; R⁷, R⁸ = H

| Compound | (CR¹R²)ₘ-Z | R⁶ |
|---|---|---|
| NC163 | Propargyl | 3-(CH₃)₂, 5-(CH₃)₂ |
| NC164 | c-Pentyl | 3-(CH₃)₂, 5-(CH₃)₂ |
| NC165 | Propargyl | 4-CH₃ |
| NC166 | c-Pentyl | 4-CH₃ |
| NC167 | Propargyl | 4-C₂H₅ |
| NC168 | c-Pentyl | 4-C₂H₅ |
| NC169 | Propargyl | 4-C(CH₃)₃ |
| NC170 | c-Pentyl | 4-C(CH₃)₃ |
| NC171 | Propargyl | 4-C₆H₅ |
| NC172 | c-Pentyl | 4-C₆H₅ |

TABLE 4

Structure: 6-(NR⁷R⁸)-purine with 2-(propynyl-piperazinyl-R⁶) substituent, and N9-(CR¹R²)ₘ-Z; R⁷, R⁸ = H

| Compound | (CR¹R²)ₘ-Z | R⁶ |
|---|---|---|
| NC175 | Propargyl | cyclohexyl |
| NC176 | c-Pentyl | cyclohexyl |
| NC177 | Propargyl | CO₂Et |
| NC178 | c-Pentyl | CO₂Et |
| NC179 | Propargyl | CO₂tBu |
| NC180 | c-Pentyl | CO₂tBu |
| NC181 | Propargyl | COMe |
| NC182 | c-Pentyl | COMe |
| NC183 | Propargyl | CO₂iBu |
| NC184 | c-Pentyl | CO₂iBu |
| NC185 | Propargyl | 2-Pyrimidinyl |
| NC186 | c-Pentyl | 2-Pyrimidinyl |
| NC187 | Propargyl | COC(CH₃)₃ |
| NC188 | c-Pentyl | COC(CH₃)₃ |
| NC189 | Propargyl | COMe |
| NC190 | c-Pentyl | COMe |
| NC191 | Propargyl | COCH₂(CH₃)₃ |
| NC192 | c-Pentyl | COCH₂(CH₃)₃ |
| NC193 | Propargyl | COCH₃ |
| NC194 | c-Pentyl | COCH₃ |
| NC195 | Propargyl | C(O)N(CH₃)₂ |
| NC196 | c-Pentyl | C(O)N(CH₃)₂ |
| NC197 | Propargyl | C(O)N(CH₃)Et |
| NC198 | c-Pentyl | C(O)N(CH₃)Et |
| NC199 | Propargyl | C(O)N(CH₃)iPr |
| NC200 | c-Pentyl | C(O)N(CH₃)iPr |
| NC201 | Propargyl | C(O)N(CH₃)iBu |
| NC202 | c-Pentyl | C(O)N(CH₃)iBu |
| NC203 | Propargyl | C(O)NH(CH₃) |
| NC204 | c-Pentyl | C(O)NH(CH₃) |
| NC205 | Propargyl | C(O)NH(Et) |
| NC206 | c-Pentyl | C(O)NH(Et) |

TABLE 4-continued

| Compound | (CR¹R²)ₘ-Z | R⁶ |
|---|---|---|
| NC207 | Propargyl | C(O)NH(iPr) |
| NC208 | c-Pentyl | C(O)NH(iPr) |
| NC209 | Propargyl | C(O)NH(iBu) |
| NC210 | c-Pentyl | C(O)NH(iBu) |

TABLE 5

Structure: 6-(NR⁷R⁸)-purine with 2-(propynyl-piperidinyl-R⁶) substituent, and N9-(CR¹R²)ₘ-Z; R⁷, R⁸ = H

| Compound | (CR¹R²)ₘ-Z | R⁶ |
|---|---|---|
| NC211 | Propargyl | CH₂OH |
| NC212 | c-Pentyl | CH₂OH |
| NC213 | Propargyl | CO₂H |
| NC214 | c-Pentyl | CO₂H |
| NC215 | Propargyl | CO₂Me |
| NC216 | c-Pentyl | CO₂Me |
| NC217 | Propargyl | CO₂Et |
| NC218 | c-Pentyl | CO₂Et |
| NC219 | Propargyl | CH₂OAc |
| NC220 | c-Pentyl | CH₂OAc |
| NC221 | Propargyl | CH₂N(CH₃)₂ |
| NC222 | c-Pentyl | CH₂N(CH₃)₂ |
| NC223 | Propargyl | COOCH₂CH₂NHBoc |
| NC224 | c-Pentyl | COOCH₂CH₂NHBoc |
| NC225 | Propargyl | COOCH₂CH₂NH₂ |
| NC226 | c-Pentyl | COOCH₂CH₂NH₂ |
| NC227 | Propargyl | CONHCH₂CH₃ |
| NC228 | c-Pentyl | CONHCH₂CH₃ |
| NC229 | Propargyl | CONH₂ |
| NC230 | c-Pentyl | CONH₂ |
| NC231 | Propargyl | CONHMe |
| NC232 | c-Pentyl | CONHMe |
| NC233 | Propargyl | CH₂CH₃ |
| NC234 | c-Pentyl | CH₂CH₃ |
| NC235 | Propargyl | COCH₃ |
| NC236 | c-Pentyl | COCH₃ |
| NC237 | Propargyl | CHCH₃(OH) |
| NG238 | c-Pentyl | CHCH₃(OH) |

TABLE 6

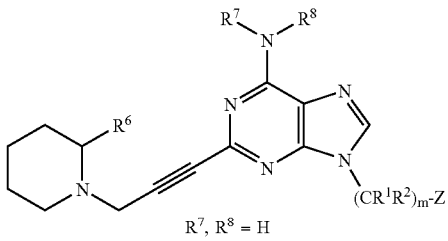

R$^7$, R$^8$ = H

| Compound | (CR$^1$R$^2$)$_m$-Z | R$^6$ |
|---|---|---|
| NC239 | Propargyl | CH$_2$OH |
| NC240 | c-Pentyl | CH$_2$OH |
| NC241 | Propargyl | CO$_2$H |
| NC242 | c-Pentyl | CO$_2$H |
| NC243 | Propargyl | CO$_2$Me |
| NC244 | c-Pentyl | CO$_2$Me |
| NC245 | Propargyl | CH$_2$OAc |
| NC246 | c-Pentyl | CH$_2$OAc |
| NC247 | Propargyl | CH$_2$N(CH$_3$)$_2$ |
| NC248 | c-Pentyl | CH$_2$N(CH$_3$)$_2$ |
| NC249 | Propargyl | COOCH$_2$CH$_2$NHBoc |
| NC250 | c-Pentyl | COOCH$_2$CH$_2$NHBoc |
| NC251 | Propargyl | COOCH$_2$CH$_2$NH$_2$ |
| NC252 | c-Pentyl | COOCH$_2$CH$_2$NH$_2$ |
| NC253 | Propargyl | CONHCH$_2$CH$_3$ |
| NC254 | c-Pentyl | CONHCH$_2$CH$_3$ |
| NC255 | Propargyl | CONH$_2$ |
| NC256 | c-Pentyl | CONH$_2$ |
| NC257 | Propargyl | CONHMe |
| NC258 | c-Pentyl | CONHMe |
| NC259 | Propargyl | CH$_2$CH$_3$ |
| NC260 | c-Pentyl | CH$_2$CH$_3$ |
| NC261 | Propargyl | COCH$_3$ |
| NC262 | c-Pentyl | COCH$_3$ |
| NC263 | Propargyl | CHCH$_3$(OH) |
| NC264 | c-Pentyl | CHCH$_3$(OH) |

TABLE 7

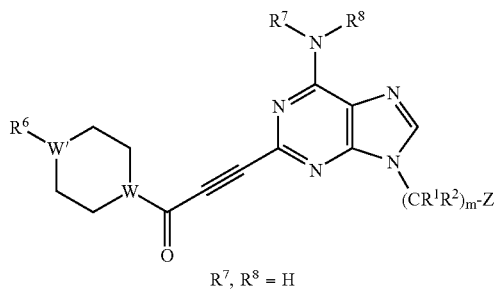

R$^7$, R$^8$ = H

| Compound | (CR$^1$R$^2$)$_m$-Z | W | W' | R$^6$ |
|---|---|---|---|---|
| NC265 | Propargyl | CH | CH | CO$_2$Me |
| NC266 | c-Pentyl | CH | N | CO$_2$Me |
| NC267 | Propargyl | N | CH | CO$_2$Me |
| NC268 | c-Pentyl | N | N | CO$_2$Me |
| NC269 | Propargyl | CH | CH | CO$_2$Me |
| NC270 | c-Pentyl | CH | N | CO$_2$Me |
| NC271 | Propargyl | N | CH | CO$_2$Me |
| NC272 | c-Pentyl | N | N | CO$_2$Me |
| NC273 | Propargyl | CH | CH | CH$_2$OH |
| NC274 | c-Pentyl | CH | N | CH$_2$OH |
| NC275 | Propargyl | N | CH | CH$_2$OH |
| NC276 | c-Pentyl | N | N | CH$_2$OH |
| NC277 | Propargyl | CH | CH | CH$_2$OH |
| NC278 | c-Pentyl | CH | N | CH$_2$OH |
| NC279 | Propargyl | N | CH | CH$_2$OH |
| NC280 | c-Pentyl | N | N | CH$_2$OH |
| NC281 | Propargyl | CH | CH | CO$_2$H |

TABLE 7-continued

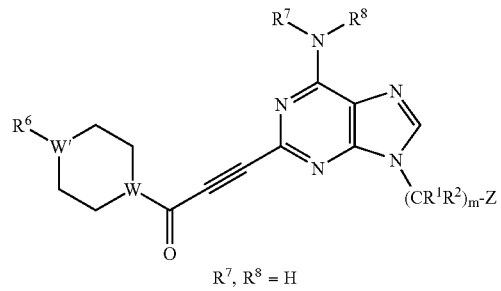

R$^7$, R$^8$ = H

| Compound | (CR$^1$R$^2$)$_m$-Z | W | W' | R$^6$ |
|---|---|---|---|---|
| NC282 | c-Pentyl | CH | N | CO$_2$H |
| NC283 | Propargyl | N | CH | CO$_2$H |
| NC284 | c-Pentyl | N | N | CO$_2$H |
| NC285 | Propargyl | CH | CH | CO$_2$H |
| NC286 | c-Pentyl | CH | N | CO$_2$H |
| NC287 | Propargyl | N | CH | CO$_2$H |
| NC288 | c-Pentyl | N | N | CO$_2$H |
| NC289 | Propargyl | CH | CH | CH$_2$OAc |
| NC290 | c-Pentyl | CH | N | CH$_2$OAc |
| NC291 | Propargyl | N | CH | CH$_2$OAc |
| NC292 | c-Pentyl | N | N | CH$_2$OAc |
| NC293 | Propargyl | CH | CH | CH$_2$OAc |
| NC294 | c-Pentyl | CH | N | CH$_2$OAc |
| NC295 | Propargyl | N | CH | CH$_2$OAc |
| NC296 | c-Pentyl | N | N | CH$_2$OAc |
| NC297 | Propargyl | CH | CH | CONH$_2$ |
| NC298 | c-Pentyl | CH | N | CONH$_2$ |
| NC299 | Propargyl | N | CH | CONH$_2$ |
| NC300 | c-Pentyl | N | N | CONH$_2$ |
| NC301 | Propargyl | CH | CH | CONH$_2$ |
| NC302 | c-Pentyl | CH | N | CONH$_2$ |
| NC303 | Propargyl | N | CH | CONH$_2$ |
| NC304 | c-Pentyl | N | N | CONH$_2$ |
| NC305 | Propargyl | CH | CH | CONHMe |
| NC306 | c-Pentyl | CH | N | CONHMe |
| NC307 | Propargyl | N | CH | CONHMe |
| NC308 | c-Pentyl | N | N | CONHMe |
| NC309 | Propargyl | CH | CH | CONHMe |
| NC310 | c-Pentyl | CH | N | CONHMe |
| NC311 | Propargyl | N | CH | CONHMe |
| NC312 | c-Pentyl | N | N | CONHMe |
| NC313 | Propargyl | CH | CH | CO$_2$tBu |
| NC314 | c-Pentyl | CH | N | CO$_2$tBu |
| NC315 | Propargyl | N | CH | CO$_2$tBu |
| NC316 | c-Pentyl | N | N | CO$_2$tBu |
| NC317 | Propargyl | CH | CH | CO$_2$tBu |
| NC318 | c-Pentyl | CH | N | CO$_2$tBu |
| NC319 | Propargyl | N | CH | CO$_2$tBu |
| NC320 | c-Pentyl | N | N | CO$_2$tBu |
| NC321 | Propargyl | CH | CH | CO$_2$Et |
| NC322 | c-Pentyl | CH | N | CO$_2$Et |
| NC323 | Propargyl | N | CH | CO$_2$Et |
| NC324 | c-Pentyl | N | N | CO$_2$Et |
| NC325 | Propargyl | CH | CH | CO$_2$Et |
| NC326 | c-Pentyl | CH | N | CO$_2$Et |
| NC327 | Propargyl | N | CH | CO$_2$Et |
| NC328 | c-Pentyl | N | N | CO$_2$Et |
| NC329 | Propargyl | CH | CH | CO$_2$iBu |
| NC330 | c-Pentyl | CH | N | CO$_2$iBu |
| NC331 | Propargyl | N | CH | CO$_2$iBu |
| NC332 | c-Pentyl | N | N | CO$_2$iBu |
| NC333 | Propargyl | CH | CH | CO$_2$iBu |
| NC334 | c-Pentyl | CH | N | CO$_2$iBu |
| NC335 | Propargyl | N | CH | CO$_2$iBu |
| NC336 | c-Pentyl | N | N | CO$_2$iBu |
| NC337 | Propargyl | CH | CH | CO$_2$iPr |
| NC338 | c-Pentyl | CH | N | CO$_2$iPr |
| NC339 | Propargyl | N | CH | CO$_2$iPr |
| NC340 | c-Pentyl | N | N | CO$_2$iPr |
| NC341 | Propargyl | CH | CH | CO$_2$iPr |
| NC342 | c-Pentyl | CH | N | CO$_2$iPr |
| NC343 | Propargyl | N | CH | CO$_2$iPr |

TABLE 7-continued

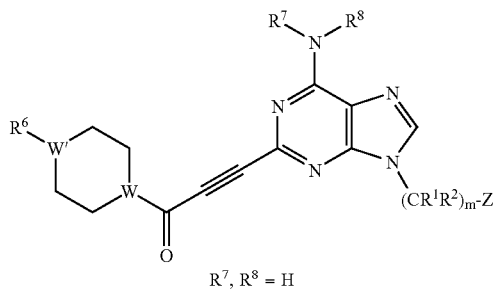

R⁷, R⁸ = H

| Compound | (CR¹R²)ₘ-Z | W | W' | R⁶ |
|---|---|---|---|---|
| NC344 | c-Pentyl | N | N | CO₂iPr |
| NC345 | Propargyl | CH | CH | COMe |
| NC346 | c-Pentyl | CH | N | COMe |
| NC347 | Propargyl | N | CH | COMe |
| NC348 | c-Pentyl | N | N | COMe |
| NC349 | Propargyl | CH | CH | COMe |
| NC350 | c-Pentyl | CH | N | COMe |
| NC351 | Propargyl | N | CH | COMe |
| NC352 | c-Pentyl | N | N | COMe |
| NC353 | Propargyl | CH | CH | COC(CH₃)₃ |
| NC354 | c-Pentyl | CH | N | COC(CH₃)₃ |
| NC355 | Propargyl | N | CH | COC(CH₃)₃ |
| NC356 | c-Pentyl | N | N | COC(CH₃)₃ |
| NC357 | Propargyl | CH | CH | COC(CH₃)₃ |
| NC358 | c-Pentyl | CH | N | COC(CH₃)₃ |
| NC359 | Propargyl | N | CH | COC(CH₃)₃ |
| NC360 | c-Pentyl | N | N | COC(CH₃)₃ |
| NC361 | Propargyl | CH | CH | COCH₂(CH₃)₃ |
| NC362 | c-Pentyl | CH | N | COCH₂(CH₃)₃ |
| NC363 | Propargyl | N | CH | COCH₂(CH₃)₃ |
| NC364 | c-Pentyl | N | N | COCH₂(CH₃)₃ |
| NC365 | Propargyl | CH | CH | COCH₂(CH₃)₃ |
| NC366 | c-Pentyl | CH | N | COCH₂(CH₃)₃ |
| NC367 | Propargyl | N | CH | COCH₂(CH₃)₃ |
| NC368 | c-Pentyl | N | N | COCH₂(CH₃)₃ |
| NC369 | Propargyl | CH | CH | C(O)N(CH₃)₂ |
| NC370 | c-Pentyl | CH | N | C(O)N(CH₃)₂ |
| NC371 | Propargyl | N | CH | C(O)N(CH₃)₂ |
| NC372 | c-Pentyl | N | N | C(O)N(CH₃)₂ |
| NC373 | Propargyl | CH | CH | C(O)N(CH₃)₂ |
| NC374 | c-Pentyl | CH | N | C(O)N(CH₃)₂ |
| NC375 | Propargyl | N | CH | C(O)N(CH₃)₂ |
| NC376 | c-Pentyl | N | N | C(O)N(CH₃)₂ |
| NC377 | Propargyl | CH | CH | C(O)N(CH₃)Et |
| NC378 | c-Pentyl | CH | N | C(O)N(CH₃)Et |
| NC379 | Propargyl | N | CH | C(O)N(CH₃)Et |
| NC380 | c-Pentyl | N | N | C(O)N(CH₃)Et |
| NC381 | Propargyl | CH | CH | C(O)N(CH₃)Et |
| NC382 | c-Pentyl | CH | N | C(O)N(CH₃)Et |
| NC383 | Propargyl | N | CH | C(O)N(CH₃)Et |
| NC384 | c-Pentyl | N | N | C(O)N(CH₃)Et |
| NC385 | Propargyl | CH | CH | C(O)N(CH₃)iPr |
| NC386 | c-Pentyl | CH | N | C(O)N(CH₃)iPr |
| NC387 | Propargyl | N | CH | C(O)N(CH₃)iPr |
| NC388 | c-Pentyl | N | N | C(O)N(CH₃)iPr |
| NC389 | Propargyl | CH | CH | C(O)N(CH₃)iPr |
| NC390 | c-Pentyl | CH | N | C(O)N(CH₃)iPr |
| NC391 | Propargyl | N | CH | C(O)N(CH₃)iPr |
| NC392 | c-Pentyl | N | N | C(O)N(CH₃)iPr |
| NC393 | Propargyl | CH | CH | C(O)N(CH₃)iBu |
| NC394 | c-Pentyl | CH | N | C(O)N(CH₃)iBu |
| NC395 | Propargyl | N | CH | C(O)N(CH₃)iBu |
| NC396 | c-Pentyl | N | N | C(O)N(CH₃)iBu |
| NC397 | Propargyl | CH | CH | C(O)N(CH₃)iBu |
| NC398 | c-Pentyl | CH | N | C(O)N(CH₃)iBu |
| NC399 | Propargyl | N | CH | C(O)N(CH₃)iBu |
| NC400 | c-Pentyl | N | N | C(O)N(CH₃)iBu |
| NC401 | Propargyl | CH | CH | C(O)NH(Et) |
| NC402 | c-Pentyl | CH | N | C(O)NH(Et) |
| NC403 | Propargyl | N | CH | C(O)NH(Et) |
| NC404 | c-Pentyl | N | N | C(O)NH(Et) |
| NC405 | Propargyl | CH | CH | C(O)NH(Et) |

TABLE 7-continued

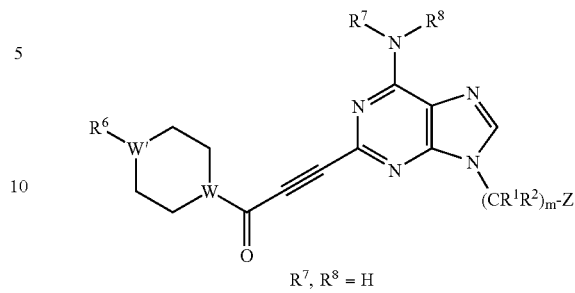

R⁷, R⁸ = H

| Compound | (CR¹R²)ₘ-Z | W | W' | R⁶ |
|---|---|---|---|---|
| NC406 | c-Pentyl | CH | N | C(O)NH(Et) |
| NC407 | Propargyl | N | CH | C(O)NH(Et) |
| NC408 | c-Pentyl | N | N | C(O)NH(Et) |
| NC409 | Propargyl | CH | CH | C(O)NH(iPr) |
| NC410 | c-Pentyl | CH | N | C(O)NH(iPr) |
| NC411 | Propargyl | N | CH | C(O)NH(iPr) |
| NC412 | c-Pentyl | N | N | C(O)NH(iPr) |
| NC413 | Propargyl | CH | CH | C(O)NH(iPr) |
| NC414 | c-Pentyl | CH | N | C(O)NH(iPr) |
| NC415 | Propargyl | N | CH | C(O)NH(iPr) |
| NC416 | c-Pentyl | N | N | C(O)NH(iPr) |
| NC417 | Propargyl | CH | CH | C(O)NH(iBu) |
| NC418 | c-Pentyl | CH | N | C(O)NH(iBu) |
| NC419 | Propargyl | N | CH | C(O)NH(iBu) |
| NC420 | c-Pentyl | N | N | C(O)NH(iBu) |
| NC421 | Propargyl | CH | CH | C(O)NH(iBu) |
| NC422 | c-Pentyl | CH | N | C(O)NH(iBu) |
| NC423 | Propargyl | N | CH | C(O)NH(iBu) |
| NC424 | c-Pentyl | N | N | C(O)NH(iBu) |
| NC425 | Propargyl | CH | CH | CH₂OCOCH₃ |
| NC426 | c-Pentyl | CH | N | CH₂OCOCH₃ |
| NC427 | Propargyl | N | CH | CH₂OCOCH₃ |
| NC428 | c-Pentyl | N | N | CH₂OCOCH₃ |
| NC429 | Propargyl | CH | CH | CH₂OCOCH₃ |
| NC430 | c-Pentyl | CH | N | CH₂OCOCH₃ |
| NC431 | Propargyl | N | CH | CH₂OCOCH₃ |
| NC432 | c-Pentyl | N | N | CH₂OCOCH₃ |
| NC433 | Propargyl | CH | CH | CH₂OCOEt |
| NC434 | c-Pentyl | CH | N | CH₂OCOEt |
| NC435 | Propargyl | N | CH | CH₂OCOEt |
| NC436 | c-Pentyl | N | N | CH₂OCOEt |
| NC437 | Propargyl | CH | CH | CH₂OCOEt |
| NC438 | c-Pentyl | CH | N | CH₂OCOEt |
| NC439 | Propargyl | N | CH | CH₂OCOEt |
| NC440 | c-Pentyl | N | N | CH₂OCOEt |
| NC441 | Propargyl | CH | CH | CH₂OCOiPr |
| NC442 | c-Pentyl | CH | N | CH₂OCOiPr |
| NC443 | Propargyl | N | CH | CH₂OCOiPr |
| NC444 | c-Pentyl | N | N | CH₂OCOiPr |
| NC445 | Propargyl | CH | CH | CH₂OCOiPr |
| NC446 | c-Pentyl | CH | N | CH₂OCOiPr |
| NC447 | Propargyl | N | CH | CH₂OCOiPr |
| NC448 | c-Pentyl | N | N | CH₂OCOiPr |
| NC449 | Propargyl | CH | CH | CH₂OCOiBu |
| NC450 | c-Pentyl | CH | N | CH₂OCOiBu |
| NC451 | Propargyl | N | CH | CH₂OCOiBu |
| NC452 | c-Pentyl | N | N | CH₂OCOiBu |
| NC453 | Propargyl | CH | CH | CH₂OCOiBu |
| NC454 | c-Pentyl | CH | N | CH₂OCOiBu |
| NC455 | Propargyl | N | CH | CH₂OCOiBu |
| NC456 | c-Pentyl | N | N | CH₂OCOiBu |

58. A pharmaceutical composition comprising a therapeutically effective amount of a compound of claim 1, and a pharmaceutically acceptable excipient.

59. The compound of claim 1, or a pharmaceutically acceptable salt thereof, in the form of a single stereoisomer or mixture of stereoisomers thereof.

60. A method for stimulating motor activity without dyskinesia in a mammal, comprising administering a therapeutically effective amount of an $A_{2A}$ anatagonist compound of claim 1 to the mammal in need of such treatment.

61. The method of claim 60, wherein the mammal suffers from a disorder selected from Huntington's disease, catalepsy, Parkinson's disease, and narcolepsy.

62. The method of claim 60 wherein the mammal suffers from a disorder selected from progressive supernuclear palsy, Huntington's disease, multiple system atrophy, corticobasal degeneration, Wilsons disease, Hallervorden-Spatz disease, progressive pallidal atrophy, Dopa-responsive dystonia-Parkinsonism, spasticity or other disoders of the basal ganglia which result in dyskinesias.

63. A compound of formula I:

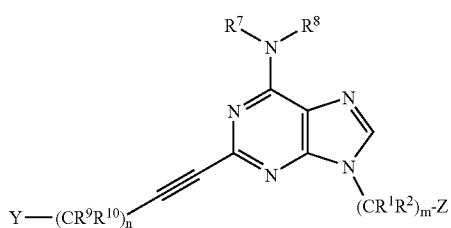

wherein $R^1$ and $R^2$ are hydrogen, m is 0, 1, 2 or 3 and Z is the moiety derived from the ring selected from the group consisting of furan, dihydro-furan, tetrahydrofuran, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with from 1 $R^a$ group;

Y is $-CR^3R^4R^5$ or $NR^4R^5$;

$R^3$ is selected from the group consisting of hydrogen, halo, $-OR^a$, $SR^a$, $(C_1-C_8)$alkyl, cyano, nitro, trifluoromethyl, trifluoromethoxy, $(C_3-C_8)$cycloalkyl, heterocycle, hetrocycle($C_1-C_8$)alkyl, aryl, aryl($C_1-C_8$)alkyl, heteroaryl, heteroaryl($C_1-C_8$)alkyl, $-CO_2R^a$, $R^aC(=O)O-$, $R^aC(=O)-$, $-OCO_2R^a$, $R^aR^bNC(=O)O-$, $R^bOC(=O)N(R^a)-$, $R^aR^bN-$, $R^aR^bNC(=O)-$, $R^aC(=O)N(R^b)-$, $R^aR^bNC(=O)N(R^b)-$, $R^aR^bNC(=S)N(R^b)-$, $R^aOC(=S)-$, $R^aC(=S)-$, $-SSR^a$, $R^aS(=O)-$, $R^aS(=O)_2-$; or if the ring formed from the group $CR^3R^4R^5$ is aryl or heteroaryl or partially unsaturated, then $R^3$ can be absent;

$R^4$ and $R^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of $-O-$, $-S-$, $-SO-$, $-S(O)^2-$ or amine ($-NR^a-$) in the ring, wherein any ring comprising $R^4$ and $R^5$ is optionally further substituted with from 1 to 14 $R^6$ groups; wherein each $R^6$ is independently selected from the group consisting of halo, $-OR^a$, $-SR^a$, substituted or unsubstituted $(C_1-C_8)$alkyl, cyano, nitro, trifluoromethyl, trifluoromethoxy, $(C_3-C_8)$cycloalkyl, $(C_6-C_{12})$ bicycloalkyl, heterocycle, hetrocyclyl($C_1-C_8$)alkyl, aryl, aryl($C_1-C_8$)alkyl, heteroaryl, heteroaryl($C_1-C_8$)alkyl, $-CO_2R^a$, $R^aC(=O)O-$, $R^aC(=O)-$, $-OCO_2R^a$, $R^aR^bNC(=O)O-$, $R^bOC(=O)N(R^a)-$, $R^aR^bN-$, $R^aR^bNC(=O)-$, $R^aC(=O)N(R^b)-$, $R^aR^bNC(=O)N(R^b)-$, $R^aR^bNC(=S)N(R^b)-$, $R^aOC(=S)-$, $R^aC(=S)-$, $-SSR^a$, $R^aS(=O)-$ or two $R^6$ groups and the atom to which they are attached combined to form C=O or C=S, or wherein two $R^6$ groups together with the atom or atoms to which they are attached can form a carbocyclic or heterocyclic ring;

$R^7$ and $R^8$ are each independently hydrogen, $(C_1-C_8)$ alkyl, $(C_3-C_8)$cycloalkyl, aryl or aryl($C_1-C_8$)alkylene, heteroaryl, heteroaryl($C_1-C_8$)alkylene-; or wherein $R^7$ and $R^8$ together with the nitrogen atom to which they attach form a heterocycle or heteroaromatic ring;

$R^9$ and $R^{10}$ are each independently selected from the group consisting of hydrogen, halogen, $-NH_2$, $-OH$, $-SH$, $-NHCH_3$, $-N(CH_3)_2$, $-OCH_3$, $-SCH_3$, $(C_1-C_8)$alkyl, aryl and aryl($C_1-C_8$)alkyl, wherein $R^9$ and $R^{10}$ are optionally substituted with 1 to 4 substituents of $R^a$, wherein the alkyl is optionally interrupted by 1 to 4 heteroatoms selected from $-O-$, $-S-$, $-SO-$, $-S(O)_2-$ or amino ($-NR^a-$), or where $R^9$ and $R^{10}$ are independently absent, with the proviso that $R^a$ is not SH or halogen in the case where the $R^9$ or $R^{10}$ to which $R^a$ is bound is halogen, $-NH_2$, $-OH$, $-SH$, $-NHCH_3$, $-N(CH_3)_2$, $-OCH_3$ or $-SCH_3$;

$R^a$ and $R^b$ are each independently selected from the group consisting of hydrogen, halogen, $-NH_2$, $-OH$, $-SH$, $-NHCH_3$, $-N(CH_3)_2$, $-OCH_3$, $-SCH_3$, propargyl, cyano, $-OS(O_2)H$, $-OS(O_2)OH$, $-OS(O_2)CH_3$, $-OS(O_2)OCH_3$, $(C_1-C_8)$alkyl, aryl, aryl($C_1-C_8$)alkyl, $(C_3-C_8)$cycloalkyl, $(C_6-C_{12})$bicycloalkyl, cycloalkyl $(C_1-C_8)$alkyl, bicycloalkyl($C_6-C_{12}$)alkyl, heteroaryl and heteroaryl($C_1-C_8$)alkyl, wherein the alkyl and cycloalkyl are optionally interrupted with 1-4 heteroatoms selected from the group consisting of $-O-$, $-S-$, $-SO-$, $-S(O)_2-$ and amino ($-NR^c-$); and wherein the alkyl, cycloalkyl, aryl and heteroaryl are optionally substituted with 1, 2, 3 or 4 substituents selected from the group consisting of $-OR^c$, $-NR^cR^c$, $SR^c$, cyano, $-OS(O_2)H$, $-OS(O_2)OH$, $-OS(O_2)CH_3$ and $-OS(O_2)OCH_3$, provided that the point of attachment of $R^a$ or $R^b$ is not a heteroatom when it is attached to another heteroatom;

$R^c$ is selected from the group consisting of hydrogen and $(C_1-C_8)$alkyl; and n is 0, 1, 2 or 3, provided that when m is 0, Z is not attached via a heteroatom, and when n is 0, Y is not $-NR^4R^5$; or a pharmaceutically acceptable salt thereof, optionally in the form of a single stereoisomer or mixture of stereoisomers thereof.

64. A compound of formula II:

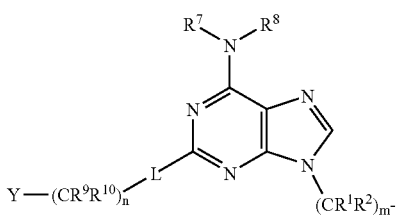

II wherein $R^1$ and $R^2$ are hydrogen, m is 0, 1, 2 or 3 and Z is selected from the group consisting of furan, dihydro-furan, tetrahydrofuran, thiophene, pyrrole, 2H-pyrrole, 2-pyrroline, 3-pyrroline, pyrrolidine, 1,3-dioxolane, oxazole, thiazole, imidazole, dihydro-imidazole, 2-imidazoline, imidazolidine, pyrazole, 2-pyrazoline, pyrazolidine, isoxazole, isothiazole, 1,2,3-oxadiazole, 1,2,4-oxadiazole, 1,2,3-triazole, 1,2,4-triazole, 1,3,4-thiadiazole, 2H-pyran, 1H-tetrazole, 4H-pyran, pyridine, dihydro-pyridine, tetrahydro-pyridine, piperidine, 1,4-dioxane, morpholine, 1,4-dithiane, thiomorpholine, pyridazine, pyrimidine, dihydro-pyrimidine, tetrahydro-pyrimidine, hexahydro-pyrimidine, pyrazine, dihydro-pyrazine, tetrahydro-pyrazine, piperazine, 1,3,5-triazine and 1,3,5-trithiane, wherein each Z group is optionally substituted with 1 $R^a$ group;

L is a linker selected from the group consisting of —$(C_1$–$C_3)$alkyl-C≡C—, —C≡C—$(C_1$–$C_3)$alkyl-, —$(CH_2)_{1-3}$—CH=CH—, —CH=CH—$(CH_2)_{1-3}$—, —$(CH_2)_{1-2}$—CH=CH—$CH_2$— and —$CH_2$—CH=CH—$(CH_2)_{1-2}$—;

Y is —$CR^3R^4R^5$ or $NR^4R^5$;

$R^3$ is selected from the group consisting of hydrogen, halo, —$OR^a$, $SR^a$, $(C_1$–$C_8)$alkyl, cyano, nitro, trifluoromethyl, trifluoromethoxy, $(C_3$–$C_8)$cycloalkyl, heterocycle, hetrocycle$(C_1$–$C_8)$alkyl, aryl, aryl$(C_1$–$C_8)$alkyl, heteroaryl, heteroaryl$(C_1$–$C_8)$alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$—, —$SSR^a$, $R^aS(=O)$—, and $R^aS(=O)_2$—; or if the ring formed from the group $CR^3R^4R^5$ is aryl or heteroaryl or partially unsaturated, then $R^3$ can be absent;

$R^4$ and $R^5$ together with the atoms to which they are attached form a saturated or partially unsaturated, mono-, bi- or tricyclic or aromatic ring having 3, 4, 5, 6, 7, 8, 9, 10, 11 or 12 ring atoms, wherein the ring atoms are optionally interrupted by 1, 2, 3 or 4 heteroatoms selected from the group consisting of —O—, —S—, —SO—, —$S(O)_2$— or amine (—$NR^a$—) in the ring, wherein any ring comprising $R^4$ and $R^5$ is optionally further substituted with from 1 to 14 $R^6$ groups; wherein each $R^6$ is independently selected from the group consisting of halo, —$OR^a$, —$SR^a$, substituted or unsubstituted $(C_1$–$C_8)$alkyl, cyano, nitro, trifluoromethyl, trifluoromethoxy, $(C_3$–$C_8)$cycloalkyl, $(C_6$–$C_{12})$bicycloalkyl, heterocycle, hetrocyclyl$(C_1$–$C_8)$alkyl, aryl, aryl$(C_1$–$C_8)$alkyl, heteroaryl, heteroaryl$(C_1$–$C_8)$alkyl, —$CO_2R^a$, $R^aC(=O)O$—, $R^aC(=O)$—, —$OCO_2R^a$, $R^aR^bNC(=O)O$—, $R^bOC(=O)N(R^a)$—, $R^aR^bN$—, $R^aR^bNC(=O)$—, $R^aC(=O)N(R^b)$—, $R^aR^bNC(=O)N(R^b)$—, $R^aR^bNC(=S)N(R^b)$—, $R^aOC(=S)$—, $R^aC(=S)$—, —$SSR^a$, $R^aS(=O)$— or two $R^6$ groups and the atom to which they are attached combined to form C=O or C=S, or wherein two $R^6$ groups together with the atom or atoms to which they are attached can form a carbocyclic or heterocyclic ring;

$R^7$ and $R^8$ are each independently hydrogen, $(C_1$–$C_8)$ alkyl, $(C_3$–$C_8)$cycloalkyl, aryl or aryl$(C_1$–$C_8)$alkylene, heteroaryl, heteroaryl$(C_1$–$C_8)$alkylene; or wherein $R^7$ and $R^8$ together with the nitrogen atom to which they attach form a heterocycle or heteroaromatic ring;

$R^9$ and $R^{10}$ are each independently selected from the group consisting of hydrogen, halogen, —$NH_2$, —OH, —SH, —$NHCH_3$, —$N(CH_3)_2$, —$OCH_3$, —$SCH_3$, $(C_1$–$C_8)$alkyl, aryl and aryl$(C_1$–$C_8)$alkyl, wherein $R^9$ and $R^{10}$ are optionally substituted with 1 to 4 substituents of $R^a$, wherein the alkyl is optionally interrupted by 1 to 4 heteroatoms selected from —O—, —S—, —SO—, —$S(O)_2$— or amino (—$NR^a$—), or where $R^9$ and $R^{10}$ are independently absent, with the proviso that $R^a$ is not SH or halogen in the case where the $R^9$ or $R^{10}$ to which $R^a$ is bound is halogen, —$NH_2$, —OH, —SH, —$NHCH_3$, —$N(CH_3)_2$, —$OCH_3$ or —$SCH_3$;

$R^a$ and $R^b$ are each independently selected from the group consisting of hydrogen, halogen, —$NH_2$, —OH, —SH, —$NHCH_3$, —$N(CH_3)_2$, —$OCH_3$, —$SCH_3$, propargyl, cyano, —$OS(O_2)H$, —$OS(O_2)OH$, —$OS(O_2)CH_3$, —$OS(O_2)OCH_3$, $(C_1$–$C_8)$alkyl, aryl, aryl$(C_1$–$C_8)$alkyl, $(C_3$–$C_8)$cycloalkyl, $(C_6$–$C_{12})$bicycloalkyl, cycloalkyl $(C_1$–$C_8)$alkyl, bicycloalkyl$(C_6$–$C_{12})$alkyl, heteroaryl and heteroaryl$(C_1$–$C_8)$alkyl, wherein the alkyl and cycloalkyl are optionally interrupted with 1–4 heteroatoms selected from the group consisting of —O—, —S—, —SO—, —$S(O)_2$— and amino (—$NR^c$—); and wherein the alkyl, cycloalkyl, aryl and heteroaryl are optionally substituted with 1, 2, 3 or 4 substituents selected from the group consisting of —$OR^c$, —$NR^cR^c$, $SR^c$, cyano, —$OS(O_2)H$, —$OS(O_2)OH$, —$OS(O_2)CH_3$ and —$OS(O_2)OCH_3$, provided that the point of attachment of $R^a$ or $R^b$ is not a heteroatom when it is attached to another heteroatom;

$R^c$ is selected from the group consisting of hydrogen and $(C_1$–$C_8)$alkyl; and m is 0 to 8; n is 0, 1, 2 or 3, provided that when n is 0, Z is not attached via a heteroatom, and when n is 0, Y is not —$NR^4R^5$; or a pharmaceutically acceptable salt thereof, optionally in the form of a single stereoisomer or mixture of stereoisomers thereof.

65. A pharmaceutical composition comprising a therapeutically effective amount of a compound of claim 2, and a pharmaceutically acceptable excipient.

66. A pharmaceutical composition comprising a therapeutically effective amount of a compound of claim 5, and a pharmaceutically acceptable excipient.

67. A method for stimulating motor activity without dyskinesia in a mammal, comprising administering a therapeutically effective amount of an $A_{2A}$ anatagonist compound of claim 2 to the mammal in need of such treatment.

68. A method for stimulating motor activity without dyskinesia in a mammal, comprising administering a therapeutically effective amount of an $A_{2A}$ anatagonist compound of claim 5 to the mammal in need of such treatment.

69. A compound according to claim 56, wherein the compound is:

2-{2-[1(S)-Hydroxy-3(R)-methyl-1-cyclohexyl]ethyn-1-yl}-9-propargyladenine (2) or a pharmaceutically acceptable salt thereof, optionally in the form of a single stereoisomer or mixture of stereoisomers thereof.

70. A compound according to claim 56, wherein the compound is:

9-Cyclopentyl-2-{2-[1(S)-hydroxy-3(R)-methyl-1-cyclohexyl]ethyn-1-yl}adenine (3) or a pharmaceutically acceptable salt thereof, optionally in the form of a single stereoisomer or mixture of stereoisomers thereof.

71. A compound according to claim 56, wherein the compound is:

2-{2-[1(S)-Hydroxy-3(R)-methyl-1-cyclohexyl]ethyn-1-yl}-N6-(3-methoxybenzyl)-9-(propargyl)adenine (36) or a pharmaceutically acceptable salt thereof, optionally in the form of a single stereoisomer or mixture of stereoisomers thereof.

72. A compound according to claim 56, wherein the compound is:

2-{2-[1(S)-Hydroxy-3(R)-methyl-1-cyclohexyl]ethyn-1-yl}-9-(propargyl)-N6-(pyridin-2-ylmethyl)adenine (37) or a pharmaceutically acceptable salt thereof, optionally in the form of a single stereoisomer or mixture of stereoisomers thereof.

73. A compound according to claim 56, wherein the compound is:

9-Cyclobutylmethyl-2-{2-[hydroxy-adamantan-2-yl]ethyn-1-yl}adenine (46) or a pharmaceutically acceptable salt thereof, optionally in the form of a single stereoisomer or mixture of stereoisomers thereof.

74. A compound according to claim 56, wherein the compound is:

9-Cyclopentyl-2-{2-[hydroxy-adamantan-2-yl]ethyn-1-yl}adenine (50) or a pharmaceutically acceptable salt thereof, optionally in the form of a single stereoisomer or mixture of stereoisomers thereof.

75. A compound according to claim 56, wherein the compound is:

2-{2-[Hydroxy-adamantan-2-yl]ethyn-1-yl}-9-propargyladenine (51) or a pharmaceutically acceptable salt thereof, optionally in the form of a single stereoisomer or mixture of stereoisomers thereof.

76. A compound according to claim 56, wherein the compound is: 2-{2-[Hydroxy-norbornan-2-yl]ethyn-1-yl}-9-propargyladenine or a pharmaceutically acceptable salt thereof, optionally in the form of a single stereoisomer or mixture of stereoisomers thereof.

77. A compound according to claim 56, wherein the compound is:

2-{3-[1-(Methoxycarbanoyl)piperidin-4-yl]propyn-1-yl}-9-propargyladenine (63) or a pharmaceutically acceptable salt thereof, optionally in the form of a single stereoisomer or mixture of stereoisomers thereof.

78. A pharmaceutical composition comprising a therapeutically effective amount of a compound of claim 69, and a pharmaceutically acceptable excipient.

79. A pharmaceutical composition comprising a therapeutically effective amount of a compound of claim 70, and a pharmaceutically acceptable excipient.

80. A pharmaceutical composition comprising a therapeutically effective amount of a compound of claim 71, and a pharmaceutically acceptable excipient.

81. A pharmaceutical composition comprising a therapeutically effective amount of a compound of claim 72, and a pharmaceutically acceptable excipient.

82. A pharmaceutical composition comprising a therapeutically effective amount of a compound of claim 73, and a pharmaceutically acceptable excipient.

83. A pharmaceutical composition comprising a therapeutically effective amount of a compound of claim 74, and a pharmaceutically acceptable excipient.

84. A pharmaceutical composition comprising a therapeutically effective amount of a compound of claim 75, and a pharmaceutically acceptable excipient.

85. A pharmaceutical composition comprising a therapeutically effective amount of a compound of claim 76, and a pharmaceutically acceptable excipient.

86. A pharmaceutical composition comprising a therapeutically effective amount of a compound of claim 77, and a pharmaceutically acceptable excipient.

* * * * *